(12) United States Patent
Oniciu et al.

(10) Patent No.: US 9,708,354 B2
(45) Date of Patent: Jul. 18, 2017

(54) METHODS FOR THE SYNTHESIS OF SPHINGOMYELINS AND DIHYDROSPHINGOMYELINS

(71) Applicant: Cerenis Therapeutics Holding SA, Labège (FR)

(72) Inventors: Daniela Carmen Oniciu, Toulouse (FR); Stefan Heckhoff, Loerrach (DE); Benoit Oswald, Illzach (FR); Peter Rebmann, Prattein (CH); Andreas Peer, Sion (CH); Miguel Gonzalez, Niederdorf (CH); Patrik Sauter, Ettingen (CH)

(73) Assignee: Cerenis Therapeutics Holding SA, Labege (FR)

( * ) Notice: Subject to any disclaimer, the term of this patent is extended or adjusted under 35 U.S.C. 154(b) by 0 days.

(21) Appl. No.: 13/844,379

(22) Filed: Mar. 15, 2013

(65) Prior Publication Data

US 2014/0275590 A1 Sep. 18, 2014

(51) Int. Cl.
   C07F 9/24 (2006.01)
   C07F 9/6574 (2006.01)
   C07F 9/10 (2006.01)

(52) U.S. Cl.
   CPC .......... C07F 9/65742 (2013.01); C07F 9/106 (2013.01)

(58) Field of Classification Search
   CPC ......... C07F 9/106; C07F 9/24; C07F 9/65742
   See application file for complete search history.

(56) References Cited

U.S. PATENT DOCUMENTS

| | | |
|---|---|---|
| 4,952,683 A | 8/1990 | Tschannen et al. |
| 5,220,043 A | 6/1993 | Dong et al. |
| 5,766,627 A | 6/1998 | Sankaram et al. |
| 6,132,766 A | 10/2000 | Sankaram et al. |
| 6,610,835 B1 | 8/2003 | Liotta et al. |
| 7,470,664 B2 | 12/2008 | Holloway et al. |
| 7,629,385 B2 | 12/2009 | Braxmeier et al. |
| 7,687,652 B2 | 3/2010 | Rochlin et al. |
| 7,811,602 B2 | 10/2010 | Cullis et al. |
| 8,093,395 B2 | 1/2012 | Nishizawa et al. |
| 8,216,999 B2 | 7/2012 | Holloway et al. |
| 2006/0217312 A1 | 9/2006 | Dasseux |
| 2007/0027071 A1 | 2/2007 | Holloway et al. |
| 2009/0124661 A1 | 5/2009 | Holloway et al. |
| 2010/0099881 A1 | 4/2010 | Nishizawa et al. |
| 2011/0244029 A1 | 10/2011 | Barenholz et al. |
| 2011/0250266 A1 | 10/2011 | Barenholz et al. |
| 2014/0316154 A1 | 10/2014 | Oniciu et al. |
| 2016/0075634 A1 | 3/2016 | Oniciu et al. |

FOREIGN PATENT DOCUMENTS

| | | |
|---|---|---|
| EP | 2133335 | 12/2009 |
| JP | 2006-045113 | 2/2006 |
| JP | 2007-204384 | 8/2007 |
| WO | WO 99/41266 | 8/1999 |
| WO | WO 2005/068480 | 7/2005 |
| WO | WO 2006/002909 | * 1/2006 |
| WO | WO 2006/014006 | 2/2006 |
| WO | WO 2010/041255 | 4/2010 |
| WO | WO 2012/109162 | 8/2012 |
| WO | WO 2014/108564 | 7/2014 |
| WO | WO 2014/140787 | 9/2014 |

OTHER PUBLICATIONS

Schmidt et al. (Angew. Chem. Int. Ed. Engl. 24 (1985) No. 1; p. 65-66).*
Byun et al. (J. Org. Chem. 1994, 59, 6495-6498).*
Rzepa (Solvation Difference Maps as Probes of Intramolecular Hydrogen Bonding: An Application of Hyperactive Molecules. Jun. 21, 2011—http://www.ch.ic.ac.uk/rzepa/eccc/eccc.htm)I.*
"Dielectric Constant of Common Solyents" (available online May 12, 2008; http://depts.washington.edu/eooptic/linkfiles/dielectric_chart[1].pdf).*
Dong and Butcher (Chemistry and Physics of Lipids 66 (1993) 41-46).*
Weiss et al. (Chemistry and Physics of Lipids 102 (1999) 3-12).*
Duffin et al. (J. Chem. Soc., Perkin Trans 1, 2000, 2237-2242).*
Murakami et al. (Bioorganic & Medicinal Chemistry Letters, (1997) vol. 7, No. 13, pp. 1725-1728.*
Aoki, H. et al., "Structural property and function of D-erythro asymmetric chain sphingomyelins as studied by microcalorimetry and electron microscopy," Journal of Thermal Analysis and Calorimetry, 92(2):443-449 (2008).
Bushnev, A. S. et al., "Practical synthesis of N-palmitoylsphingomyelin and N-palmitoyldihydrosphingomyelin," Methods in Enzymology, 311(Sphingolipid Metabolism and Cell Signalling, Part A):535-547 (2000).
Cohen, R. et al., "Preparation and characterization of well defined D-erythro sphingomyelins," Chemistry and Physics of Lipids, 35(4):371-384 (1984).
Dong, Z. et al., "An efficient route to N-palmitoyl-D-erythro-sphingomyelin and its $^{13}$C-labeled derivatives," Chemisty and Physics of Lipids, 66(1-2):41-46 (1993).
Dong, Z. et al., "A useful synthesis of D-erythro-sphingomyelins," Tetrahedron Letters, 32(39):5291-5294 (1991).
Garner, P. et al., "1,1,-dimethylethyl (S)- or (R)-4-formyl-2,2-dimethyl-3-oxazolidinecarboxylate: a useful serinal derivative," Organic Synthesis, Coll. vol. 9, p. 300 (1998): vol. 70, p. 18 (1992).
Garner, P. et al., "A stereodivergent synthesis of D-erythro-sphingosine and D-threo-sphingosine from L-serine," J. Org. Chem., 53(18):4395-4398 (1988).

(Continued)

*Primary Examiner* — Valerie Rodriguez-Garcia
(74) *Attorney, Agent, or Firm* — Cooley LLP

(57) ABSTRACT

The present invention includes methods for the synthesis of sphingomyelins and dihydrosphingomyelins. The present invention also includes methods for the synthesis of sphingosines and dihydrosphingosines. The present invention further includes methods for the synthesis of ceramides and dihydroceramides.

5 Claims, 7 Drawing Sheets

(56) References Cited

OTHER PUBLICATIONS

Irako, N. et al., "Total synthesis of sulfobacin A (Flavocristamide B)," Tetrahedron Letters, 39:5793-5796 (1998).
Koskinen, P. M. et al., "Total synthesis of sphingosine and its analogs," Chemical and Enzymatic Synthesis, Methods in Enzymology, 311:458-479 (1999).
Labeeuw, O. et al., "Total synthesis of sulfobacin A through dynamic kinetic resolution of a racemic β-keto-α-amino ester hydrochloride," Tetrahedron: Asymmetry, 15:1899-1908 (2004).
Labeeuw, O. et al., "A short total synthesis of sulfobacin A," Tetrahedron Letters, 44:6383-6386 (2003).
Lee, Y. M. et al., "A practical and cost-effective synthesis of D-erythro-sphingosine from D-ribo-phytosphingosine via a cyclic sulfate intermediate," Synthesis, 6:867-872 (2011).
Levene, P. A. et al., "Sphingosine. IV. Some Derivatives of Sphingosine and Dihydrosphingosine," [online]. [Retrieved from the internet on Mar. 28, 2012], <www.jbc.org>, pp. 63-68 (1915).
Mills, K. et al., "The synthesis of internal standards for the quantitative determination of sphingolipids by tandem mass spectrometry," Rapid Communications in Mass Spectrometry, 19(12):1739-1748 (2005).
Morigaki, E. et al., "Syntheses of sphingomyelins and ceramides bearing a docosahexaenoyl or arachidonoyl group," Bioscience, Biotechnology, and Biochemistry, 62(10):2070-2072 (1998).
Radin, N. S., "Preparative scale isolation of sphingosine," J. Lipid Res., 31:2291-2293 (1990).
Ramstedt, B. et al., "Interaction of cholesterol with sphingomyelins and acyl-chain-matched phosphatidylcholines: a comparative study of the effect of the chain length," Biophysical Journal, 76(2):908-915 (1999).
Shioiri, T. et al., "An efficient synthesis of sulfobacin A (flavocristamide B), sulfobacin B, and flavocristamide A," Tetrahedron, 56:9129-9142 (2000).
Smaby, J. M. et al., "The interfacial elastic packing interactions of galactosylceramides, sphingomyelins, and phosphatidylcholines," Biophysical Journal, 70(2):868-877 (1996).
Subbaiah, P. V. et al., "Effect of double bond geometry in sphingosine base on the antioxidant function of sphingomyelin," Archives of Biochemistry and Biophysics, 481(1):72-79 (2009).
Urban, M. et al., "Complexity and pitfalls of mass spectrometry-based targeted metabolomics in brain research," Analytical Biochemistry, 406(2):124-131 (2010).
Van Overmeire, I. et al., "Effect of aromatic short-chain analogues of ceramide on axonal growth in hippocampal neurons," J. Med. Chem., 42:2697-2705 (1999).
Weis, A. L., "New approaches to synthesis of stereospecific sphingomyelin," Chemistry and Physics of Lipids, 102(1-2):3-12 (1999).
Welti, R. et al., "Lipidomic analysis of toxoplasma gondii reveals unusual polar lipids," Biochemistry, 46(48):13882-13890 (2007).
Yamamoto, T. et al. "Versatile synthetic method for sphingolipids and functionalized sphingosine derivatives via olefin cross metathesis," Organic Letters, 8(24):5569-5572 (2006).
Office Action for U.S. Appl. No. 14/693,520, mailed Jun. 14, 2016, 7 pages.
Van Kuijk, F. J. G. M. et al., "Transesterification of phospholipids or triglycerides to fatty acid benzyl esters with simultaneous methylation of free fatty acids for gas-liquid chromatographic analysis," J. Lipid Res., 27:452-456 (1986).
Clayden, Jonathan, et al., Organic Chemisty 342-343 (2001).
Wuts, Peter G. M. and Greene, Theodora W., Greene's Protective Groups in Organic Synthesis, 990-1000 (4th ed. 2007).

Bittman, R. et al., "Methanolysis of sphingomyelin: toward an epimerization-free methodology for the preparation of D-erythro-sphingosylphosphocholine," J. Lipid Res., 41:2089-2093 (2000).
Grossman, M. W. et al., "Conversion of erythro-D-sphinganine to its $[1\text{-}^2H_1]$ and $[1\text{-}^3H_1]$ derivatives," J. of Lipid Res., 25:729-737 (Aug. 1984).
Zhukova, I. G. et al., "Synthesis of 3-O-Alkylcerebrosides," N. D. Zelinskii Institute of Organic Chemistry, Academy of Sciences of the USSR, pp. 356-363 Consultants Bureau (1970). Translated from Izvestiya Akademii Nauk SSSR, Seriya Khimicheskaya, No. 2, pp. 411-419 (Feb. 1970). Original article submitted Sep. 16, 1968.
Koskinen, P. M., "Sphingosine, an Enigmatic Lipid: A Review of Recent Literature Syntheses," Synthesis, 8:1075-1091 (1998).
European Search Report for European Application No. 13306056.6, mailed Nov. 20, 2013, 6 pages.
Invitation to Pay Additional Fees and Partial International Search for International Application No. PCT/IB2014/000494, mailed Aug. 20, 2014, 7 pages.
International Search Report and Written Opinion for International Application No. PCT/IB2014/000494, mailed Dec. 19, 2014, 16 pages.
Office Action for U.S. Appl. No. 14/213,269, mailed Oct. 23, 2014, 12 pages.
Bradley, R. M., "An improved method for the determination of long-chain fatty acid amides," Biochimica et Biophysica Acta, Lipids and Lipid Metabolism, 106(2):417-418 (1965).
Carey, F. A. et al., "Advanced Organic Chemistry," Fourth Edition, Part A; Structure and Mechanisms, Kluwer Academic/Plenum Publishers (2000), pp. 484-488.
Groth, U. et al., "Asymmetric synthesis of D-erythro-Sphingosine," Tetrahedron, 47(16/17):2835-2842 (1991).
Hori, T. et al., "Biochemistry of shellfish lipid. III. Purification and elemental analysis of ceramide aminoethylphosphonate from Corbicula complex lipid mixtures," The Journal of Biochemistry, 59(6):570-573 (1966).
Krivit, W. et al., "Identification and quantitation of free ceramides in human platelets," Journal of Lipid Research, 13(4):525-530 (1972).
Levene, P. A. et al., "On Sphingosine: Second Paper. The Oxidation of Sphingosine and Dihydrosphingosine," Journal of Biological Chemistry, 16:549-553 (1914).
Mackey, R. H. et al., "High-Density Lipoprotein Cholesterol and Particle Concentrations, Carotid Atherosclerosis, and Coronary Events," Journal of the American College of Cardiology, 60(6):508-516 (2012).
Ramesha, C. S. et al., "Changes in the lipid composition and physical properties of Tetrahymena ciliary membranes following low-temperature acclimation," Biochemistry, 21(15):3612-3617 (1982).
Shapiro, D. et al., "Synthetic studies on sphingolipids. VI. The total syntheses of cerasine and phrenosine," J. Am. Chem. Soc., 83:3327-3332 (1961).
Shapiro, D., "Chemistry of Sphingolipids," Chemistry of Natural Products Series, Lederer, E. (Ed.), Hermann, Paris (1969), 108 pages.
Shoyama, Y. et al., "Total synthesis of sterospecific sphingosine and ceramide," Journal of Lipid Research, 19(2):250-259 (1978).
Tardy, C. et al., "CER-001, a HDL-mimetic, stimulates the reverse lipid transport and atherosclerosis regression in high cholesterol diet-fed LDL-receptor deficient mice," Atherosclerosis, 232:110-118 (2014).
Wuts, P. G. M. et al., "Greene's Protective Groups in Organic Synthesis," Fourth Edition, John Wiley & Sons, Inc. (2007), pp. 990-1000.

* cited by examiner

¹H spectrum of Egg Sphingomyelin

¹H spectrum of synthetic N-Palmitoyl-D-erythro-Sphyngosylphosphorylcholine $^1$H spectrum of the reaction mixture of R-MPA and synthetic N-Palmitoyl-D-erythro-Sphyngosylphosphorylcholine 1H spectrum of the reaction mixture of R-MPA and synthetic N-Palmitoyl-D-erythro-Sphyngosylphosphorylcholine $^1$H spectrum of the reaction mixture of egg sphingomyelin with an excess of the mixture of 2R+1S-MPA, DCC and DMAP (bottom) and the TOCSY1D spectra with selective excitation of H2 in the R-MPA (top) and S-MPA (bottom) esters.

METHODS FOR THE SYNTHESIS OF SPHINGOMYELINS AND DIHYDROSPHINGOMYELINS

BACKGROUND OF THE INVENTION

Sphingomyelins are the major phospholipid components of biological membranes and plasma lipoproteins. Like all sphingolipids, sphingomyelins consist of a ceramide core (sphingosine bound to a fatty acid via an amide linkage) and a polar head group, which is either phosphorylcholine or phosphoethanolamine (Formulae 1, top). Dihydrosphingomyelins are the saturated homologues of sphingomyelins, and have a saturated ceramide core, namely dihydrosphingosine bound to a fatty acid via an amide linkage (Formulae I, bottom).

Formulae 1

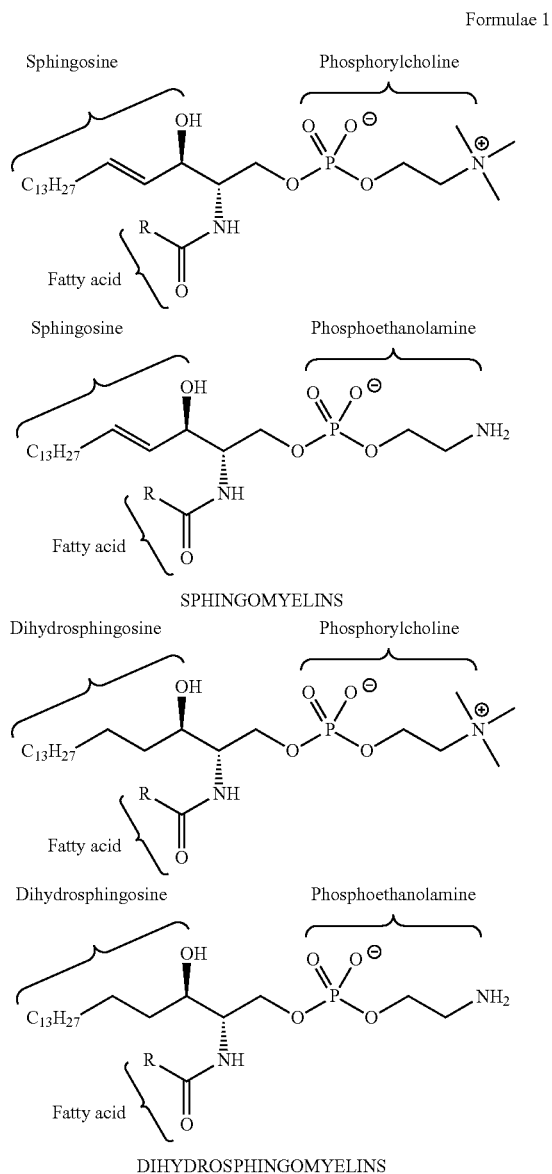

SPHINGOMYELINS

DIHYDROSPHINGOMYELINS

The sphingosine typically found in naturally occurring sphingomyelin is an 18-carbon amino alcohol with an unsaturated hydrocarbon chain having a stereo chemical configuration of D-erythro. The IUPAC name for this sphingosine is (2S,3R,E)-2-aminooctadec-4-ene-1,3-diol (Compound A). The dihydrosphingosine is its saturated homologue with the IUPAC name (2S,3R)-2-aminooctadecane-1,3-diol (Compound B).

Commercially available sphingomyelins are usually naturally products that comprise mixtures of naturally occurring sphingomyelins. The actual composition of this mixture varies depending on the biological source and contains various fatty acid chain lengths. The N-palmitoyl sphingomyelin is a major component in the natural sphingomyelins.

N-Palmitoyl-D-erythro-trans-sphingosylphosphorylcholine (Compound C), one of the isomers of palmitoyl sphingomyelin, which has the IUPAC name N-((2S,3R,E)-1,3-dihydroxyoctadec-4-en-2-yl)palmitamide, is believed to be the main naturally-occurring isomer. Its corresponding dihydrosphingomyelin, N-Palmitoyl-D-erythro-trans-dihydrosphingosylphosphorylcholine (Compound D), has the IUPAC name (2S,3R)-3-hydroxy-2-palmitamidooctadecyl (2-(trimethylammonio)ethyl)phosphate

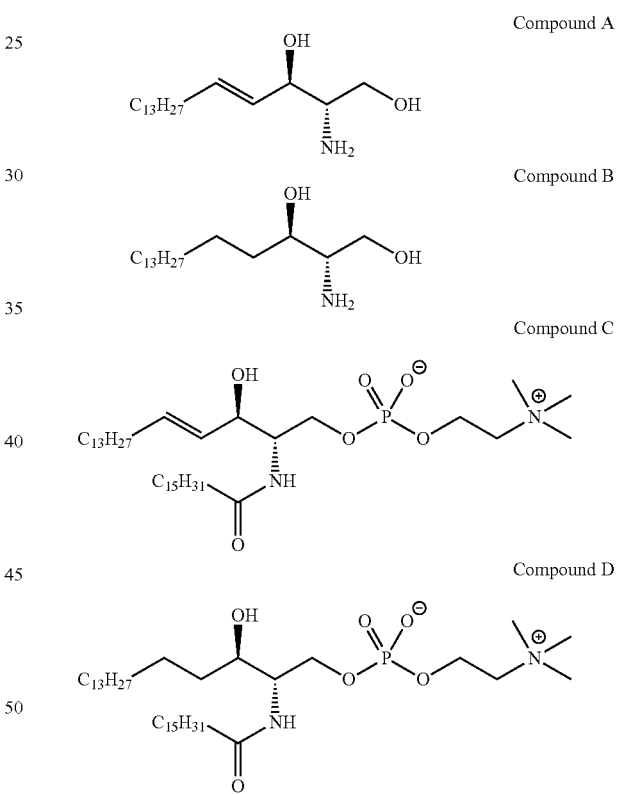

Industrially and economically-relevant synthetic alternatives of this natural source of sphingomyelin have yet to be developed. Synthetic pathways known in the art have not been useful for the large scale synthesis of sphingomyelins, particularly those with fatty acids having 12 to 25 carbons.

The corresponding sphingosine (or ceramide) is N-Palmitoyl-D-erythro-trans-sphingosine (Compound E) and N-Palmitoyl-D-erythro-trans-dihydrosphingosine (Compound F) are intermediates in the synthesis of N-Palmitoyl-D-erythro-trans-sphingosylphosphorylcholine and N-Palmitoyl-D-erythro-trans-dihydrosphingosylphosphorylcholine respectively.

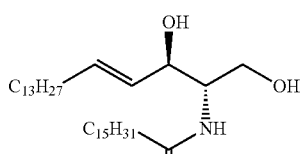

Compound E

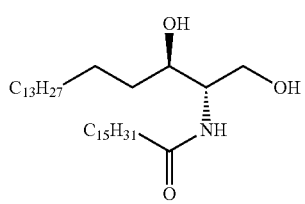

Compound F

SUMMARY OF THE INVENTION

The present invention provides novel synthetic approaches to preparing sphingomyelin which allow for large scale synthesis of relatively enantiomerically pure compounds. Specifically, the invention provides a method of preparing sphingomyelins having fatty acid change lengths of 12 to 25 carbons.

More specifically the invention provides a method for synthesizing N-Palmitoyl-D-erythro-trans-sphingosyl-phosphorylcholine starting from D-erythro-sphingosine. The invention also provides methods for the synthesis of D-erythro-sphingosine. The invention also provides a method for synthesizing N-Palmitoyl-D-erythro-dihydrosphingosyl-phosphorylcholine starting from D-erythro-dihydrosphingosine. The invention also provides methods for the synthesis of D-erythro-dihydrosphingosine. The invention also provides a method for synthesizing N-palmitoyl-D-erythro-sphingosine and N-palmitoyl-D-erythro-dihydrosphingosine, which.

The invention also provides for a method of synthesizing D-erythro-sphingosines on a kilogram scale. In a particular embodiment, the D-erythro-sphingosine is N-palmitoyl-D-erythro-sphingosine.

The invention also provides for a method of synthesizing D-erythro-dihydrosphingosines on a kilogram scale. In a particular embodiment, the D-erythro-sphingosine is N-palmitoyl-D-erythro-dihydrosphingosine.

In a particular embodiment, the invention provides a method for synthesizing D-erythro-sphingosine starting from L-serine methyl ester comprising the steps of:
a) protecting the amino group of an L-serine methyl ester or a salt thereof with a tert-butoxycarbonyl group, to yield Boc-L-Ser-OMe;
b) reacting Boc-L-Ser-OMe with 2,2-dimethoxypropane in the presence of benzenesulfonic acid to yield (S)-3-(tert-butoxycarbonyl)-2,2-dimethyl-4-oxazolidincarboxylic acid methylester;
c) reacting (S)-3-(tert-butoxycarbonyl)-2,2-dimethyl-4-oxazolidincarboxylic acid methylester with dimethyl methylphosphonate in the presence of n-butyllithium to yield (S)-3-(tert-butoxycarbonyl)-4-(2-(dimethoxyphosphoryl)-1-oxo-ethyl)-2,2-dimethyloxazolidine;
d) reacting (S)-3-(tert-butoxycarbonyl)-4-(2-(dimethoxyphosphoryl)-1-oxo-ethyl)-2,2-dimethyloxazolidine with 1-tetradecanal to yield (S)-3-(tert-butoxycarbonyl)-4-(1-oxo-hexadec-2-enyl)-2,2-dimethyloxazolidine;
e) stereo selectively reducing of the carbonyl group of (S)-3-(tert-butoxycarbonyl)-4-(1-oxo-hexadec-2-enyl)-2,2-dimethyloxazolidine with sodium borohydride and cerium trichloride, to yield (2S,3R,4E)-3-(tert-butoxycarbonyl)-4-(1-hydroxy-hexadec-2-enyl)-2,2-dimethyloxazolidine;
f) removing the tert-butoxycarbonyl (Boc) protecting group of (2S,3R,4E)-3-(tert-butoxycarbonyl)-4-(1-hydroxy-hexadec-2-enyl)-2,2-dimethyloxazolidine to yield D-erythro-sphingosine.

In yet another embodiment, the invention provides a method for synthesizing N-palmitoyl D-erythro-sphingosine starting from (1R,2R,5R)-(+)-2-hydroxy-3-pinanone, comprising the steps of:
a) reacting (1R,2R,5R)-(+)-2-hydroxy-3-pinanone with ethyl glycinate to afford ethyl 2-((E)-((1S,2S,5S)-2-hydroxy-2,6,6-trimethylbicyclo[3.1.1]heptan-3-ylidene)amino)acetate;
b) reacting ethyl 2-((E)-((1S,2S,5S)-2-hydroxy-2,6,6-trimethylbicyclo[3.1.1]heptan-3-ylidene)amino)acetate with 2-(E)-hexadecen-1-al to yield: (2S,3R,E)-ethyl 3-hydroxy-2-((E)-((1S,2S,5S)-2-hydroxy-2,6,6-trimethylbicyclo[3.1.1]heptan-3-ylidene)amino)octadec-4-enoate and (2S,3R,E)-propyl 3-hydroxy-2-((E)-((1S,2S,5S)-2-hydroxy-2,6,6-trimethylbicyclo[3.1.1]heptan-3-ylidene)amino)octadec-4-enoate;
c) hydrolyzing the (2S,3R,E)-ethyl 3-hydroxy-2-((E)-((1S,2S,5S)-2-hydroxy-2,6,6-trimethylbicyclo[3.1.1]heptan-3-ylidene)amino)octadec-4-enoate and (2S,3R,E)-propyl 3-hydroxy-2-((E)-((1S,2S,5S)-2-hydroxy-2,6,6-trimethylbicyclo[3.1.1]heptan-3-ylidene)amino)octadec-4-enoateto yield (2R,3R,E)-ethyl 2-amino-3-hydroxyoctadec-4-enoate and (2R,3R,E)-propyl 2-amino-3-hydroxyoctadec-4-enoate;
d) reducing (2R,3R,E)-ethyl 2-amino-3-hydroxyoctadec-4-enoate and (2R,3R,E)-propyl 2-amino-3-hydroxyoctadec-4-enoate to yield D-erythro-sphingosine;
e) reacting D-erythro-sphingosine with palmitic acid to yield N-palmitoyl-D-Erythro-sphingosine.

In yet another embodiment, the invention provides a method for synthesizing N-palmitoyl-sphingomyelin comprising the steps of:
a) acylating D-erythro-sphingosine with palmitic acid in the presence of O-Benzotriazole-N,N,N',N'-tetramethyl-uronium-hexafluoro-phosphate and triethylamine to yield N-palmitoyl-sphingosine
b) reacting N-palmitoyl-sphingosine with ethylene chlorophosphite to yield N-((2S,3R,E)-1-((1,3,2-dioxaphospholan-2-yl)oxy)-3-hydroxyoctadec-4-en-2-yl)palmitoylamide;
c) reacting N-((2S,3R,E)-1-((1,3,2-dioxaphospholan-2-yl)oxy)-3-hydroxyoctadec-4-en-2-yl)palmitoylamide with bromine to yield 2-bromoethyl ((2S,3R,E)-3-hydroxy-2-palmitamidooctadec-4-en-1-yl)phosphorobromidate;
d) hydrolyzing 2-bromoethyl ((2S,3R,E)-3-hydroxy-2-palmitamidooctadec-4-en-1-yl)phosphorobromidate to yield N-palmitoyl-sphingomyelin.

In still another embodiment, the invention provides a method for synthesizing N-palmitoyl-D-erythro-trans-sphingosylphosphorylcholine (N-palmitoyl-D-erythro-sphingomyelin) comprising the steps of:
a) reacting D-erythro-sphingosine with palmitic acid in the presence of O-benzotriazole-N,N,N',N'-tetramethyl-uronium-hexafluoro-phosphate and triethylamine to yield D-erythro-ceramide-C16 b) reacting D-erythro-ceramide-C16 with tritylchloride and pyridine to yield D-erythro-1-O-trityl-ceramide C16;

c) benzoylating D-etythro-1-O-trityl-ceramide-C16 to yield D-erythro-1-O-trityl-3-O-benzoyl-ceramide-C16;

d) removing the trityl group of D-erythro-1-O-trityl-3-O-benzoyl-ceramide-C16 in the presence of para-toluenesulfonic acid to yield D-erythro-3-O-benzoyl-ceramide-C16;

e) reacting D-erythro-3-O-benzoyl-ceramide-C16 with 2-chloro-2-oxo-1,3,2-dioxaphospholane to yield D-erythro-3-O-benzoyl-1-O-(2-oxo-1,3,2-dioxaphospholane) ceramide-C16;

f) reacting D-erythro-3-O-benzoyl-1-O-(2-oxo-1,3,2-dioxaphospholane) ceramide-C16 with trimethylamine to yield D-erythro-3-O-benzoyl-N-palmitoyl-sphingomyeline;

g) removing the benzoyl group of D-erythro-3-O-benzoyl-N-palmitoyl-sphingomyeline with sodium methoxide to yield N-palmitoyl-D-erythro-sphingomyelin.

In another embodiment, the invention provides a method for synthesizing an N-acyl-D-erythro-sphingomyelin comprising the steps of:

a) acylating D-erythro-sphingosine with a fatty acid;

b) protecting the primary hydroxyl group of the resulting D-erythro-ceramide with a trityl group to yield D-erythro-1-O-trityl-ceramide;

c) benzoylating the D-erythro-1-O-trityl-ceramide to protect the secondary hydroxyl group and yield D-erythro-1-O-trityl-3-O-benzoyl-ceramide;

d) removing the trityl group of D-erythro-1-O-trityl-3-O-benzoyl-ceramide to yield D-erthro-3-O-benzoyl-ceramide;

e) reacting D-erythro-3-O-benzoyl-ceramide with 2-chloro-2-oxo-1,3,2-dioxaphospholane to yield D-erythro-3-O-benzoyl-1-O-(2-oxo-1,3,2-dioxaphospholane) ceramide;

f) reacting D-erythro-3-O-benzoyl-1-O-(2-oxo-1,3,2-dioxaphospholane) ceramide with trimethylamine to yield the N-acyl D-erythro-3-O-benzoyl-sphingomyeline;

g) removing the benzoyl group of D-erythro-3-O-benzoyl-sphingomyelin with sodium methoxide to yield N-acyl D-erythro-sphingomyelin.

In yet another embodiment, the invention provides a method for synthesizing N-palmitoyl D-erythro-dihydrosphingosine starting from (1R,2R,5R)-(+)-2-hydroxy-3-pinanone, comprising the steps of:

a) reacting (1R,2R,5R)-(+)-2-hydroxy-3-pinanone with ethyl glycinate yield ethyl 2-(E-((1S,2S,5S)-2-hydroxy-2,6,6-trimethylbicyclo[3.1.1]heptan-3-ylidene)amino)acetate;

b) reacting ethyl 2-(E-((1S,2S,5S)-2-hydroxy-2,6,6-trimethylbicyclo[3.1.1]heptan-3-ylidene)amino)acetate and 1-hexadecanal to yield: (2S,3R,E)-ethyl 3-hydroxy-2-(((1S,2S,5S)-2-hydroxy-2,6,6-trimethylbicyclo[3.1.1]heptan-3-yl idene)amino)octadecanoate and/or (2S,3R,E)-propyl 3-hydroxy-2-(((1S,2S,5S)-2-hydroxy-2,6,6-trimethylbicyclo[3.1.1]heptan-3-ylidene)amino)octadecanoate;

c) hydrolyzing (2S,3R,E)-ethyl 3-hydroxy-2-(((1S,2S,5S)-2-hydroxy-2,6,6-trimethylbicyclo[3.1.1]heptan-3-ylidene)amino)octadecanoate and (2S,3R,E)-propyl 3-hydroxy-2-(((1S,2S,5S)-2-hydroxy-2,6,6-trimethylbicyclo[3.1.1]heptan-3-ylidene)amino)octadecanoate to yield (2R,3R,E)-ethyl 2-amino-3-hydroxyoctadecanoate and/or (2R,3R,E)-propyl 2-amino-3-hydroxyoctadecanoate;

d) reducing (2R,3R,E)-ethyl 2-amino-3-hydroxyoctadecanoate and (2R,3R,E)-propyl 2-amino-3-hydroxyoctadecanoate to yield D-erythro-dihydrosphingosine;

e) reacting D-erythro-dihydrosphingosine with palmitic acid to yield N-palmitoyl-D-Erythro-dihydrosphingosine.

In yet another embodiment, the invention provides a method for synthesizing N-palmitoyl D-erythro-dihydrosphingomyelin comprising the steps of:

a) reacting D-erythro-dihydrosphingosine with palmitic acid to yield N-palmitoyl-D-erythro-dihydrosphingosine;

b) protecting the primary hydroxyl group of N-palmitoyl-D-erythro-dihydrosphingosine with a trityl group to yield N-palmitoyl-D-erythro-1-O-trityl-dihydrosphingosine;

c) benzoylating the N-palmitoyl-D-erythro-1-O-trityl-d dihydrosphingosine to protect the secondary hydroxyl group and yield N-palmitoyl-D-erythro-1-O-trityl-3-O-benzoyl-dihydrosphingosine;

d) removing the trityl group of N-palmitoyl-D-erythro-1-O-trityl-3-O-benzoyl-dihydrosphingosine to yield N-palmitoyl-D-erythro-3-O-benzoyl-dihydrosphingosine;

e) reacting N-palmitoyl-D-erythro-3-O-benzoyl-dihydrosphingosine with 2-chloro-2-oxo-1,3,2-dioxaphospholane (CCP) to yield N-acyl-D-erythro-3-O-benzoyl-1-O-(2-oxo-1,3,2-dioxaphospholane)-dihydrosphingosine;

f) reacting N-palmitoyl-D-erythro-3-O-benzoyl-1-O-(2-oxo-1,3,2-dioxaphospholane)dihydrosphingosine with trimethylamine to yield the N-palmitoyl-D-erythro-3-O-benzoyl-dihydrosphingomyeline;

g) removing the benzoyl group of N-palmitoyl-D-erythro-3-O-benzoyl-dihydrosphingomyelin with sodium methoxide to yield N-palmitoyl-D-erythro-dihydrosphingomyelin.

In yet another embodiment, the invention provides a method for N-palmitoyl-D-erythro dihydrosphingomyelin comprising the steps of:

a) reacting D-erythro-dihydrosphingosine with palmitic acid in the presence of O-Benzotriazole-N,N,N',N'-tetramethyl-uronium-hexafluoro-phosphate and triethylamine to yield N-palmitoyl-D-erythro-dihydrosphingomyelin;

b) reacting N-palmitoyl-D-erythro-dihydrosphingomyelin with ethylene chlorophosphite to yield N-((2S,3R)-1-((1,3,2-dioxaphospholan-2-yl)oxy)-3-hydroxyoctadecan-2-yl)palmitamide;

c) reacting N-((2S,3R)-1-((1,3,2-dioxaphospholan-2-yl)oxy)-3-hydroxyoctadecan-2-yl)palmitamide with bromine to yield 2-bromoethyl ((2S,3R)-3-hydroxy-2-palmitamidooctadecyl)phosphorobromidate;

d) hydrolyzing 2-bromoethyl ((2S,3R)-3-hydroxy-2-palmitamidooctadecyl)phosphorobromidate to yield the N-palmitoyl-D-erythro dihydrosphingomyelin.

In yet another embodiment, the invention provides a method for synthesizing an N-acyl D-erythro-dihydrosphingomyelin comprising the steps of:

a) acylating D-erythro-dihydrosphingosine with a fatty acid to yield an N-acyl-D-erythro-dihydroceramide;

b) protecting the primary hydroxyl group N-acyl-D-erythro-dihydroceramide with a trityl group to yield N-acyl-D-erythro-1-O-trityl-dihydroceramide;

c) benzoylating the N-acyl-D-erythro-1-O-trityl-dihydroceramide to protect the secondary hydroxyl group and yield N-acyl-D-erythro-1-O-trityl-3-O-benzoyl-dihydroceramide;

d) removing the trityl group of N-acyl-D-erythro-1-O-trityl-3-O-benzoyl-dihydroceramide to yield N-acyl-D-erythro-3-O-benzoyl-dihydroceramide;

e) reacting N-acyl-D-erythro-3-O-benzoyl-dihydroceramide with 2-chloro-2-oxo-1,3,2-dioxaphospholane to yield N-acyl-D-erythro-3-O-benzoyl-1-O-(2-oxo-1,3,2-dioxaphospholane)-dihydroceramide;

f) reacting N-acyl-D-erythro-3-O-benzoyl-1-O-(2-oxo-1,3,2-dioxaphospholane)dihydroceramide with trimethylamine to yield the N-acyl-D-erythro-3-O-benzoyl-dihydrosphingomyeline;

g) removing the benzoyl group of N-acyl-D-erythro-3-O-benzoyl-dihydrosphingomyelin with sodium methoxide to yield N-acyl-D-erythro-dihydrosphingomyelin.

In yet another embodiment a fatty acid refers to, but is not limited to, one of the following:

a) an acid with an aliphatic tail of 10 to 24 carbons;

b) an acid with a hydrocarbon chain comprising 10 to 24 carbon atoms and one, two, three or four carbon-carbon double bonds;

c) an omega fatty acid such as ω-3, or ω-6, or ω-9;

d) cis- and trans-monounsaturated fatty acids such as, but not limited to, oleic acid and elaidic acid, respectively;

e) essential fatty acids, such as, but not limited to, linoleic acid (LA), α-linolenic acid (ALA), n-3 fatty acids, e.g. eicosapentaenoic acid (EPA) and docosahexaenoic acid (DHA).

DETAILED DESCRIPTION OF THE INVENTION

Figure 1:
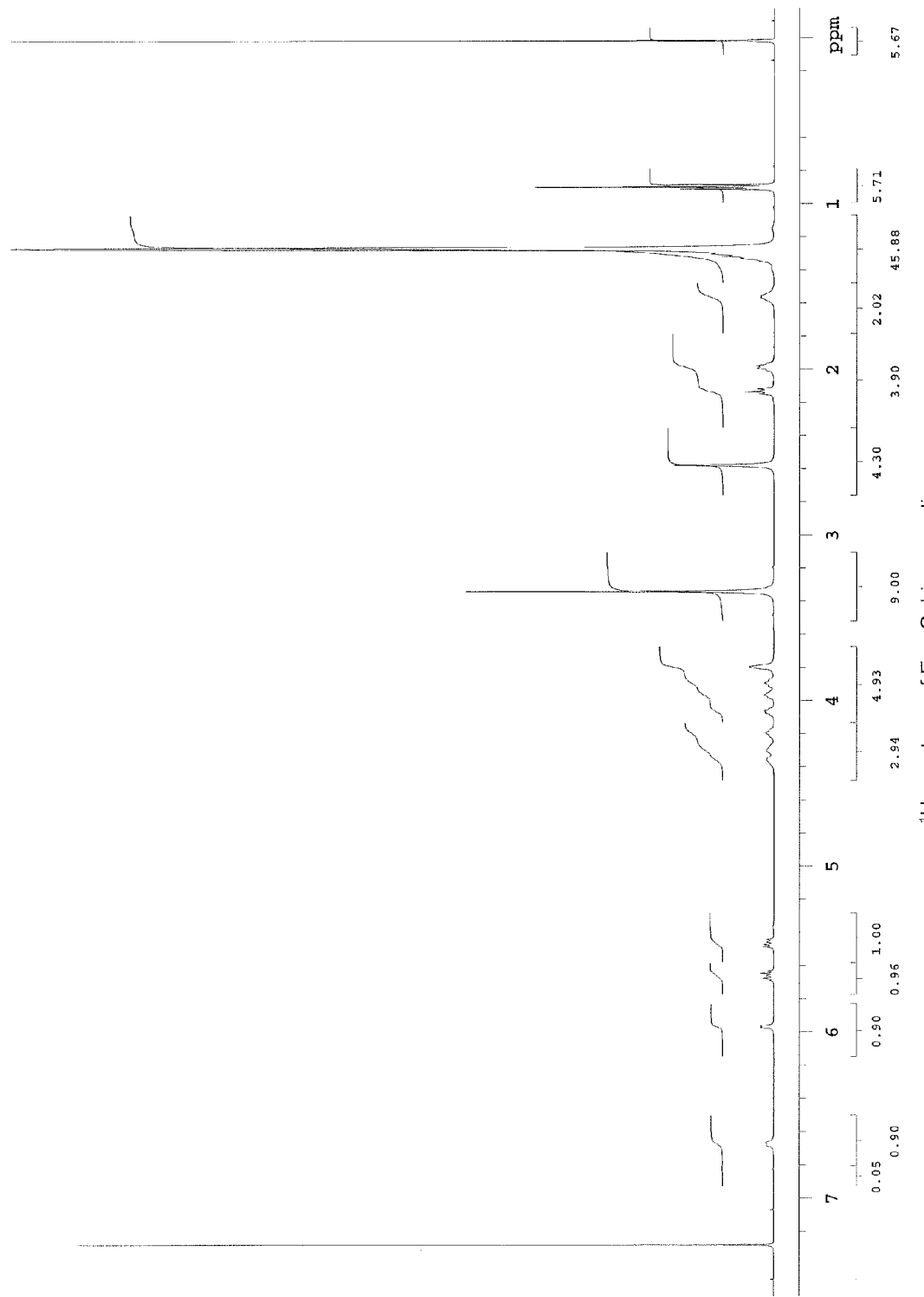
FIG. 1—The $^1$H NMR spectra for naturally occurring egg sphingomyelin.

The present invention provides a novel synthesis of an N-acyl D-erythro-sphingomyelin. In certain embodiments of the invention, the D-erythro-sphingomyelin is prepared at a large, commercially relevant scale, starting from a suitable L-serine ester (methyl, ethyl, i-propyl, n-butyl, etc.). The method of the present invention is suitable for the synthesis of D-erythro-sphingomyelin.

The present invention also provides a novel synthesis for the synthesis of D-erythro-sphingosine.

The invention also includes compounds synthesized by the methods described herein, including compounds synthesized as intermediates.

As discussed above, sphingomyelins consist of a ceramide core bound to a polar head group.

A ceramide core consists of a sphingosine bound to a fatty acid via an amide linkage. It is to be understood that, if the term "ceramide-Cn" is used, where n is an integer, n refers to the number of carbons in the fatty acid, e.g. ceramide-C16 refers to a ceramide core with a 16 carbon fatty acid residue, such as palmitoyl; ceramide C18 refers to a ceramide core with a 18 carbon fatty acid residue, such as stearoyl.

If "ceramide" or "ceramide core" is used without specifying the length of the fatty acid carbon chain, it is to be understood that the fatty acid chain carbon could be any suitable length.

It is to be understood that for the purposes of the present invention, the term sphingomyelin describes a ceramide core bound to a phosphorylcholine functional group. Therefore, it is to be understood that sphingomyelin and sphingophosphorylcholine may be used interchangeably.

A fatty acid is a carboxylic acid with a long aliphatic tail that can be either saturated or unsaturated. Unsaturated fatty acids have one or more carbon-carbon double bonds between carbon atoms and the two carbon atoms next to either side of the carbon-carbon double bond can occur in a cis or trans configuration. A fatty acid residue is a fatty acid less the —OH group of the fatty acid's carboxyl group.

In certain embodiments of the invention the fatty acid or fatty acid residue contains 3 to 36 carbons and optionally, one to four carbon-carbon double bonds. In particular embodiments of the invention the fatty acid or fatty acid residue contains 4 to 28 carbons and optionally, one to four carbon-carbon double bonds. In further embodiments of the invention, the fatty acid or fatty acid residue contains 11 to 25 carbons and zero to four carbon-carbon double bonds. In still further embodiments of the invention, the fatty acid or fatty acid residue contains 11 to 25 carbons and one or two carbon-carbon double bonds. In further embodiments of the invention, the fatty acid or fatty acid residue contains 14 to 20 carbons and zero to four carbon-carbon double bonds. In yet further embodiments of the invention, the fatty acid or fatty acid residue contains 15 to 17 carbons and zero to four carbon-carbon double bonds. In a particular embodiment of the invention, the fatty acid is palmitic acid.

Suitable fatty acids also include, but are not limited to, omega fatty acids such as ω-3, or ω-6, or ω-9; and essential fatty acids, such as, but not limited to, linoleic acid (LA), ω-linolenic acid (ALA), n-3 fatty acids, e.g. eicosapentaenoic acid (EPA) and docosahexaenoic acid (DHA).

Suitable fatty acids useful in the present invention include, but are not limited to, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, myristoleic acid, palmitoleic acid, sapienic acid, oleic acid, elaidic acid, vaccenic acid, linoleic acid, linoelaidic acid, α-linolenic acid, and erucic acid.

If the fatty acid is a monounsaturated fatty acid, it can be in either the cis- or trans-monounsaturated fatty acids such as, but not limited to, oleic acid and elaidic acid, respectively.

Certain compounds of the invention can be in the form of a salt. In some embodiments, the salt is a pharmaceutically acceptable salt. Pharmaceutically acceptable salts include, for example, acid-addition salts and base-addition salts. The acid that forms an acid-addition salt can be an organic acid or an inorganic acid. A base that forms a base-addition salt can be an organic base or an inorganic base. In some embodiments, a pharmaceutically acceptable salt is a metal salt. In some embodiments, a pharmaceutically acceptable salt is an ammonium salt.

Acid-addition salts can arise from the addition of an acid to the free-base form of a compound of the invention. In some embodiments, the acid is organic. In some embodiments, the acid is inorganic. Non-limiting examples of suitable acids include hydrochloric acid, hydrobromic acid, hydroiodic acid, nitric acid, nitrous acid, sulfuric acid, sulfurous acid, a phosphoric acid, nicotinic acid, isonicotinic acid, lactic acid, salicylic acid, 4-aminosalicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, citric acid, oxalic acid, maleic acid, hydroxymaleic acid, methylmaleic acid, glycolic acid, malic acid, cinnamic acid, mandelic acid, 2-phenoxybenzoic acid, 2-acetoxybenzoic acid, embonic acid, phenylacetic acid, N-cyclohexylsulfamic acid, methanesulfonic acid, ethanesulfonic acid, benzenesulfonic acid, p-toluenesulfonic acid, 2-hydroxyethanesulfonic acid, ethane-1,2-disulfonic acid, 4-methylbenzenesulfonic acid, naphthalene-2-sulfonic acid, naphthalene-1,5-disulfonic acid, 2-phosphoglyceric acid, 3-phosphoglyceric acid, glucose-6-phosphoric acid, and an amino acid.

Non-limiting examples of suitable acid-addition salts include a hydrochloride salt, a hydrobromide salt, a hydroiodide salt, a nitrate salt, a nitrite salt, a sulfate salt, a sulfite salt, a phosphate salt, a hydrogen phosphate salt, a dihydrogen phosphate salt, a carbonate salt, a bicarbonate salt, a nicotinate salt, an isonicotinate salt, a lactate salt, a salicylate salt, a 4-aminosalicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a citrate salt, an oxalate salt, a maleate salt, a hydroxymaleate salt, a methylmaleate salt, a glycolate salt, a malate salt, a cinnamate salt, a mandelate salt, a 2-phenoxybenzoate salt, a 2-acetoxybenzoate salt, an embonate salt, a phenylacetate salt, an N-cyclohexylsulfamate salt, a methanesulfonate salt, an ethanesulfonate salt, a benzenesulfonate salt, a p-toluenesulfonate salt, a 2-hydroxyethanesulfonate salt, an ethane-1,2-disulfonate salt, a 4-methylbenzenesulfonate salt, a naphthalene-2-sulfonate salt, a naphthalene-1,5-disulfonate salt, a 2-phosphoglycerate salt, a 3-phosphoglycerate salt, a glucose-6-phosphate salt, and an amino acid salt.

Metal salts can arise from the addition of an inorganic base to a compound of the invention having a carboxyl group. The inorganic base consists of a metal cation paired with a basic couterion, such as, for example, hydroxide, carbonate, bicarbonate, or phosphate. The metal can be an alkali metal, alkaline earth metal, transition metal, or main group metal. Non-limiting examples of suitable metals include lithium, sodium, potassium, cesium, cerium, magnesium, manganese, iron, calcium, strontium, cobalt, titanium, aluminum, copper, cadmium, and zinc.

Non-limiting examples of suitable metal salts include a lithium salt, a sodium salt, a potassium salt, a cesium salt, a cerium salt, a magnesium salt, a manganese salt, an iron salt, a calcium salt, a strontium salt, a cobalt salt, a titanium salt, a aluminum salt, a copper salt, a cadmium salt, and a zinc salt.

Ammonium salts can arise from the addition of ammonia or an organic amine to a compound of the invention having a carboxyl group. Non-limiting examples of suitable organic amines include triethyl amine, diisopropyl amine, ethanol amine, diethanol amine, triethanol amine, morpholine, N-methylmorpholine, piperidine, N-methylpiperidine, N-ethylpiperidine, dibenzyl amine, piperazine, pyridine, pyrrazole, imidazole, pyrazine, pipyrazine, ethylenediamine, N,N'-dibenzylethylene diamine, procaine, chloroprocaine, choline, dicyclohexyl amine, and N-methylglucamine.

Non-limiting examples of suitable ammonium salts include is a triethylammonium salt, a diisopropylammonium salt, an ethanolammonium salt, a diethanolammonium salt, a triethanolammonium salt, a morpholinium salt, an N-methylmorpholinium salt, a piperidinium salt, an N-methylpiperidinium salt, an N-ethylpiperidinium salt, a dibenzylammonium salt, a piperazinium salt, a pyridinium salt, a pyrazolium salt, an imidazolium salt, a pyrazinium salt, an ethylenediammonium salt, an N,N'-dibenzylethylenediammonium salt, a procaine salt, a chloroprocaine salt, a choline salt, a dicyclohexylammonium salt, and a N-methylglucamine salt.

General Methods

D-Erythro-Sphingosine from a L-Serine Ester

In a particular embodiment, the invention provides for a method of synthesizing D-erythro-sphingosine from a L-serine ester, such as that of Compound Ia in Scheme I, where R is C1-5 alkyl group. The term "alkyl," as used herein unless otherwise defined, refers to a straight, branched, or cyclic saturated group derived form the removal of a hydrogen atom from an alkane. Representative straight chain alkyl groups include -methyl, -ethyl, -n-propyl, -n-butyl, and -n-pentyl. Representative branched alkyl groups include -isopropyl, -sec-butyl, -isobutyl, -tert-butyl, -isopentyl, -neopentyl, 1-methylbutyl, 2-methylbutyl, 3-methylbutyl, 1,1-dimethylpropyl and 1,2-dimethylpropyl. Representative cyclic alkyl groups include cyclopentyl, and cyclopropyl.

In certain embodiments of the invention, the L-serine ester is L-serine methyl ester. In another embodiment, the L-serine ester is L-serine ethyl ester. In yet another embodiment, the L-serine ester is L-butyl ester In one embodiment of the invention D-erythro-sphingosine is synthesized by the method shown in Scheme I which comprises the following steps:

a) protecting the amino group of a L-serine ester (Compound Ia) with tert-butoxycarbonyl, resulting in a Boc-protected L-serine ester (Compound Ib);
b) transforming the Boc-protected L-serine ester into (S)-3-(tert-butoxycarbonyl)-2,2-dimethyl-4-oxazolidincarboxylic acid ester (Compound Ic) with 2,2-dimethoxypropane through benzenesulfonic acid catalysis;
c) reacting (S)-3-(tert-butoxycarbonyl)-2,2-dimethyl-4-oxazolidincarboxylic acid ester with dimethyl methylphosphonate and n-butyllithium to yield (S)-3-(tert-butoxycarbonyll)-4-(2-(dimethoxy-phosphoryl)-1-oxo-ethyl)-2,2-dimethyloxazolidine (Compound Id);
d) reacting (S)-3-(tert-butoxycarbonyl)-4-(2-(dimethoxy-phosphoryl)-1-oxo-ethyl)-2,2-dimethyloxazolidine with 1-tetradecanal to yield (S)-3-(tert-butoxycarbonyl)-4-(1-oxo-hexadec-2-enyl)-2,2-dimethyloxazolidine (Compound Ie);
e) performing stereoselective reduction of the carbonyl group of (S)-3-(tert-butoxycarbonyl)-4-(1-oxo-hexadec-2-enyl)-2,2-dimethyloxazolidine with sodium borohydride and cerium trichloride, to form (2S,3R,4E)-3-(tert-butoxycarbonyl)-4-(1-hydroxy-hexadec-2-enyl)-2,2-dimethyloxazolidine (Compound If);
f) removing the tert-butoxycarbonyl (Boc) protecting group of (2S,3R,4E)-3-(tert-butoxycarbonyl)-4-(1-hydroxy-hexadec-2-enyl)-2,2-dimethyloxazolidine and purifying the resulting D-erythro-sphingosine (Compound A).

Scheme 1

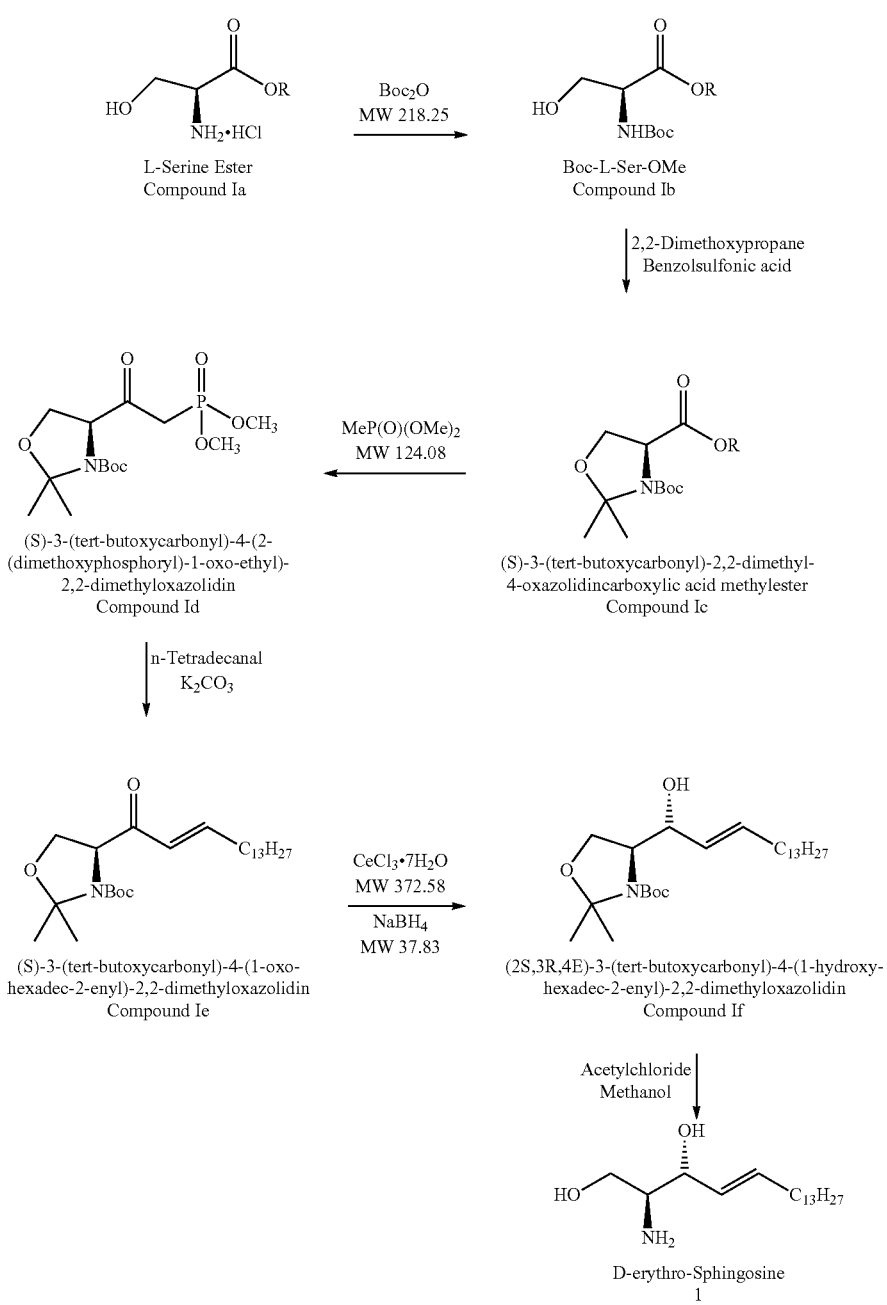

In one aspect of the invention, the amino group of the L-serine ester (Compound Ia of Scheme I) is protected with tert-butoxycarbonyl (Boc) in the presence of a base to yield Boc-protected L-serine ester (Compound Ib). The reaction can then be quenched with the addition of water and the reaction product recovered from the organic layer. The addition of the Boc protecting group proceeds in an aprotic organic solvent at a temperature of about 22° C. for about 6 to 24 hours. In one embodiment, the aprotic organic solvent is chlorinated and is methylene chloride, chloroform or carbon tetrachloride. In another embodiment, the aprotic organic solvent is nonchlorinated and is diethyl ether, tetrahydrofuran, or ethyl acetate. The base is typically an organic base, such as triethylamine or pyridine. The reaction product can be extracted from the organic layer with an organic solvent, including, but not limited to, an aprotic organic solvent described above.

In another aspect of the invention the Boc-protected L-serine ester (Compound Ib) is reacted with 2,2-dimethoxypropane in the presence of benzenesulfonic acid to yield the (S)-3-(tert-butoxycarbonyl)-2,2-dimethyl-4-oxazolidincarboxylic acid ester (Compound Ic). The reaction proceeds at reflux for 1-3 hours in an organic solvent. In one embodiment, organic solvent is non-polar and is toluene, benzene or hexane. In another embodiment, organic solvent is a polar organic and is diethyl ether, tetrahydrofuran, or ethyl acetate. The reaction can then be neutralized with a base and the solvent evaporated. Water and an organic solvent can then be added to the remaining residue and the reaction product can be extracted from the organic layer with an organic solvent. The base is typically an organic base, such as triethylamine or pyridine. The reaction product can be extracted from the organic layer with an organic solvent, including, but not limited to the organic solvents described above.

In another aspect of the invention, (S)-3-(tert-butoxycarbonyl)-2,2-dimethyl-4-oxazolidincarboxylic acid ester (Compound Ic) is reacted with dimethyl methylphosphonate in the presence of n-butyllithium to yield (S)-3-(tert-butoxycarbonyl)-4-(2-(dimethoxyphosphoryl)-1-oxo-ethyl)-2,2-dimethyloxazolidin (Compound Id). The reaction can be quenched with water and the pH adjusted by the addition of an organic acid. The product can be recovered from the organic phase. The reaction proceeds in an organic solvent at a temperature of about −70 to −80° C. for about 2 to 4 hours. In certain embodiments, the organic solvent is a polar organic and is diethyl ether, tetrahydrofuran, or ethyl acetate. In certain embodiments the acid is citric acid or acetic acid.

In a further embodiment of the invention, (S)-3-(tert-butoxycarbonyl)-4-(2-(dimethoxyphosphoryl)-1-oxo-ethyl)-2,2-dimethyloxazolidin (Compound Id) and potassium carbonate are stirred in an organic solvent at about 22° C., followed by the addition of tetradecanal and water. The reaction proceeds for 8-14 hours with stirring. The product (S)-3-(tert-butoxycarbonyl)-4-(1-oxo-hexadec-2-enyl)-2,2-dimethyloxazolidin (Compound Ie) can be recovered from the organic phase. In certain embodiments, the organic solvent is a polar organic and is acetonitrile, tetrahydrofuran, or ethyl acetate.

In yet another embodiment of the invention, (S)-3-(tert-butoxycarbonyl)-4-(1-oxo-hexadec-2-enyl)-2,2-dimethyloxazolidin (Compound Ie) and cerium chloride heptahydrate are stirred in an organic solvent and the mixture is cooled to −20 to −15° C. Sodium aborohydride is added to the mixture over 1 to 6 hours. After addition of the sodium borohydride, the reaction proceeds for 15 to 90 minutes, at which point it is warmed to about 22° C. over 1 to 3 hours. After reaching 22° C., the mixture is stirred for 30 to 90 minutes. In one embodiment the organic solvent is a protic polar solvent and is methanol, ethanol, n-propanol, or isopropanol. In certain embodiments the sodium borohydride is added as a solid. In other embodiments, the sodium borohydride is added as an aqueous solution. In certain embodiments of the invention at least some of the solvent is removed through evaporation and the precipitated salts are filtered and washed with an organic solvent. The product, (2S,3R,4E)-3-(tert-butoxycarbonyl)-4-(1-hydroxy-hexadec-2-enyl)-2,2-dimethyloxazolidin (Compound If), can be recovered from the organic phase of the resulting filtrate.

In a certain embodiment of the invention (2S,3R,4E)-3-(tert-butoxycarbonyl)-4-(1-hydroxy-hexadec-2-enyl)-2,2-dimethyloxazolidin (Compound If) is converted to D-erythro-sphingosine. The reaction proceeds as follows: methanol is cooled to about 0° C. and acetylchloride is added over the course of about 15 to 60 minutes. The solution is then warmed to produce a methanolic hydrochloride solution. (2S,3R,4E)-3-(tert-butoxycarbonyl)-4-(1-hydroxy-hexadec-2-enyl)-2,2-dimethyloxazolidin) is dissolved in methanol and the methanolic hydrochloride solution is added over the course of about 15 to 60 minutes. The reaction can be neutralized with the addition of a base. The solvent can then be removed and the resulting D-erythro-sphingosine can be recovered from the residue. The base can be an organic base, such as, but not limited to, triethylamine or pyridine.

In certain embodiments of the invention the benzoyl-protected D-erythro-sphingomyelin can be purified by recrystallization, silica gel chromatography, high performance liquid chromatography or other methods known to those skilled in the art.

A particular embodiment of the invention also provides for a method of synthesizing D-erythro-sphingosine from L-serine methyl ester.

In a particular embodiment of the invention Boc-L-Ser-OMe.HCl (Compound Ia, R=methyl) is suspended in ethyl acetate and cooled to about 2° C., about 1.15 molar equivalents of triethylamine is added, followed by about 1.15 molar equivalents of di-tert-butyl dicarbonate in ethyl acetate. The reaction mixture is warmed to about 22° C. and stirred for 8 to 12 hours. Purified water is added and the phases separated. The reaction product can be extracted with ethyl acetate from the organic layer and the resulting fractions dried in vacuo.

In a particular embodiment of the invention Boc-L-Ser-OMe.HCl (Compound Ib, R=methyl) is dissolved in tetrahydrofuran and 3-4 equivalents of 2,2-dimethoxypropane is added, followed by a solution of about 0.10 equivalents of benzenesulfonic acid in tetrahydrofuran and the reaction heated to reflux while some of tetrahydrofuran distilled off. The reaction is neutralized to pH 6.5 with triethylamine at about 22 C. The solvent is distilled off and water and hexane are added. The reaction product, (S)-3-(tert-butoxycarbonyl)-2,2-dimethyl-4-oxazolidincarboxylic acid methylester (Compound Ic, R=methyl), can be isolated from the hexane layer.

In another aspect of the invention, 2 equivalents of dimethyl methylphosphonate is dissolved in tetrahydrofuran and the mixture cooled to about −70 to −80° C. About 2 equivalents of n-butyllithium in heptane is added over the course of 1 to 3 hours while the mixture is kept at about −70 to −80° C. After stirring for about 1 hour, 1 equivalent of (S)-3-(tert-butoxycarbonyl)-2,2-dimethyl-4-oxazolidincarboxylic acid methylester in tetrahydrofuran is added over the course of 30 to 90 minutes while the mixture is kept at about −70 to −80° C. The mixture was warmed to about 0° C. over the course of 30 to 60 minutes and then stirred for 15 to 60 minutes. The reaction was quenched with the addition of water in tetrahydrofuran and the pH adjusted to pH 6-7 with the addition of a citric acid solution. An organic solvent, such as but not limited to ethyl acetate or diethyl ether, is added and the product, (S)-3-(tert-butoxycarbonyl)-4-(2-(dimethoxyphosphoryl)-1-oxo-ethyl)-2,2-dimethyloxazolidin, recovered from the organic layer.

In a further aspect of the invention, 1 equivalent of (S)-3-(tert-butoxycarbonyl)-4-(2-(dimethoxyphosphoryl)-1-oxo-ethyl)-2,2-dimethyloxazolidin (Compound Id) and about 2 equivalents of potassium carbonate are stirred in acetonitrile at about 22° C., followed by the addition of about 0.5 equivalents of 1-tetradecanal and water. The reaction proceeds for 8-14 hours with stirring. The salts are filtered off and washed with hexane and the product, (S)-3-(tert-butoxycarbonyl)-4-(1-oxo-hexadec-2-enyl)-2,2-dimethyloxazolidin (Compound Ie) is recovered from the organic phase.

In a still further aspect of the invention, 1 equivalent of (S)-3-(tert-butoxycarbonyl)-4-(1-oxo-hexadec-2-enyl)-2,2-dimethyloxazolidin (Compound Ie) and about 1.1 to 1.5 equivalents of cerium chloride heptahydrate are stirred in methanol and the mixture is cooled to −20 to −15° C. An aqueous solution of about 1.5 equivalents of sodium borohydride in about 30% caustic soda is cooled to about 0° C. and added to the (S)-3-(tert-butoxycarbonyl)-4-(1-oxo-hexadec-2-enyl)-2,2-dimethyloxazolidin mixture over the course of about 4 to 6 hours. After about 15 to 60 minutes of additional stirring the mixture is heated to about 22° C. over the course of 1 to 3 hours, followed by stirring for 30 to 90 minutes. Some of the methanol is distilled off and the precipitated salts are washed with an organic solvent, such as toluene. The product, (2S,3R,4E)-3-(tert-butoxycarbonyl)-4-(1-hydroxy-hexadec-2-enyl)-2,2-dimethyloxazolidin (Compound If), is recovered from the organic layer of the filtrate.

In a certain embodiment of the invention (2S,3R,4E)-3-(tert-butoxycarbonyl)-4-(1-hydroxy-hexadec-2-enyl)-2,2-dimethyloxazolidin (Compound If) is converted to D-erythro-sphingosine. The reaction proceeds as follows: methanol is cooled to about 0° C. and about 2 equivalents of acetylchloride are added over the course of about 15 to 60 minutes. The solution is then warmed to produce a methanolic hydrochloride solution. (2S,3R,4E)-3-(tert-butoxycarbonyl)-4-(1-hydroxy-hexadec-2-enyl)-2,2-dimethyloxazolidin) is dissolved in methanol and the methanolic hydrochloride solution is added over the course of about 15 to 60 minutes. The reaction is neutralized with the addition of triethylamine. The solvent can then be removed and the resulting D-erythro-sphingosine can be recovered from the residue.

D-erythro-dihydrosphingosine from a L-serine Ester

In a particular embodiment, the invention provides for a method of synthesizing D-erythro-dihydrosphingosine from a suitable L-serine ester, such as that of Compound Ia in Scheme II, where R is an alkyl group containing 1 to 5 carbons. The term "alkyl," as used herein unless otherwise defined, refers to a straight, branched, or cyclic saturated group derived form the removal of a hydrogen atom from an alkane. Representative straight chain alkyl groups include -methyl, -ethyl, -n-propyl, -n-butyl, -n-pentyl, and n-heptyl. Representative branched alkyl groups include -isopropyl, -sec-butyl, -isobutyl, -tert-butyl, -isopentyl, -neopentyl, 1-methylbutyl, 2-methylbutyl, 3-methylbutyl, 1,1-dimethylpropyl and 1,2-dimethylpropyl. Representative cyclic alkyl groups include cyclohexyl, cyclopentyl, and cyclopropyl.

In certain embodiments of the invention, the L-serine ester is L-serine methyl ester. In another embodiment, the L-serine ester is L-serine ethyl ester. In yet another embodiment, the L-serine ester is L-serine butyl ester.

In one embodiment of the invention D-erythro-dihydrosphingosine is synthesized by the method shown in Scheme II. The reaction proceeds from Compound If which comprises the following steps:

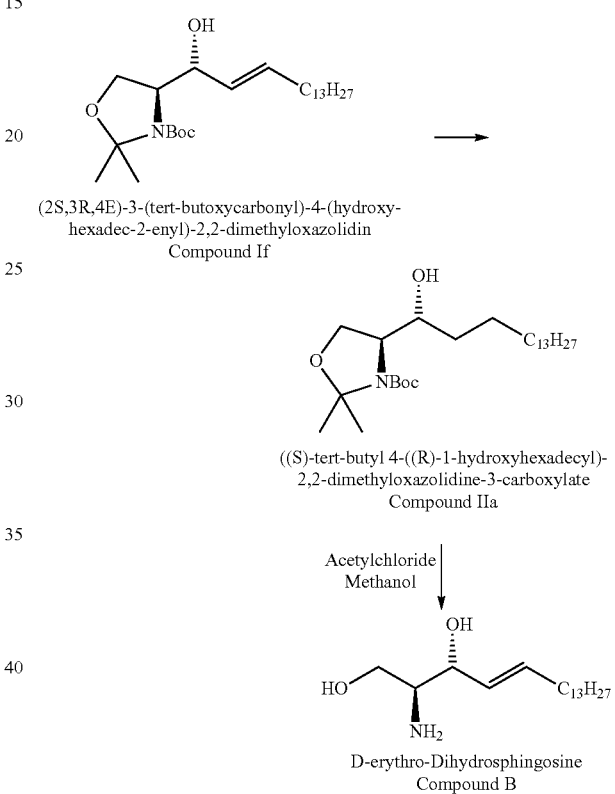

Scheme II (2S,3R,4E)-3-(tert-butoxycarbonyl)-4-(hydroxy-hexadec-2-enyl)-2,2-dimethyloxazolidin
Compound If ((S)-tert-butyl 4-((R)-1-hydroxyhexadecyl)-2,2-dimethyloxazolidine-3-carboxylate
Compound IIa Acetylchloride
Methanol D-erythro-Dihydrosphingosine
Compound B Compound If is reacted with a reducing agent to afford its saturated congener Compound IIa. The reaction is performed in an organic solvent such as, but not limited to, a primary or secondary alcohol, in the presence of ruthenium (II) catalysts, such as Ru(OAc)2(BINAP), [{RuCl(μ-Cl)(η$^6$-C$_6$Me$_6$)}$_2$], or Ru(OH)x/Al$_2$O$_3$.

In a particular embodiment, Compound If is reacted with isopropylalcohol at 82° C. in the presence of [{RuCl(μ-Cl)(η$^6$-C$_6$Me$_6$)}$_2$] at reflux. The reaction mixture is quenched and subjected to work-up when no more starting allyl alcohol IIa is detected by using a method well known to a person skilled in the art, such as, but not limited to, HPLC, thin-layer chromatography, IR.

Compound IIa thus obtained, either crude or purified, is dissolved in methanol at about 0° C., and acetylcholoride is added over about 15 to 60 minutes. When no more starting material (or no more conversion) is detected by a method such as a chromatography method, the reaction is treated with a base, which can be an organic base, such as, but not limited to, triethylamine or pyridine, or an inorganic base in aqueous solution, such as bicarbonates or carbonates of sodium, potassium, calcium, magnesium and ammonium. Further, the organic fraction is extracted with a solvent, such as a chlorinated solvent, ethyl acetate or an ether, such as diethyl ether, THF, t-butyl methyl ether, isopropyl ether, etc. The solvent is then removed and the resulting D-erythro-dihydrosphingosine is recovered as a free base. The base can be treated with hydrochloric acid to produce the hydrochloride.

D-erythro-sphingosine from pinanone

In another embodiment, the invention provides a method for synthesizing N-palmitoyl-D-Erythro-sphingosine from (1R,2R,5R)-(+)-2-hydroxy-3-pinanone as shown in Scheme III.

In yet another embodiment, the invention provides a method for synthesizing N-palmitoyl D-erythro-sphingosine starting from (1R,2R,5R)-(+)-2-hydroxy-3-pinanone, comprising the steps of:
a) reacting (1R,2R,5R)-(+)-2-hydroxy-3-pinanone (Compound IIIa) with ethyl glycinate to afford the corresponding pinanone iminoglycinate, namely ethyl 2-((E)-(1S,2S,5S)-2-hydroxy-2,6,6-trimethylbicyclo[3.1.1]heptan-3-ylidene)amino)acetate (Compound IIIb);
b) condensing the pinanone iminoglycinate above with 2-(E)-hexadecen-1-al to yield a mixture of the corresponding "pinanone aldols": (2S,3R,E)-ethyl 3-hydroxy-2-((E)-((1S,2S,5S)-2-hydroxy-2,6,6-trimethyl-bicyclo[3.1.1]heptan-3-ylidene)amino)octadec-4-enoate and (2S,3R,E)-propyl 3-hydroxy-2-((E)-((1S,2S,5S)-2-hydroxy-2,6,6-trimethylbicyclo[3.1.1]heptan-3-ylidene)amino)octadec-4-enoate (Compounds IIIc and IIIc');
c) hydrolyzing the "pinanone aldols" above to produce a mixture of (2R,3R,E)-ethyl 2-amino-3-hydroxyoctadec-4-enoate and (2R,3R,E)-propyl 2-amino-3-hydroxyoctadec-4-enoate (Compounds IIId and IIId');
d) reducing the esters (2R,3R,E)-ethyl 2-amino-3-hydroxyoctadec-4-enoate and (2R,3R,E)-propyl 2-amino-3-hydroxyoctadec-4-enoate with nascent hydrogen (sodium borohydride or equivalent) to yield D-erythrosphingosine;
e) reacting D-erythro-sphingosine with palmitic acid to afford N-palmitoyl-D-erythro-sphingosine.

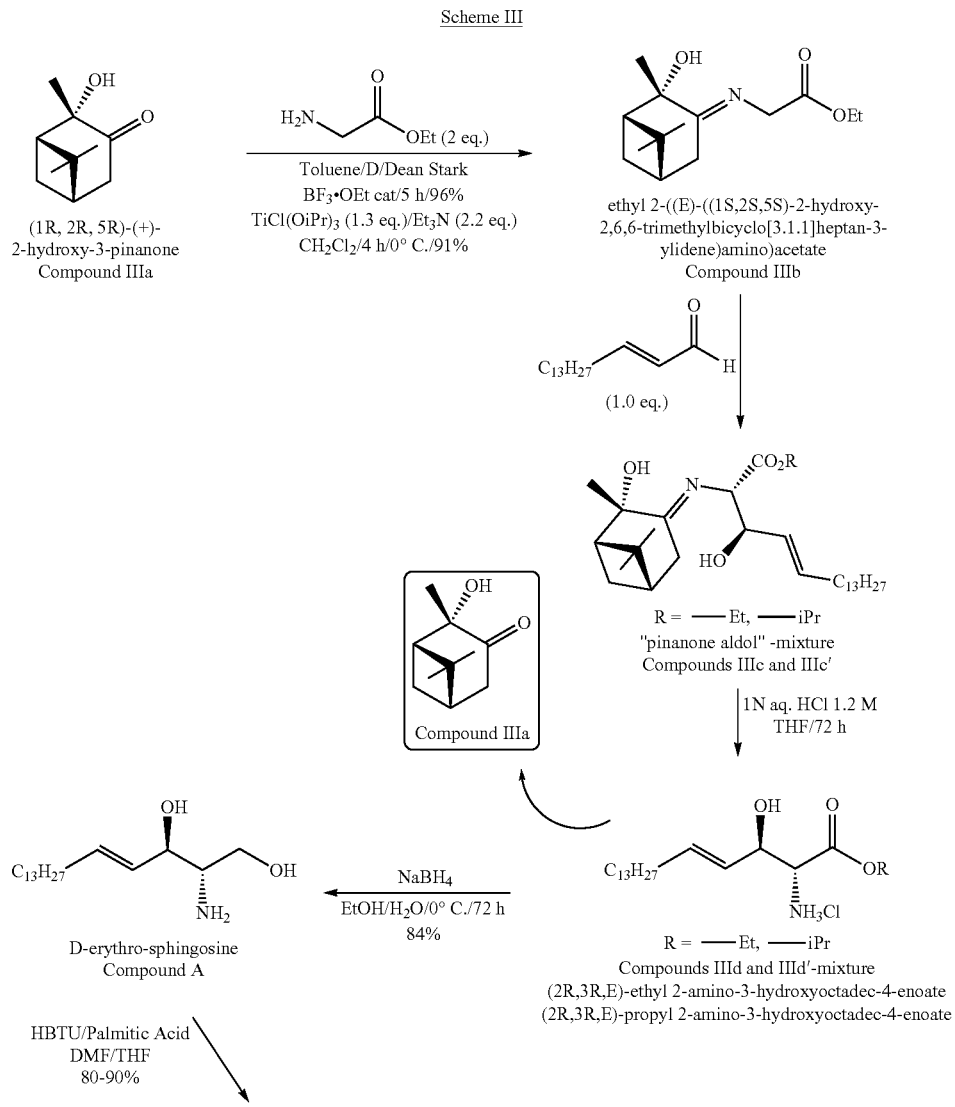

Scheme III

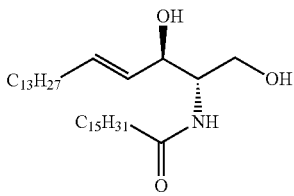

N-palmitoyl-D-Erythro-Sphingosine
Compound E

D-erythro-dihydrosphingosine from pinanone

In yet another embodiment, the invention provides a method for synthesizing D-erythro-dihydrosphingosine from (1R,2R,5R)-(+)-2-hydroxy-3-pinanone as shown in Scheme IV, and comprises the following steps:

a) reacting (1R,2R,5R)-(+)-2-hydroxy-3-pinanone with ethyl glycinate to afford the corresponding pinanone iminoglycinate, namely ethyl 2-(E-((1S,2S,5S)-2-hydroxy-2,6,6-trimethylbicyclo[3.1.1]heptan-3-ylidene)amino)acetate;

b) condensing the pinanone iminoglycinate above with 1-hexadecanal to yield a mixture of the corresponding "pinanone aldols": (2S,3R,E)-ethyl 3-hydroxy-2-(((1S,2S,5S)-2-hydroxy-2,6,6-trimethylbicyclo[3.1.1]heptan-3-ylidene)amino)octadecanoate and (2S,3R,E)-propyl 3-hydroxy-2-(((1S,2S,5S)-2-hydroxy-2,6,6-trimethylbicyclo[3.1.1]heptan-3-ylidene)amino)octadecanoate (Compounds IVc and IVc');

c) hydrolyzing the "pinanone aldols" above to produce a mixture of (2R,3R,E)-ethyl 2-amino-3-hydroxyoctadecanoate and (2R,3R,E)-propyl 2-amino-3-hydroxyoctadecanoate (Compound IVd and IVd');

d) reducing the ester (2R,3R,E)-ethyl 2-amino-3-hydroxyoctadecanoate with nascent hydrogen (sodium borohydride or equivalent) to yield D-erythro-dihydrosphingosine (Compound IVe);

e) reacting D-erythro-dihydrosphingosine with palmitic acid to afford N-palmitoyl-D-Erythro-dihydrosphingosine.

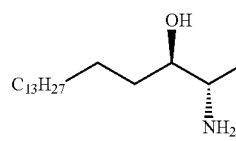 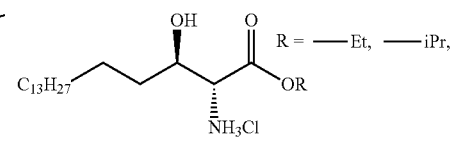

D-erythro-dihydroxysphingosine

Compound B

Compounds IVd annd IVd' mixture of
(2R,3R,E)-ethyl 2-amino-3-hydroxyoctadecanoate
(2R,3R,E)-propyl 2-amino-3-hydroxyoctadecanoate HBTU/Palmitic Acid
DMF/THF
80-90%

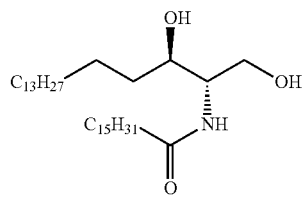

N-palmitoyl-D-Erythro-dihydroxyphingosine

Compound F

Synthesis of N-acyl D-erythro-sphingomyelin from D-erythro-sphingosine and a Fatty Acid In a further embodiment, the invention provides a method for synthesizing a D-erythro-sphingomyelin starting from D-erythro-sphingosine and a suitable fatty acid as shown in Scheme V comprising the steps of:

a) acylating D-erythro-sphingosine with a suitable fatty acid (Compound Va) to yield an D-erythro-ceramide Vb;
b) protecting the primary hydroxyl group of the D-erythro-ceramide Vb with a first protection group to yield Compound Vc;
c) protecting the secondary hydroxyl group of the D-erythro-ceramide with a second protection group yield to yield Compound Vd;
d) removing the first protecting group of Compound Vd to yield Compound Ve;
e) reacting Compound Ve with 2-chloro-2-oxo-1,3,2-dioxaphospholane (CCP) to yield Compound Vf;
f) reacting Compound Vf with trimethylamine to yield Compound Vg;
g) removing the second protecting group of Compound Vg with sodium methoxide to yield the D-erythro-sphingomyelin.

Scheme V

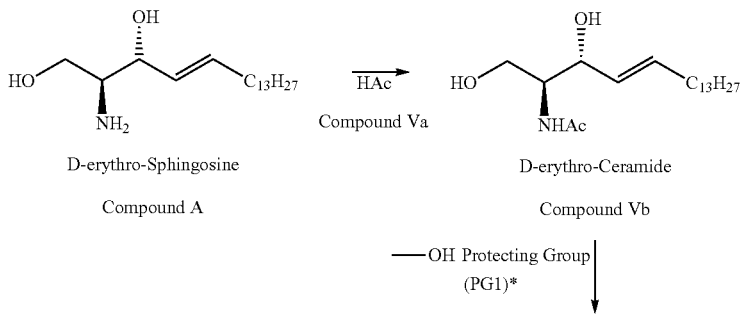

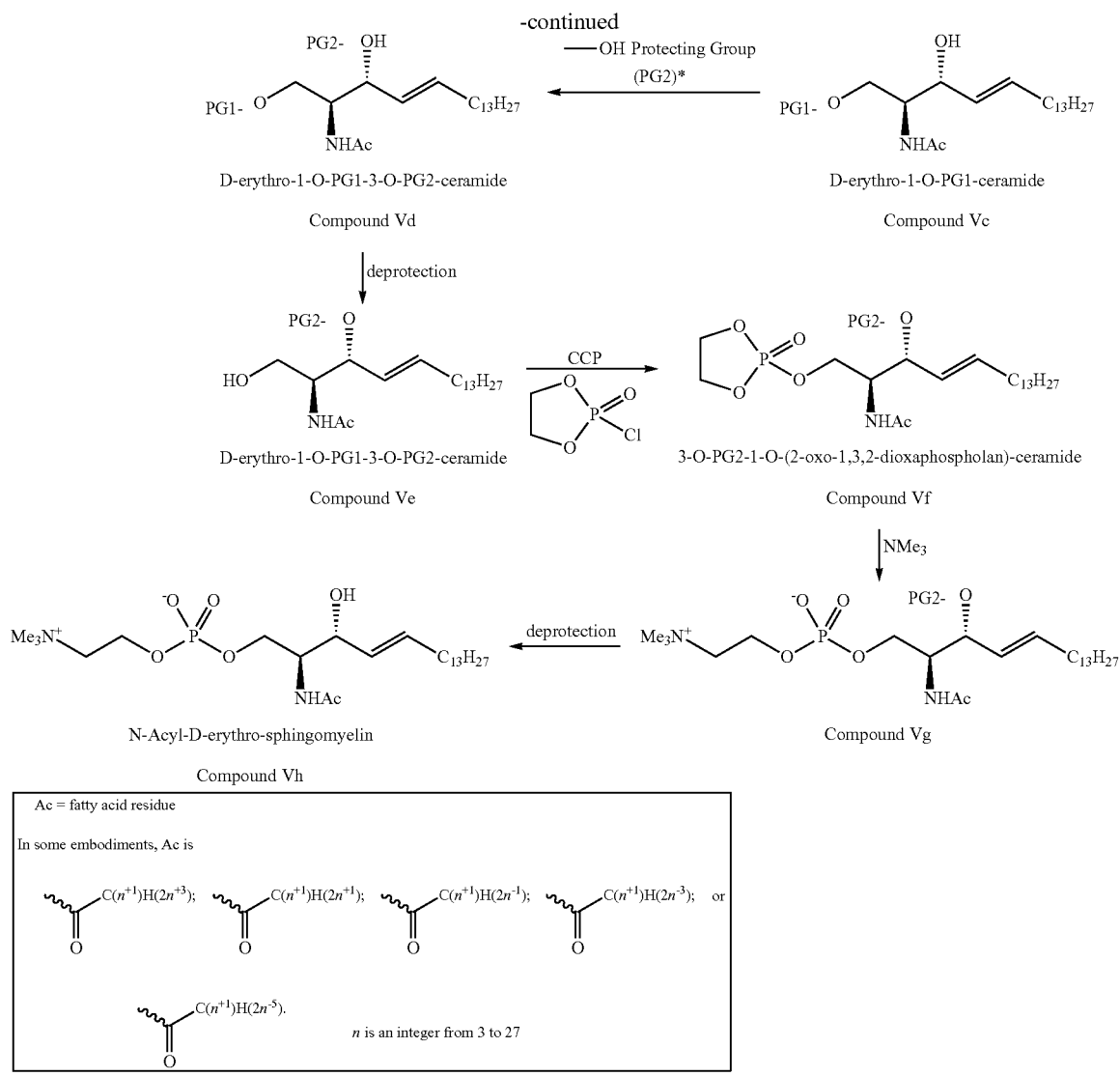

*PG1 and PG2 are any suitable protecting groups known in the art. In certain embodiments PG1 is triphenylmethyl (Trt). In certain embodiments PG2 is benzoyl (Bz)

Synthesis of N-acyl D-erythro-ceramide

In certain embodiments of the invention, the N-acylation of the D-erythro-sphingosine with fatty acid to yield N-acyl D-erythro-ceramide proceeds as shown in Scheme II. The steps are as follows: D-erythro-sphingosine (Compound A), the fatty acid (Compound Va), and a peptide coupling agent are suspended in an aprotic organic solvent and the mixture is cooled at a temperature of about 0-5° C. In one in embodiment, the aprotic organic solvent is tetrahydrofuran, dimethylforamide, 2-methyltetrahydrofuran, or mixtures thereof. In particular embodiments of the invention, the peptide coupling agent is O-Benzotriazole-N,N,N',N'-tetramethyl-uronium-hexafluoro-phosphate.

An organic base, such as, but not limited to triethylamine or pyridine, is added to the mixture of D-erythro-sphingosine (Compound A), fatty acid (Compound Va), and peptide coupling agent. In certain embodiments, the organic base is in an aprotic organic solvent and is tetrahydrofuran, dimethylforamide, 2-methyltetrahydrofuran, or mixtures thereof. In further embodiments of the invention, the organic base is added over the course of about 15 to 90 minutes. The mixture is then stirred for 1 to 15 hours at a temperature of about 0-22° C. In certain embodiments of the invention, the reaction proceeds at a temperature of about 0-5° C. In other embodiments of the invention, the reaction proceeds at about 22° C. In yet other embodiments of the invention, the reaction proceeds at about room temperature.

After stirring for about 1 to 15 hours, the product is precipitated by the addition of an acid. In certain embodiments of the invention, the acid is an organic acid, such as citric acid, acetic acid, or oxalic acid. The acid can be in an aqueous solution when added. The reaction can be at about 22° C. when the acid is added. The resulting suspension can be stirred for 30 to 120 minutes at a temperature of about 0-5° C. In certain embodiments of the invention, the suspension is stirred at about 22° C.

After stirring, the suspension is filtered. The resulting product can then be resuspended in water, after which it can be filtered and washed. The resuspension can occur at least one more time. The resulting product, N-acyl D-erythro-ceramide (Compound Vb), can be washed with water, acetone, or a mixture thereof.

Synthesis of benzoyl-protected N-acyl D-erythro-ceramide

In certain embodiments of the invention, the primary hydroxyl of the N-acyl D-erythro-ceramide is protected, followed by protection of the secondary hydroxyl, and then deprotection of the primary hydroxyl. In further embodiments of the invention, the protection and deprotection steps proceed without isolation or purification of the primary hydroxy protected N-acyl D-erythro-ceramide.

In particular embodiments of the invention, the primary hydroxyl is protected with a trityl group. In certain embodiments of the invention, the secondary hydroxyl is protected with a benzoyl group. In further embodiments of the invention the primary hydroxyl is protected with a trityl group and the secondary hydroxyl is protected with a benzoyl group.

In certain embodiments of the invention, the protection of the primary hydroxyl proceeds as follows: N-acyl D-erythro-ceramide (Compound Vb) and trityl chloride are suspended in an organic solvent in the presence of a base. The reaction proceeds at a temperature of about 25-55° C. for about 10 to 60 hours to yield the trityl protected N-acyl D-erythro-ceramide (N-acyl-1-O-trityl-D-erythro-ceramide Compound Vc; PG1=-Trt). The organic solvent can be a nonpolar or polar solvent. In one embodiment of the invention, the organic solvent is a nonpolar solvent and is toluene, benzene, hexane or mixtures thereof. In one embodiment the organic solvent is an aprotic polar solvent. In one embodiment, the aprotic organic solvent is chlorinated and is methylene chloride, chloroform or carbon tetrachloride. In another embodiment, the aprotic organic solvent is nonchlorinated and is diethyl ether, tetrahydrofuran, or ethyl acetate. The base is typically an organic base, such as triethylamine or pyridine.

In certain embodiments of the invention, the protection of the primary hydroxyl yields less than 10% of N-acyl-1-O-trityl-3-O-trityl-D-erythro-ceramide. In further embodiments of the invention, the protection of the primary hydroxyl yields less than 7% of N-acyl-1-O-trityl-3-O-trityl-D-erythro-ceramide. In still further embodiments of the invention, the protection of the primary hydroxyl yields less than 5% of N-acyl-1-O-trityl-3-O-trityl-D-erythro-ceramide.

In further embodiments of the invention, the protection of the secondary hydroxyl proceeds directly as follows: the above reaction mixture is cooled to about 0-5° C. and benzoyl chloride and a base are added. The reaction proceeds at a temperature of about 0-5° C. for about 1 to 16 hours. The reaction product, benzoyl and trityl protected N-acyl D-erythro-ceramide (Compound Vd; PG1=-Trt; PG2=-Bz) can be extracted from the organic layer with an organic solvent, including, but not limited to, an aprotic organic solvent described above. The organic solvent is then removed by a suitable method known to one of skill in the art, including, but not limited to, evaporation. In particular embodiments the base is an organic base, such as triethylamine or pyridine.

In yet further embodiments of the invention, the deprotection of the primary hydroxyl proceeds directly as follows: the residue from the above reaction is dissolved in an organic solvent and an acid is added. The reaction proceeds at a temperature of about 22° C. for 1 to 16 hours. The reaction mixture is neutralized by the addition of a base. The organic solvent can be a protic polar solvent, an aprotic polar solvent, or a mixture thereof. In one embodiment the organic solvent is a protic polar solvent and is methanol, ethanol, n-propanol, or isopropanol. In one embodiment the organic solvent is an aprotic polar solvent. In one embodiment, the aprotic organic solvent is chlorinated and is methylene chloride, chloroform, or carbon tetrachloride. In another embodiment, the aprotic organic solvent is nonchlorinated and is diethyl ether, tetrahydrofuran, or ethyl acetate. The acid can be any acid known by one of skill to be suitable for removal of the trityl protecting group. In certain embodiments of the invention the acid is p-toluenesulfonic acid. In particular embodiments the base is an organic base, such as triethylamine or pyridine.

In certain embodiments of the invention the above deprotection product (Compound Ve; PG2=-Bz) can be purified by recrystallization, silica gel chromatography, high performance liquid chromatography or other methods known to those skilled in the art.

Phosphorylation and Amination of Benzoyl-Protected N-Acyl D-Erythro-Ceramide to Yield Benzoyl-Protected N-Acyl D-Erythro-Sphingomyelin In further embodiments of the invention the benzoyl-protected N-acyl D-erythro-ceramide, (Compound Ve; PG2=-Bz), is phosphorylated as follows: the benzoyl-protected N-acyl D-erythro-ceramide is dissolved in an organic solvent and an amine is added, after cooling to about 4-9° C., a solution of 2-Chloro-2-oxo-1,3,2-dioxaphospholane in an organic solvent is added. The reaction proceeds at a temperature from about 4-22° C. for about 2 to 6 hours to produce 3-O-Benzoyl-1-O-(2-oxo-1,3,2-dioxaphospholan)-ceramide (Compound VI). In certain embodiments of the invention, the reaction proceeds at about 4-9° C. for about 15 minutes to 2 hours and is then warmed to about 22° C. and proceeds for an additional 2 to 4 hours. The organic solvent can be a nonpolar solvent, a polar solvent, or mixtures thereof. In one embodiment of the invention, the organic solvent is a nonpolar solvent and is toluene, benzene, hexane or mixtures thereof. In one embodiment the organic solvent is an aprotic polar solvent such as acetonitrile, ethyl acetate, tetrahydrofuran, or mixtures thereof. The amine is typically tetramethylethylenediamine or triethylamine. In certain embodiments of the invention, the amine is tetramethylethylenediamine.

In certain embodiments, amination of the 3-O-Benzoyl-1-O-(2-oxo-1,3,2-dioxaphospholan)-ceramide (Compound Vf, PG2=-Bz) occurs without purification or isolation of the phosphorylated benzoyl-protected N-acyl D-erythro-ceramide. After the above reaction has proceeded for about 2 to 6 hours, additional organic solvent and trimethylamine is added and the reaction is heated to 60-70° C. and proceeds for 10 to 16 hours to yield the benzoyl-protected N-acyl D-erythro-sphingomyelin (Compound Vg, PG2=-Bz). The organic solvent can be a nonpolar solvent, a polar solvent or mixtures thereof. In one embodiment of the invention, the organic solvent is a nonpolar solvent and is toluene, benzene, hexane or mixtures thereof. In one embodiment the organic solvent is an aprotic polar solvent such as acetonitrile, ethyl acetate, tetrahydrofuran, or mixtures thereof. In certain embodiments, trimethylamine is added as a liquid. In other embodiments, triethylamine is added in a gaseous form. In particular embodiments, the liquid trimethylamine is anhydrous. In certain embodiments the reaction is cooled to about −10° C.-0° C. prior to addition of liquid trimethyl amine.

In certain embodiments of the invention the benzoyl-protected N-acyl D-erythro-sphingomyelin can be purified by recrystallization, silica gel chromatography, high performance liquid chromatography or other methods known to those skilled in the art.

Deprotection of Benzoyl-Protected N-acyl D-erythro-sphingomyelin to yield N-acyl D-erythro-sphingomyelin The removal of the benzoyl protecting group from the benzoyl-protected N-acyl D-erythro-sphingomyelin proceeds as follows: the benzoyl-protected sphingomyelin is dissolved in a protic polar solvent and a base is added. The reaction proceeds for 8 to 24 hours at about 22° C. In certain embodiments of the invention an aprotic solvent and water are added to the reaction mixture and the N-acyl D-erythro-sphingomyelin (Compound Vh) is recovered from the organic layer. In one embodiment the protic polar solvent is methanol, ethanol, n-propanol, isopropanol, or mixtures thereof. In another embodiment, the aprotic organic solvent is chlorinated and is methylene chloride, chloroform, or carbon tetrachloride. In yet another embodiment the base is sodium methoxide.

In further embodiments of the invention the N-acyl D-erythro-sphingomyelin can be purified by recrystallization, silica gel chromatography, high performance liquid chromatography or other methods known to those skilled in the art.

In certain embodiments of the invention, the resulting N-acyl D-erythro-sphingomyelin has an enantiomeric purity of at least about 85%. In further embodiments of the invention, the N-acyl D-erythro-sphingomyelin has an enantiomeric purity of at least about 90%. In yet further embodiments N-acyl D-erythro-sphingomyelin has an enantiomeric purity of at least about 95%. In still further embodiments N-acyl D-erythro-sphingomyelin has an enantiomeric purity of at least about 98%.

Synthesis of N-palmitoyl-D-erythro-sphingomyelin

In a particular embodiment of the invention N-palmitoyl-D-erythro-sphingomyelin is synthesized as shown in Scheme VI:

One equivalent of palmitic acid, one equivalent of D-erythro-sphingosine (Compound A), and 1.10 equivalents of O-Benzotriazole-N,N,N',N'-tetramethyl-uronium-hexafluoro-phosphate are suspended in tetrahydrofuran and dimethylformamide and cooled to about 0-5° C. Two to three equivalents of triethylamine are added and the mixture is stirred for about one to twelve hours at about 0-5° C. The mixture is warmed to about 22° C. An aqueous solution of citric acid is added and the mixture is stirred for 15 to 90 min at about 22° C. The resulting suspension is filtered and the cake is suspended in water, at room temperature. The suspension is filtered and washed with water and acetone. The resulting product, N-palmitoyl D-erythro-sphingosine (Compound E), can then be dried.

For the first hydroxyl protection, 1 equivalent of N-palmitoyl D-erythro-sphingosine was suspended in pyridine and methylene chloride. A solution of about 1.05 equivalents of trityl chloride in methylene chloride is added followed by additional methylene chloride. The reaction mixture was stirred at about 25° C. for 50-60 hours.

In certain embodiments of the invention, the protection of the primary hydroxyl yields less than 10% of N-palmitoyl-1-O-trityl-3-O-trityl-D-erythro-sphingosine. In further embodiments of the invention, the protection of the primary hydroxyl yields less than 7% of N-palmitoyl-1-O-trityl-3-O-trityl-D-erythro-sphingosine. In still further embodiments of the invention, the protection of the primary hydroxyl yields less than 5% of N-palmitoyl-1-O-trityl-3-O-trityl-D-erythro-sphingosine.

For the second hydroxyl protection, the reaction mixture from the first hydroxyl protection (Compound VIa) is cooled to about 2° C. N,N-Dimethylaminopyridine at about 0.10 equivalent, benzoyl chloride at about 1.50 equivalents are added and followed by additional methylene chloride. The reaction is allowed to proceed at about 2° C. with stirring until thin layer chromatography (TLC) analysis shows a content of intermediate N-palmitoyl 1-O-Trityl-sphingosine of less than about 5%. Ethyl acetate and an aqueous citric acid and sodium chloride solution are added to the reaction and the N-palmitoyl D-erythro-1-O-trityl-3-O-benzoyl-sphingosine (Compound VIb) is recovered from the organic phase.

To remove the trityl protecting group, N-palmitoyl D-erythro-1-O-trityl-3-O-benzoyl-sphingosine is dissolved in methanol and methylene chloride and cooled to 2° C. The pH is adjusted to 2.5 with a solution of 0.57 equivalents of para-toluene sulfonic acid monohydrate in methanol. The reaction is allowed to proceed at about 22° C. with stirring until TLC analysis showed a content of intermediate 1-O-Trityl-3-O-benzoyl-sphingosine of less than 5%. Triethylamine is added to adjust the pH to about 7.0. The reaction mixture is evaporated to dryness and the resulting crude 3-O-Benzoyl-ceramide-C16 is suspended in hexane at about 40° C. and cooled down to about 0° C. After about 30 to 60 minutes the solid is isolated by filtration and washed with hexane. The resulting product can then be purified by an appropriate method, such as silica gel chromatography.

One equivalent of N-palmitoyl 3-O-benzoyl-D-erythro-sphingosine (Compound Vc) is dissolved in toluene and about 0.6 to 1 equivalents of tetramethylethylenediamine is added and the mixture is cooled to about 4-9° C. About 1 to 2 equivalents of 2-chloro-2-oxo-1,3,2-dioxaphospholane in acetonitrile is added, followed by additional acetonitrile. The reaction is warmed to about 22° C. and stirring continued for 1-3 hours. After which additional acetonitrile is added and the temperature decreased to about −10 to 0° C. About 40 to 60 equivalents of liquid triethylamine are added and the reaction is heated to about 60-70° C. and proceeds for 10 to 16 hours to yield the N-palmitoyl 3-O-benzoyl-D-erythro-sphingomyelin (Compound VId). The reaction is cooled to about −30° C. and the resulting suspension is filtered. The crude N-palmitoyl 3-O-benzoyl-D-erythro-sphingomyelin is further purified by silica gel chromatography.

One equivalent of N-palmitoyl 3-O-benzoyl-D-erythro-sphingomyelin is dissolved in methanol and about 0.2 equivalents of sodium methoxide is added and the mixture is stirred for 20-26 hours at about 22° C. Methylene chloride and water are added and the pH is adjusted to about 7 with the addition of hydrochloric acid. N-palmitoyl D-erythro-sphingomyelin is recovered from the organic layer.

In further embodiments of the invention the N-palmitoyl D-erythro-sphingomyelin can be purified by recrystallization, silica gel chromatography, high performance liquid chromatography or other methods known to those skilled in the art.

In certain embodiments of the invention, the resulting N-palmitoyl-D-erythro-sphingosine has an enantiomeric purity of at least about 85%. In further embodiments of the invention, the N-palmitoyl-D-erythro-sphingomyelin has an enantiomeric purity of at least about 90%. In yet further embodiments N-palmitoyl-D-erythro-sphingomyelin has an enantiomeric purity of at least about 95%. In still further embodiments N-palmitoyl-D-erythro-sphingomyelin has an enantiomeric purity of at least about 98%.

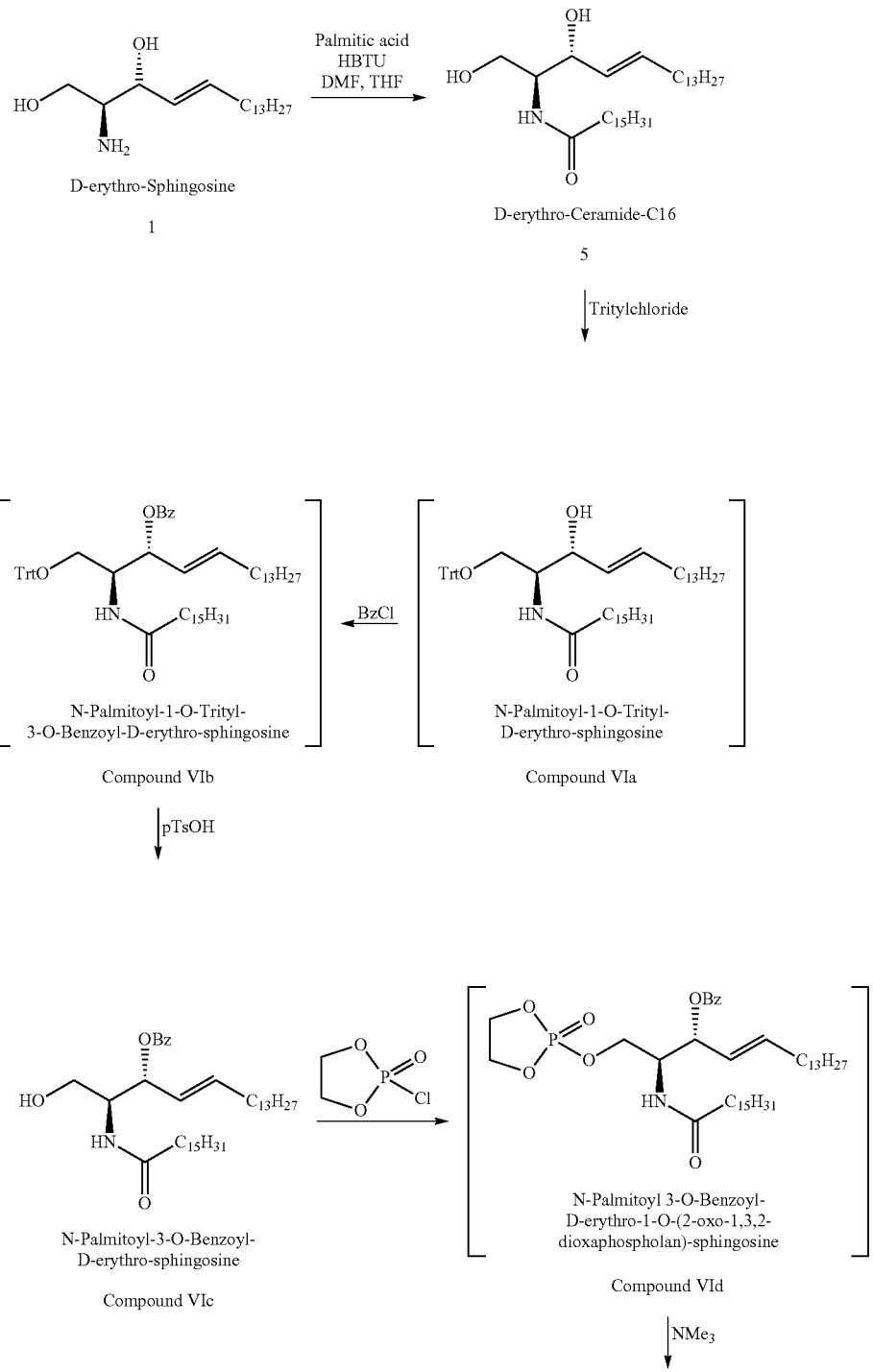

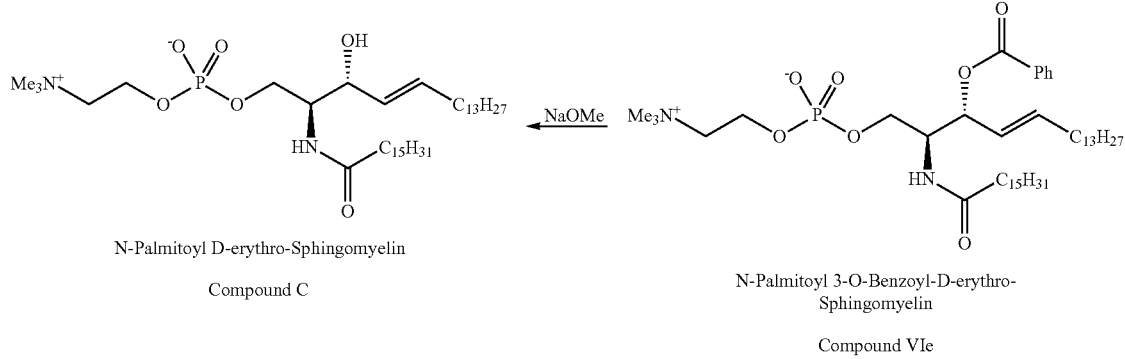

Synthesis of N-Acyl D-Erythro-Dihydrosphingomyelin from D-Erythro-Dihydrosphingosine and a Fatty Acid In a further embodiment, the invention provides a method for synthesizing a D-erythro-dihydrosphingomyelin starting from D-erythro-dihydrosphingosine and a suitable fatty acid as shown in Scheme VII comprising the steps of:
a) acylating D-erythro-dihydrosphingosine with a suitable fatty acid (Compound VIIa) to yield an D-erythro-dihydroceramide;
b) protecting the primary hydroxyl group of the D-erythro-dihydroceramide VIIb with a first protection group to yield Compound VIIe;
c) protecting the secondary hydroxyl group of the D-erythro-dihydroceramide with a second protection group yield to yield Compound VIId;
d) removing the first protecting group of Compound VIId to yield Compound Vile;
e) reacting Compound VIIe with 2-chloro-2-oxo-1,3,2-dioxaphospholane (CCP) to yield Compound VIIf;
f) reacting Compound VIIf with trimethylamine to yield Compound VIIg;
g) removing the second protecting group of Compound VIIg with sodium methoxide to yield the D-erythro-dihydrosphingomyelin.

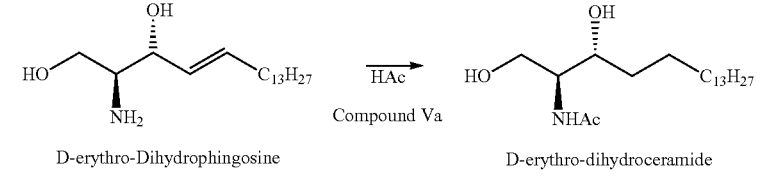

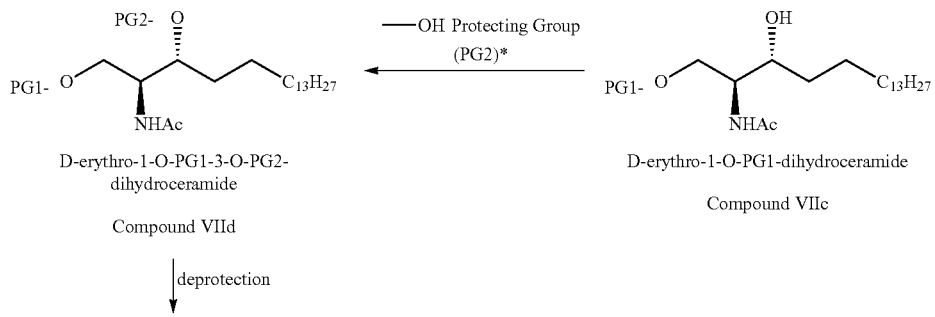

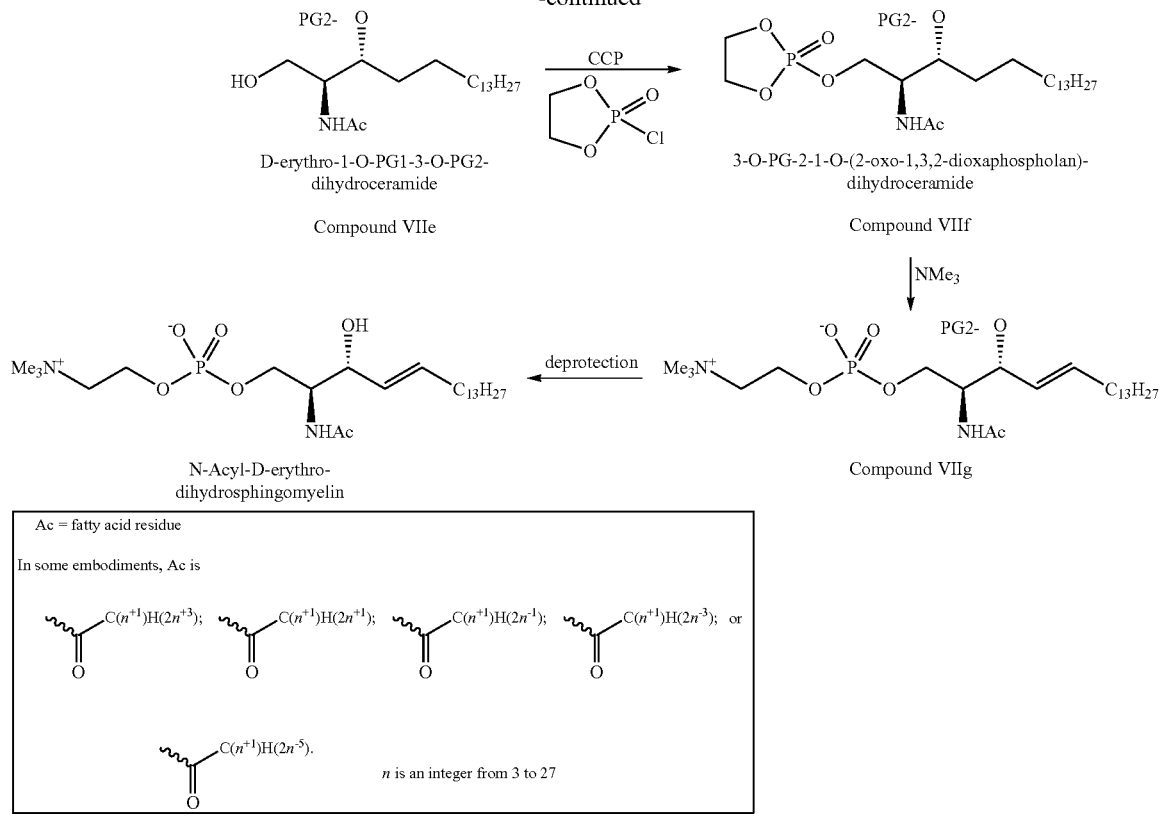

*PG1 and PG2 are any suitable protecting groups known in the art. In certain embodiments PG1 is triphenylmethyl (Trt). In certain embodiments PG2 is benzoyl (Bz) Synthesis of N-acyl D-erythro-dihydroceramide In certain embodiments of the invention, the N-acylation of the D-erythro-dihydrosphingosine with fatty acid to yield N-acyl D-erythro-dihydroceramide proceeds as shown in Scheme VII. The steps are as follows: D-erythro-dihydrosphingosine (Compound B), the fatty acid (Compound VIIa), and a peptide coupling agent are suspended in an aprotic organic solvent and the mixture is cooled at a temperature of about 0-5° C. In one in embodiment, the aprotic organic solvent is tetrahydrofuran, dimethylformamide, 2-methyltetrahydrofuran, or mixtures thereof. In particular embodiments of the invention, the peptide coupling agent is O-Benzotriazole-N,N,N',N'-tetramethyl-uronium-hexafluoro-phosphate.

An organic base, such as, but not limited to triethylamine or pyridine, is added to the mixture of D-erythro-dihydrosphingosine, fatty acid, and peptide coupling agent. In certain embodiments, the organic base is in an aprotic organic solvent and is tetrahydrofuran, dimethylformamide, 2-methyltetrahydrofuran, or mixtures thereof. In further embodiments of the invention, the organic base is added over the course of about 15 to 90 minutes. The mixture is then stirred for 1 to 15 hours at a temperature of about 0-22° C. In certain embodiments of the invention, the reaction proceeds at a temperature of about 0-5° C. In other embodiments of the invention, the reaction proceeds at about 22° C. In yet other embodiments of the invention, the reaction proceeds at about room temperature.

After stirring for about 1 to 15 hours, the product is precipitated by the addition of an acid. In certain embodiments of the invention, the acid is an organic acid, such as citric acid, acetic acid, or oxalic acid. The acid can be in an aqueous solution when added. The reaction can be at about 22° C. when the acid is added. The resulting suspension can be stirred for 30 to 120 minutes at a temperature of about 0-5° C. In certain embodiments of the invention, the suspension is stirred at about 22° C.

After stirring, the suspension is filtered. The resulting product can then be resuspended in water, after which it can be filtered and washed. The resuspension can occur at least one more time. The resulting product, N-acyl D-erythro-dihydroceramide (Compound VIIb), can be washed with water, acetone, or a mixture thereof.

Synthesis of Benzoyl-Protected N-acyl
D-erythro-dihydroceramide

In certain embodiments of the invention, the primary hydroxyl of the N-acyl D-erythro-dihydroceramide is protected, followed by protection of the secondary hydroxyl, and then deprotection of the primary hydroxyl. In further embodiments of the invention, the protection and deprotection steps proceed without isolation or purification of the primary hydroxyl protected N-acyl D-erythro-dihydroceramide.

In particular embodiments of the invention, the primary hydroxyl is protected with a trityl group. In certain embodiments of the invention, the secondary hydroxyl is protected with a benzoyl group. In further embodiments of the invention the primary hydroxyl is protected with a trityl group and the secondary hydroxyl is protected with a benzoyl group.

In certain embodiments of the invention, the protection of the primary hydroxyl proceeds as follows: N-acyl D-erythro-dihydroceramide (Compound VIIb) and trityl chloride are suspended in an organic solvent in the presence of a base. The reaction proceeds at a temperature of about 25-55° C. for about 10 to 60 hours to yield the trityl protected N-acyl D-erythro-dihydroceramide (N-acyl-1-O-trityl-D-erythro-dihydroceramide Compound VIIc; PG1=-Trt). The organic solvent can be a nonpolar or polar solvent. In one embodiment of the invention, the organic solvent is a nonpolar solvent and is toluene, benzene, hexane or mixtures thereof. In one embodiment the organic solvent is an aprotic polar solvent. In one embodiment, the aprotic organic solvent is chlorinated and is methylene chloride, chloroform or carbon tetrachloride. In another embodiment, the aprotic organic solvent is nonchlorinated and is diethyl ether, tetrahydrofuran, or ethyl acetate. The base is typically an organic base, such as triethylamine or pyridine.

In certain embodiments of the invention, the protection of the primary hydroxyl yields less than 10% of N-acyl-1-O-trityl-3-O-trityl-D-erythro-dihydroceramide. In further embodiments of the invention, the protection of the primary hydroxyl yields less than 7% of N-acyl-1-O-trityl-3-O-trityl-D-erythro-ceramide. In still further embodiments of the invention, the protection of the primary hydroxyl yields less than 5% of N-acyl-1-O-trityl-3-O-trityl-D-erythro-dihydroceramide.

In further embodiments of the invention, the protection of the secondary hydroxyl proceeds directly as follows: the above reaction mixture is cooled to about 0-5° C. and benzoyl chloride and a base are added. The reaction proceeds at a temperature of about 0-5° C. for about 1 to 16 hours. The reaction product, benzoyl and trityl protected N-acyl D-erythro-dihydroceramide (Compound VIId; PG1=-Trt; PG2=-Bz) can be extracted from the organic layer with an organic solvent, including, but not limited to, an aprotic organic solvent described above. The organic solvent is then removed by a suitable method known to one of skill in the art, including, but not limited to, evaporation. In particular embodiments the base is an organic base, such as triethylamine or pyridine.

In yet further embodiments of the invention, the deprotection of the primary hydroxyl proceeds directly as follows: the residue from the above reaction is dissolved in an organic solvent and an acid is added. The reaction proceeds at a temperature of about 22° C. for 1 to 16 hours. The reaction mixture is neutralized by the addition of a base. The organic solvent can be a protic polar solvent, an aprotic polar solvent, or a mixture thereof. In one embodiment the organic solvent is a protic polar solvent and is methanol, ethanol, n-propanol, or isopropanol. In one embodiment the organic solvent is an aprotic polar solvent. In one embodiment, the aprotic organic solvent is chlorinated and is methylene chloride, chloroform, or carbon tetrachloride. In another embodiment, the aprotic organic solvent is nonchlorinated and is diethyl ether, tetrahydrofuran, or ethyl acetate. The acid can be any acid known by one of skill to be suitable for removal of the trityl protecting group. In certain embodiments of the invention the acid is p-toluenesulfonic acid. In particular embodiments the base is an organic base, such as triethylamine or pyridine.

In certain embodiments of the invention the above deprotection product (Compound VIIe; PG2=-Bz) can be purified by recrystallization, silica gel chromatography, high performance liquid chromatography or other methods known to those skilled in the art.

Phosphorylation and Amination of Benzoyl-Protected N-Acyl D-Erythro-Dihydroceramide to Yield Benzoyl-Protected N-Acyl D-Erythro-Dihydrosphingomyelin In further embodiments of the invention the benzoyl-protected N-acyl D-erythro-dihydroceramide, (Compound VIIe; PG2=-Bz), is phosphorylated as follows: the benzoyl-protected N-acyl D-erythro-dihydroceramide is dissolved in an organic solvent and an amine is added, after cooling to about 4-9° C., a solution of 2-Chloro-2-oxo-1,3,2-dioxaphospholane in an organic solvent is added. The reaction proceeds at a temperature from about 4-22° C. for about 2 to 6 hours to produce 3-O-Benzoyl-1-O-(2-oxo-1,3,2-dioxaphospholan)-dihydroceramide (Compound VIIf; PG2=-Bz). In certain embodiments of the invention, the reaction proceeds at about 4-9° C. for about 15 minutes to 2 hours and is then warmed to about 22° C. and proceeds for an additional 2 to 4 hours. The organic solvent can be a nonpolar solvent, a polar solvent, or mixtures thereof. In one embodiment of the invention, the organic solvent is a nonpolar solvent and is toluene, benzene, hexane or mixtures thereof. In one embodiment the organic solvent is an aprotic polar solvent such as acetonitrile, ethyl acetate, tetrahydrofuran, or mixtures thereof. The amine is typically tetramethylethylenediamine or triethylamine. In certain embodiments of the invention, the amine is tetramethylethylenediamine.

In certain embodiments, amination of the 3-O-Benzoyl-1-O-(2-oxo-1,3,2-dioxaphospholan)-dihydroceramide (Compound VIIf) occurs without purification or isolation of the phosphorylated benzoyl-protected N-acyl D-erythro-dihydroceramide. After the above reaction has proceeded for about 2 to 6 hours, additional organic solvent and trimethylamine is added and the reaction is heated to 60-70° C. and proceeds for 10 to 16 hours to yield the benzoyl-protected N-acyl D-erythro-dihydrosphingomyelin (Compound VIIg). The organic solvent can be a nonpolar solvent, a polar solvent or mixtures thereof. In one embodiment of the invention, the organic solvent is a nonpolar solvent and is toluene, benzene, hexane or mixtures thereof. In one embodiment the organic solvent is an aprotic polar solvent such as acetonitrile, ethyl acetate, tetrahydrofuran, or mixtures thereof. In certain embodiments, trimethylamine is added as a liquid. In other embodiments, triethylamine is added in a gaseous form. In particular embodiments, the liquid trimethylamine is anhydrous. In certain embodiments the reaction is cooled to about −10° C.-0° C. prior to addition of liquid trimethyl amine.

In certain embodiments of the invention the benzoyl-protected N-acyl D-erythro-dihydrosphingomyelin can be purified by recrystallization, silica gel chromatography, high performance liquid chromatography or other methods known to those skilled in the art.

Deprotection of Benzoyl-Protected N-Acyl D-Erythro-Dihydrosphingomyelin to Yield N-Acyl D-Erythro-Dihydrosphingomyelin The removal of the benzoyl protecting group from the benzoyl-protected N-acyl D-erythro-dihydrosphingomyelin proceeds as follows: the benzoyl-protected dihydrosphingomyelin is dissolved in a protic polar solvent and a base is added. The reaction proceeds for 8 to 24 hours at about 22° C. In certain embodiments of the invention an aprotic solvent and water are added to the reaction mixture and the N-acyl D-erythro-dihydrosphingomyelin (Compound VIIh) is recovered from the organic layer. In one embodiment the protic polar solvent is methanol, ethanol, n-propanol, isopropanol, or mixtures thereof. In another embodiment, the aprotic organic solvent is chlorinated and is methylene chloride, chloroform, or carbon tetrachloride. In yet another embodiment the base is sodium methoxide.

In further embodiments of the invention the N-acyl D-erythro-dihydrosphingomyelin can be purified by recrystallization, silica gel chromatography, high performance liquid chromatography or other methods known to those skilled in the art.

In certain embodiments of the invention, the resulting N-acyl D-erythro-dihydrosphingomyelin has an enantiomeric purity of at least about 85%. In further embodiments of the invention, the N-acyl D-erythro-dihydrosphingomyelin has an enantiomeric purity of at least about 90%. In yet further embodiments N-acyl D-erythro-dihydrosphingomyelin has an enantiomeric purity of at least about 95%. In still further embodiments N-acyl D-erythro-dihydrosphingomyelin has an enantiomeric purity of at least about 98%.

In certain embodiments of the invention, the resulting N-palmitoyl-D-erythro-dihydrosphingosine has an enantiomeric purity of at least about 85%. In further embodiments of the invention, the N-palmitoyl-D-erythro-dihydrosphingomyelin has an enantiomeric purity of at least about 90%. In yet further embodiments N-palmitoyl-D-erythro-dihydrosphingomyelin has an enantiomeric purity of at least about 95%. In still further embodiments N-palmitoyl-D-erythro-dihydrosphingomyelin has an enantiomeric purity of at least about 98%.

Synthesis of
N-palmitoyl-D-erythro-dihydrosphingomyelin

In a particular embodiment of the invention N-palmitoyl-D-erythro-dihydrosphingomyelin is synthesized as shown in Scheme VIII.

One equivalent of palmitic acid, one equivalent of D-erythro-dihydrosphingosine, and 1.10 equivalents of O-Benzotriazole-N,N,N',N'-tetramethyl-uronium-hexafluoro-phosphate are suspended in tetrahydrofuran and dimethylformamide and cooled to about 0-5° C. Two to three equivalents of triethylamine are added and the mixture is stirred for about one to twelve hours at about 0-5° C. The mixture is warmed to about 22° C. An aqueous solution of citric acid is added and the mixture is stirred for 15 to 90 min at about 22° C. The resulting suspension is filtered and the cake is suspended in water, at room temperature. The suspension is filtered and washed with water and acetone. The resulting product, N-acyl D-erythro-dihydroceramide-C16, can then be dried.

For the first hydroxyl protection, 1 equivalent of N-acyl D-erythro-Dihydroceramide-C16 was suspended in pyridine and methylene chloride. A solution of about 1.05 equivalents of trityl chloride in methylene chloride is added followed by additional methylene chloride. The reaction mixture was stirred at about 25° C. for 50-60 hours.

In certain embodiments of the invention, the protection of the primary hydroxyl yields less than 10% of N-acyl-1-O-trityl-3-O-trityl-D-erythro-dihydroceramide-C16. In further embodiments of the invention, the protection of the primary hydroxyl yields less than 7% of N-acyl-1-O-trityl-3-O-trityl-D-erythro-dihydroceramide-C16. In still further embodiments of the invention, the protection of the primary hydroxyl yields less than 5% of N-acyl-1-O-trityl-3-O-trityl-D-erythro-dihydroceramide-C16. For the second hydroxyl protection, the reaction mixture from the first hydroxyl protection is cooled to about 2° C. N,N-Dimethylaminopyridine at about 0.10 equivalent, benzoyl chloride at about 1.50 equivalents are added and followed by additional methylene chloride. The reaction is allowed to proceed at about 2° C. with stirring until thin layer chromatography (TLC) analysis shows a content of intermediate 1-O-Trityl-dihydroceramide-C16 of less than about 5%. Ethyl acetate and an aqueous citric acid and sodium chloride solution are added to the reaction and the N-acyl D-erythro-1-O-trityl-3-O-benzoyl-dihydroceramide-C16 is recovered from the organic phase.

To remove the trityl protecting group, N-acyl D-erythro-1-O-trityl-3-O-benzoyl-dihydroceramide-C16 is dissolved in methanol and methylene chloride and cooled to 2° C. The pH is adjusted to 2.5 with a solution of 0.57 equivalents of para-toluene sulfonic acid monohydrate in methanol. The reaction is allowed to proceed at about 22° C. with stirring until TLC analysis showed a content of intermediate 1-O-Trityl-3-O-benzoyl-dihydroceramide-C16 of less than 5%. Triethylamine is added to adjust the pH to about 7.0. The reaction mixture is evaporated to dryness and the resulting crude 3-O-Benzoyl-dihydroceramide-C16 is suspended in hexane at about 40° C. and cooled down to about 0° C. After about 30 to 60 minutes the solid is isolated by filtration and washed with hexane. The resulting product can then be purified by an appropriate method, such as silica gel chromatography.

One equivalent of 3-O-benzoyl-N-acyl D-erythro-dihydroceramide-C16 is dissolved in toluene and about 0.6 to 1 equivalents of tetramethylethylenediamine is added and the mixture is cooled to about 4-9° C. About 1 to 2 equivalents of 2-chloro-2-oxo-1,3,2-dioxaphospholane in acetonitrile is added, followed by additional acetonitrile. The reaction is warmed to about 22° C. and stirring continued for 1-3 hours. After which additional acetonitrile is added and the temperature decreased to about −10 to 0° C. About 40 to 60 equivalents of liquid triethylamine are added and the reaction is heated to about 60-70° C. and proceeds for 10 to 16 hours to yield the 3-O-benzoyl-N-palmitoyl-D-erythro-dihydrosphingomyelin. The reaction is cooled to about −30° C. and the resulting suspension is filtered. The crude 3-O-benzoyl-N-palimioyl-D-erythro-dihydrosphingomyelin is further purified by silica gel chromatography.

One equivalent of 3-O-benzoyl-N-palimioyl-D-erythro-dihydrosphingomyelin is dissolved in methanol and about 0.2 equivalents of sodium methoxide is added and the mixture is stirred for 20-26 hours at about 22° C. Methylene chloride and water are added and the pH is adjusted to about 7 with the addition of hydrochloric acid. N-palmitoyl-D-erythro-dihydrosphingomyelin is recovered from the organic layer.

In further embodiments of the invention the N-palmitoyl-D-erythro-dihydrosphingomyelin can be purified by recrystallization, silica gel chromatography, high performance liquid chromatography or other methods known to those skilled in the art.

In certain embodiments of the invention, the resulting N-palmitoyl-D-erythro-dihydrosphingosine has an enantiomeric purity of at least about 85%. In further embodiments of the invention, the N-palmitoyl-D-erythro-dihydrosphingomyelin has an enantiomeric purity of at least about 90%. In yet further embodiments N-palmitoyl-D-erythro-dihydrosphingomyelin has an enantiomeric purity of at least about 95%. In still further embodiments N-palmitoyl-D-erythro-dihydrosphingomyelin has an enantiomeric purity of at least about 98%.

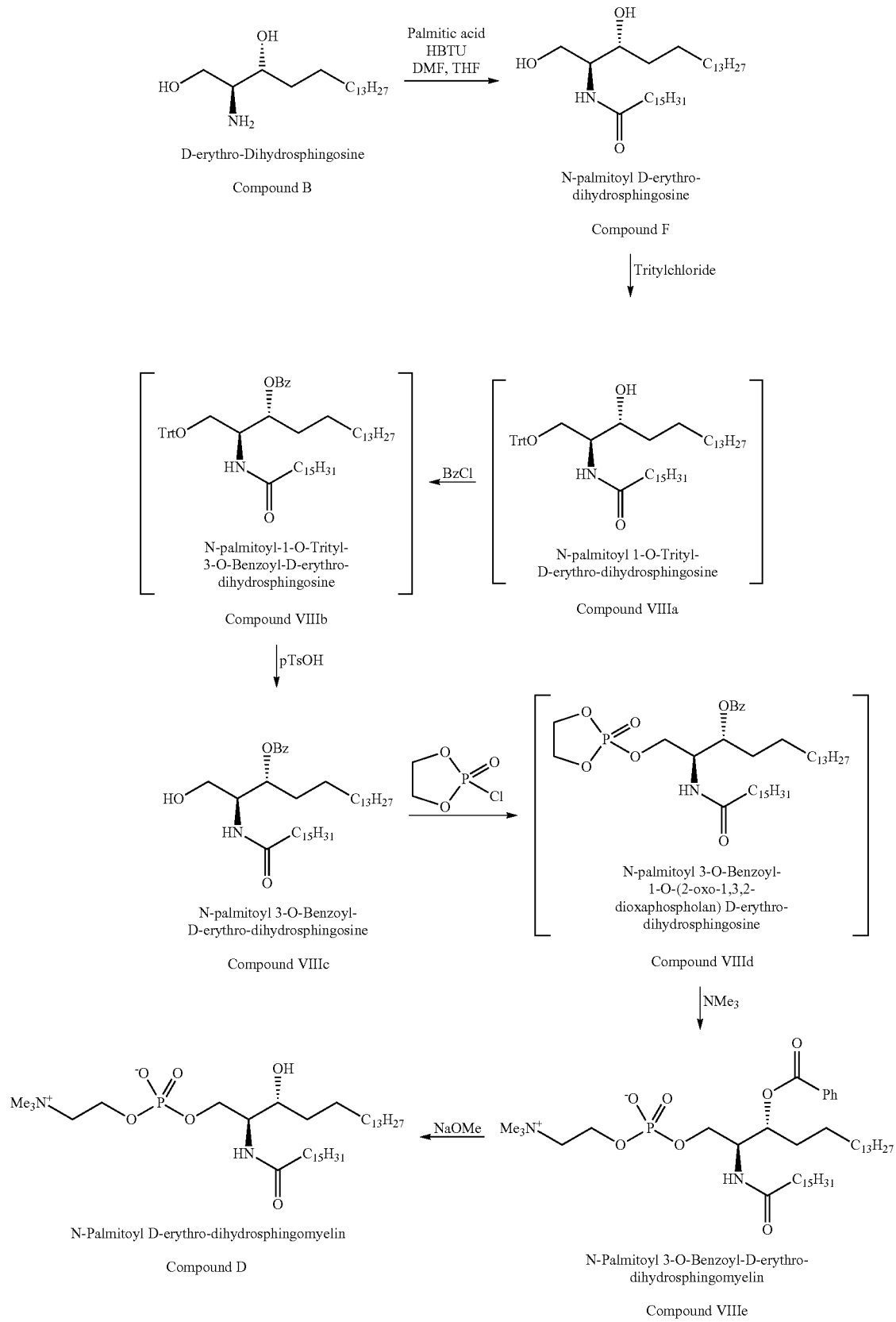

Direction Protection of (2S,3R,4E)-3-(tert-butoxy-carbonyl)-4-(1-hydroxy-hexadec-2-enyl)-2,2-dimethyloxazolidine to Yield sphingomyelin In another embodiment of the invention, the secondary hydroxyl of the sphingosine precursor (2S,3R,4E)-3-(tert-butoxycarbonyl)-4-(1-hydroxy-hexadec-2-enyl)-2,2-dimethyloxazolidine (Compound If in Scheme I) is protected and the synthesis of the sphingomyelin proceeds as shown in Scheme IX.

In one aspect of the invention the secondary hydroxyl can be protected with an ester, such as, but not limited to, benzoyl ester or fluorenylmethyloxycarbonyl ester, or with an ether, such as, but not limited to, t-butyldiphenylsilyl ether. The protection of the secondary hydroxyl is followed by the deprotection of the amine by removal of the tert-butoxycarbonyl (Boc) protecting group, resulting in 3-O protected D-erythro-sphingosine. The 3-O protected D-erythro-sphingosine can then be N-acylated by the addition of a suitable fatty acid and a peptide coupling agent. The resulting N-acyl 3-O protected D-erythro-ceramide can then proceed to the N-acyl D-erythro sphingomyelin as shown in Scheme V.

In a particular embodiment of the invention, the secondary hydroxyl of (2S,3R,4E)-3-(tert-butoxycarbonyl)-4-(1-hydroxy-hexadec-2-enyl)-2,2-dimethyloxazolidine (Compound 10 is protected with a benzoyl ester to yield (2S,3R,4E)-3-(tert-butoxycarbonyl)-4-(1-benzoyl-hexadec-2-enyl)-2,2-dimethyloxazolidine (Compound IXa) as shown in Scheme IX. The (2S,3R,4E)-3-(tert-butoxycarbonyl)-4-(1-benzoyl-hexadec-2-enyl)-2,2-dimethyloxazolidine is then dissolved in methanol and 2 to 3 equivalents of acetyl chloride are added in order to deprotect the amine by removing the tert-butoxycarbonyl (Boc) protecting group, resulting in 3-O-benzoyl-D-erythro-sphingosine (Compound IXb).

In certain embodiments of the invention, the N-acylation of the resulting D-erythro-3-O-benzoyl-sphingosine with palmitic acid to yield N-palmitoyl 3-O-benzoyl-D-erythro-sphingosine (Compound IXc) proceeds as shown in Scheme IX. The steps are as follows: 3-O benzoyl-D-erythro-sphingosine (Compound IXb), palmitic acid, and a peptide coupling agent are suspended in an aprotic organic solvent and the mixture is cooled at a temperature of about 0-5° C. In one in embodiment, the aprotic organic solvent is tetrahydrofuran, dimethylforamide, 2-methyltetrahydrofuran, or mixtures thereof. In particular embodiments of the invention, the peptide coupling agent is O-Benzotriazole-N,N,N',N'-tetramethyl-uronium-hexafluoro-phosphate.

An organic base, such as, but not limited to triethylamine or pyridine, is added to the mixture of 3-O benzoyl-D-erythro-sphingosine, palmitic acid, and peptide coupling agent. In certain embodiments, the organic base is in an aprotic organic solvent and is tetrahydrofuran, dimethylforamide, 2-methyltetrahydrofuran, or mixtures thereof. In further embodiments of the invention, the organic base is added over the course of about 15 to 90 minutes. The mixture is then stirred for 1 to 15 hours at a temperature of about 0-22° C. In certain embodiments of the invention, the reaction proceeds at a temperature of about 0-5° C. In other embodiments of the invention, the reaction proceeds at about 22° C. In yet other embodiments of the invention, the reaction proceeds at about room temperature.

After stirring for about 1 to 15 hours, the product is precipitated by the addition of an acid. In certain embodiments of the invention, the acid is an organic acid, such as citric acid, acetic acid, or oxalic acid. The acid can be in an aqueous solution when added. The reaction can be at about 22° C. when the acid is added. The resulting suspension can be stirred for 30 to 120 minutes at a temperature of about 0-5° C. In certain embodiments of the invention, the suspension is stirred at about 22° C.

After stirring, the suspension is filtered. The resulting product can then be resuspended in water, after which it can be filtered and washed. The resuspension can occur at least one more time. The resulting product, N-palmitoyl 3-O-benzoyl-D-erythro-sphingosine (Compound IX), can be washed with water, acetone, or a mixture thereof.

In certain embodiments of the invention the above product can be purified by recrystallization, silica gel chromatography, high performance liquid chromatography or other methods known to those skilled in the art.

The N-palmitoyl 3-O-benzoyl-D-erythro-sphingosine (Compound IX) can then proceed to N-palmitoyl D-erythro sphingomyelin as shown in Scheme VI.

Scheme IX

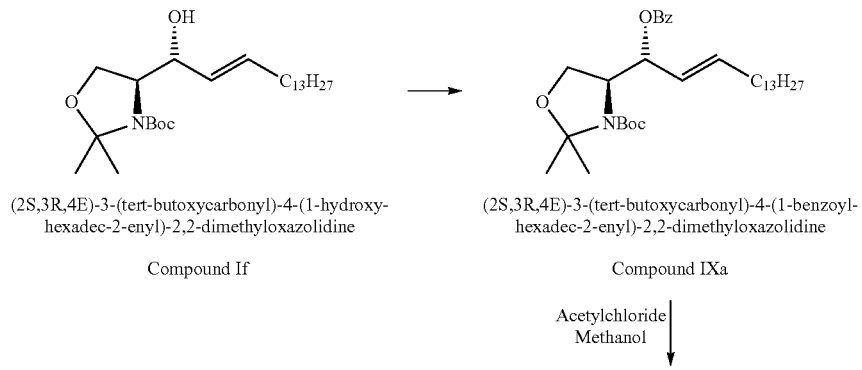

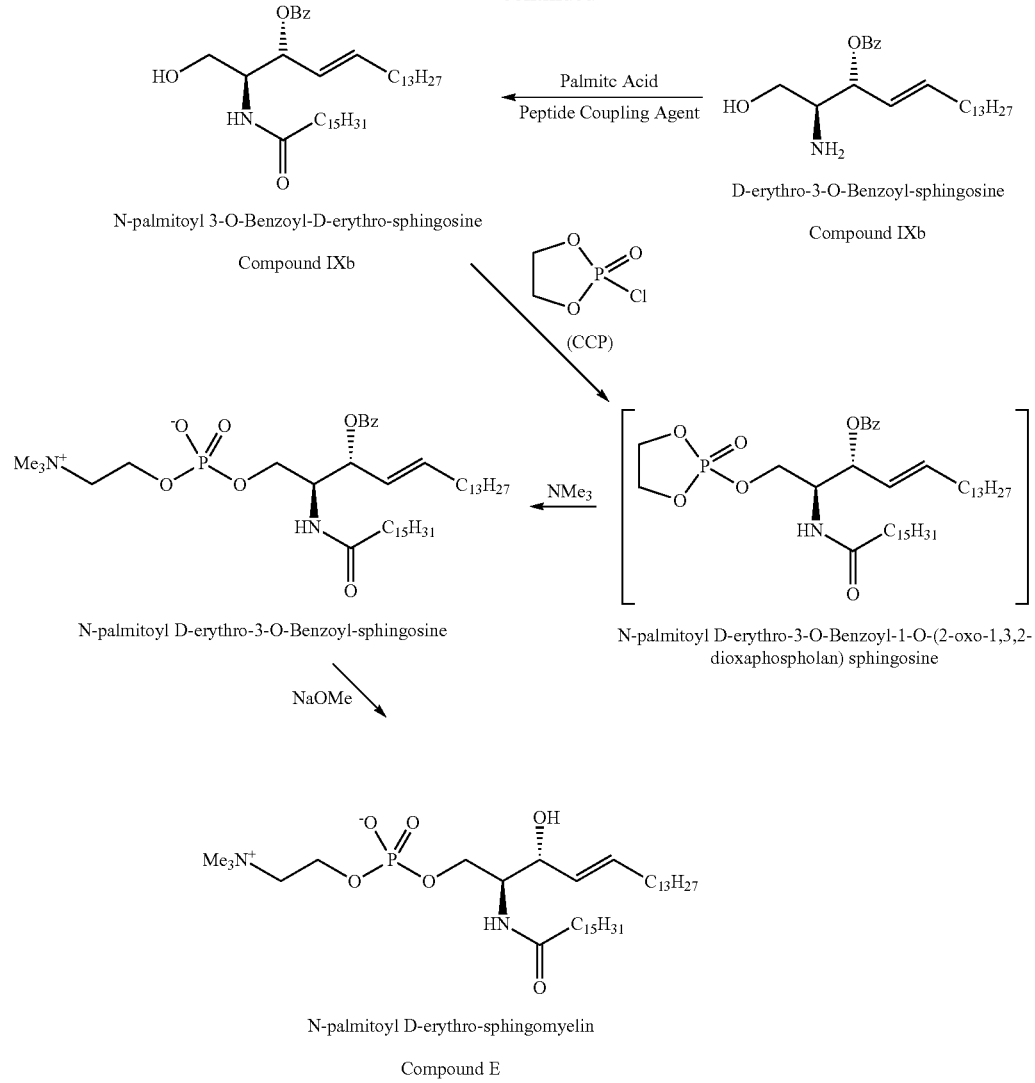

In certain embodiments of the invention, N-acyl D-erythro-sphingomyelins are prepared as described in Scheme X proceeding from D-erythro-alcohol (2S,3R,4E). N-acylation of the 3-O protected D-erythro-sphingosine to yield N-acyl 3-O protected D-erythro-ceramide is performed with a fatty acid and a peptide coupling agent in basic conditions, as described previously for the Scheme IX. The resulting N-acyl 3-O protected D-erythro-ceramide can then can then proceed to N-acyl D-erythro sphingomyelin as shown in Scheme V.

Scheme X

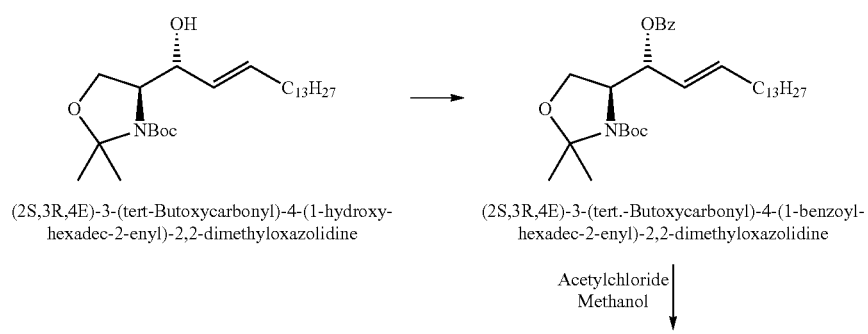

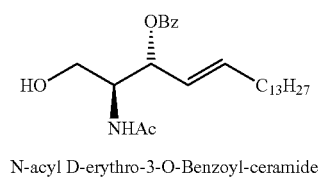

N-acyl D-erythro-3-O-Benzoyl-ceramide

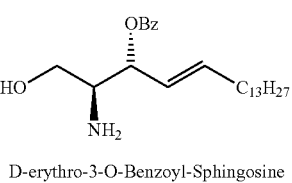

D-erythro-3-O-Benzoyl-Sphingosine

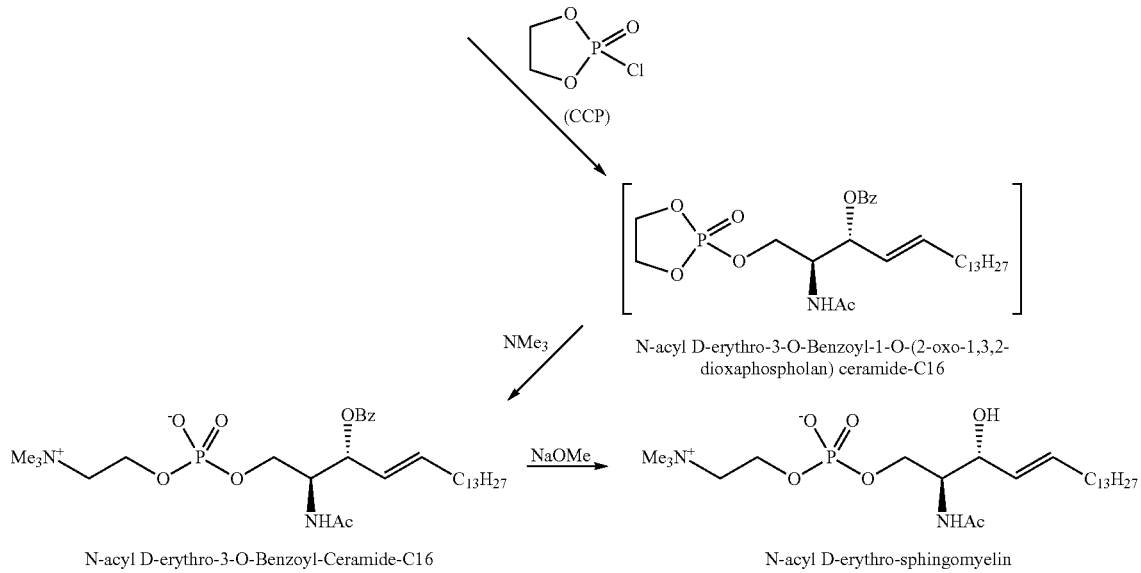

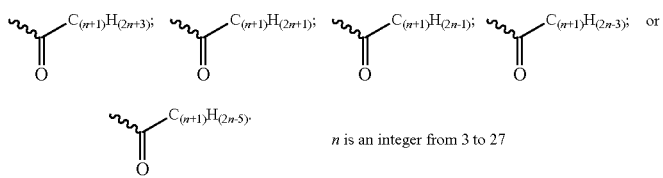

Direction Protection of (2S,3R,4E)-3-(tert-butoxycarbonyl)-4-(1-hydroxy-hexadecyl)-2,2-dimethyloxazolidine to Yield dihydrosphingomyelin In another embodiment of the invention, the secondary hydroxyl of the sphingosine precursor (2S, 3R,4E)-3-(tert-butoxycarbonyl)-4-(1-hydroxy-hexadecyl)-2,2-dimethyloxazolidine (Compound IIa in Scheme 11) is protected and the synthesis of the sphingomyelin proceeds as shown in Scheme XI and described above for Scheme IX.

Scheme XI

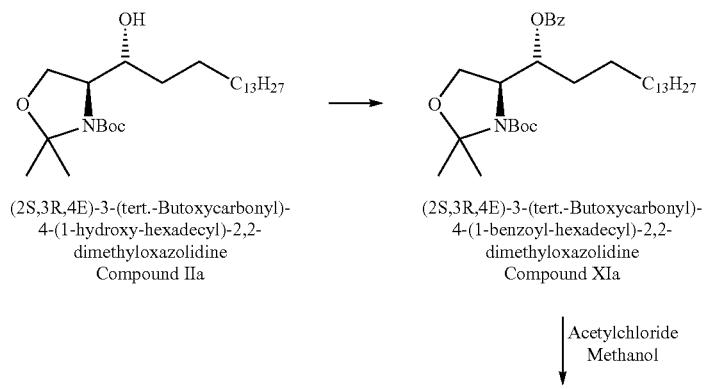

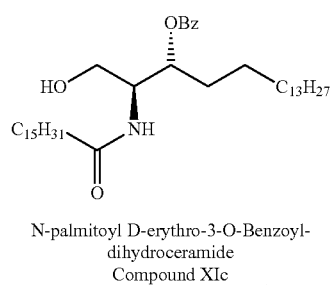

N-palmitoyl D-erythro-3-O-Benzoyl-
dihydroceramide
Compound XIc

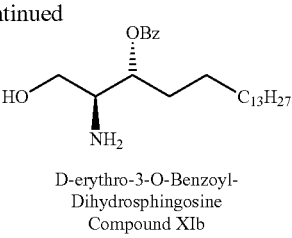

D-erythro-3-O-Benzoyl-
Dihydrosphingosine
Compound XIb

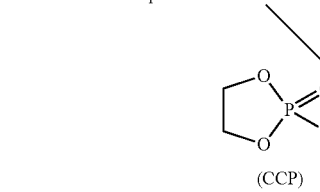

(CCP)

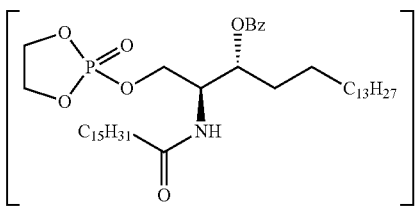

N-acyl D-erythro-3-O-Benzoyl-1-O-(2-oxo-1,3,2-
dioxaphospholan)dihydroceramide-C16
Compound XId

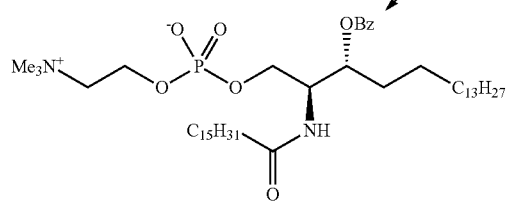

N-palmitoyl D-erythro-3-O-Benzoyl-
Dihydroceramide-C16
Compound XIe

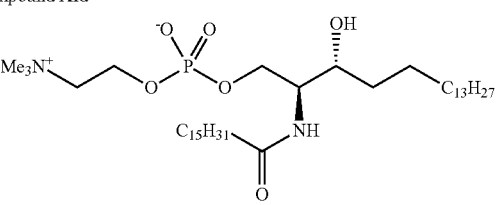

N-palmitoyl D-erythro-
Dihydrosphingomyelin
Compound D

In a particular embodiment of the invention, the secondary hydroxyl of (2S,3R,4E)-3-(tert-butoxycarbonyl)-4-(1-hydroxy-hexadecyl)-2,2-dimethyloxazolidine (Compound IIa in Scheme II) is protected with a benzoyl ester to yield (2S,3R,4E)-3-(tert-butoxycarbonyl)-4-(1-benzoyl-hexadecyl)-2,2-dimethyloxazolidine (Compound XIIa) as shown in Scheme XII. (2S,3R,4E)-3-(tert-butoxycarbonyl)-4-(1-benzoyl-hexadecyl)-2,2-dimethyloxazolidine is then dissolved in methanol and 2 to 3 equivalents of acetyl chloride are added in order to deprotect the amine by removing the tert-butoxycarbonyl (Boc) protecting group, resulting in 3-O-benzoyl-D-erythrodihydrosphingosine (Compound XIIb). The reaction proceeds as described for Scheme X.

Scheme XII

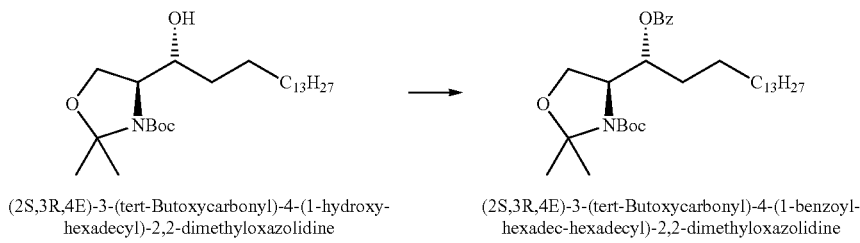

(2S,3R,4E)-3-(tert-Butoxycarbonyl)-4-(1-hydroxy-
hexadecyl)-2,2-dimethyloxazolidine Compound IIa (2S,3R,4E)-3-(tert-Butoxycarbonyl)-4-(1-benzoyl-
hexadec-hexadecyl)-2,2-dimethyloxazolidine Compound XIa Acetylchloride
Methanol

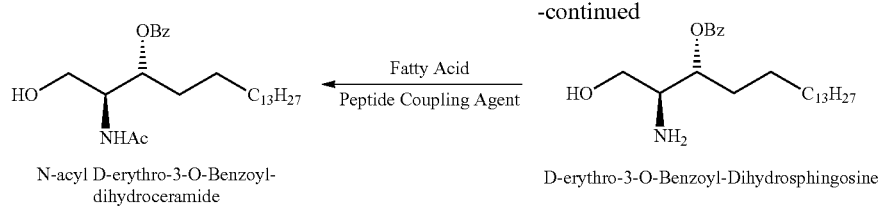

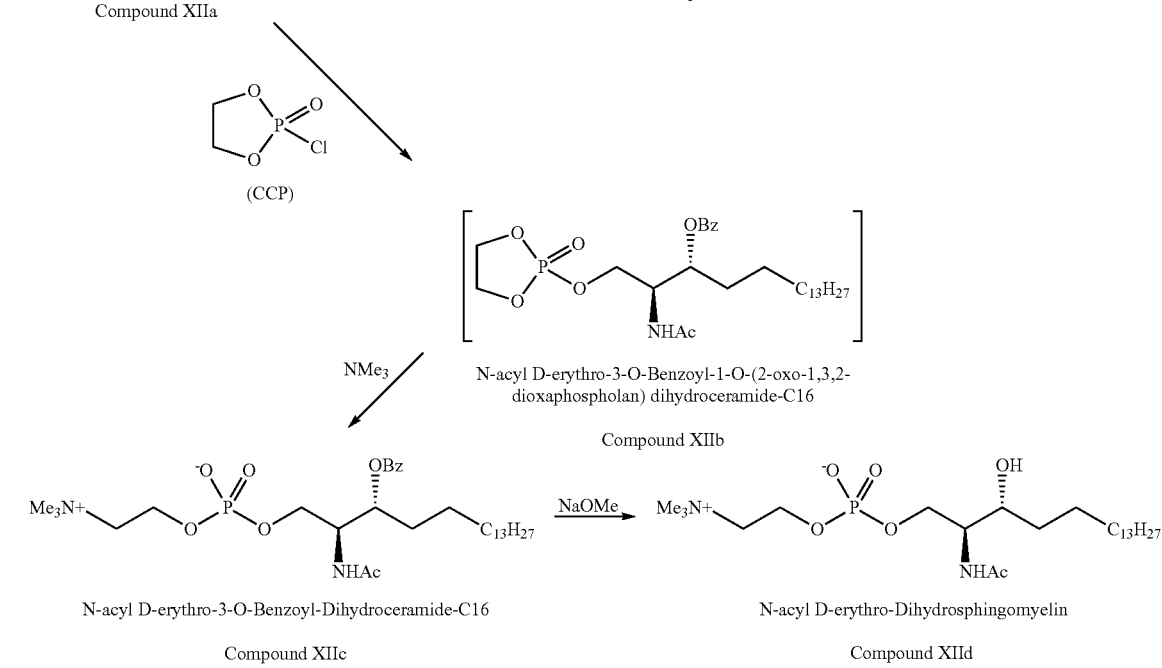

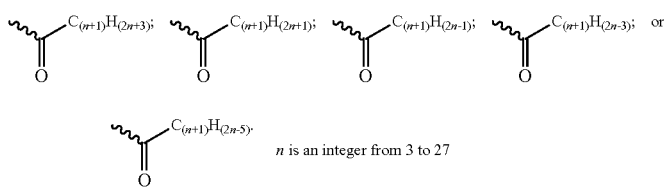

Selective Protection of allyl OH

In another embodiment, selective insertion of the phosphocholine moiety at C-1 of a ceramide proceeds by protecting the allylic hydroxyl group at C-3 with an ester, such as, but not limited to, an acetoxy ester, a benzoyl ester or a pivaloyl ester or with an ether, such as, but not limited to, a tris(trimethyl)silyl ether, a t-butyl(dimethyl)silyl ether, a t-butyldiphenylsilyl ether, or a tetrahydropyranylether. As such multiple protection steps produce occasional migration of acyl or silyl protecting groups from C-3 to C-1 resulting in mixtures of protected ceramides, temperature and other reaction conditions can be monitored to keep any undesired transesterification under 10%.

Synthesis of N-acyl D-erythro-sphingomyelin without Protection of the Secondary Hydroxyl Group In certain embodiments of the invention, N-acyl D-erythro-sphingosine is directly phosphitylated with ethylene halophosphite as shown in Scheme XIII. The reaction proceeds in the presence of about 2.5-3.5 equivalents of ethylene halophosphite in the presence of about 4-10 equivalents of a base in an aprotic polar solvent having a large dielectric constant (>20) and a large dipole moment. In certain embodiments, the reaction proceeds at about −20 to +20° C. In certain embodiments, the aprotic polar solvent has a dielectric constant greater than 20. In certain embodiments, the aprotic polar solvent is chloroform, nitromethane, acetonitrile, acetone, dimethyl sulfoxide, or mixtures thereof. In certain embodiments, the halophosphite is chlorophosphite. In further embodiments, the reaction proceeds with 3 equivalents of ethylene chlorophosphite. In other embodiments, the base is N,N-diisopropylethylamine. In yet other embodiments the reaction proceeds with 5 eq N,N-diisopropylethylamine.

Without being bound to any particular mechanism, it is believed that such a solvent hinders, by solvation of the hydroxyl moieties, the intramolecular hydrogen bonding in the acyl ceramide. Suitable solvents include, but not limited to: chloroform, nitromethane, acetonitrile, acetone, or dimethyl sulfoxide.

After quenching the unreacted ethylene halophosphite with an alcohol, the cyclic phosphite is simultaneously oxidized and the ring opened in the presence of bromine at temperatures between about −50 to 10° C. (preferably about −20° C.) to produce the N-acyl-ceramide bromide derivative, whose P—Br bond is hydrolyzed by the addition of water. In particular embodiments of the invention the alcohol is methanol or ethanol. The ceramide 1-(2'-bromoethyl) phosphate ester derivative is quaternized with anhydrous liquid trimethylamine to afford the N-acyl D-erythro-sphingomyelin. In further embodiments of the invention the N-acyl D-erythro-sphingosine is N-palmitoyl-D-erythro-sphingosine.

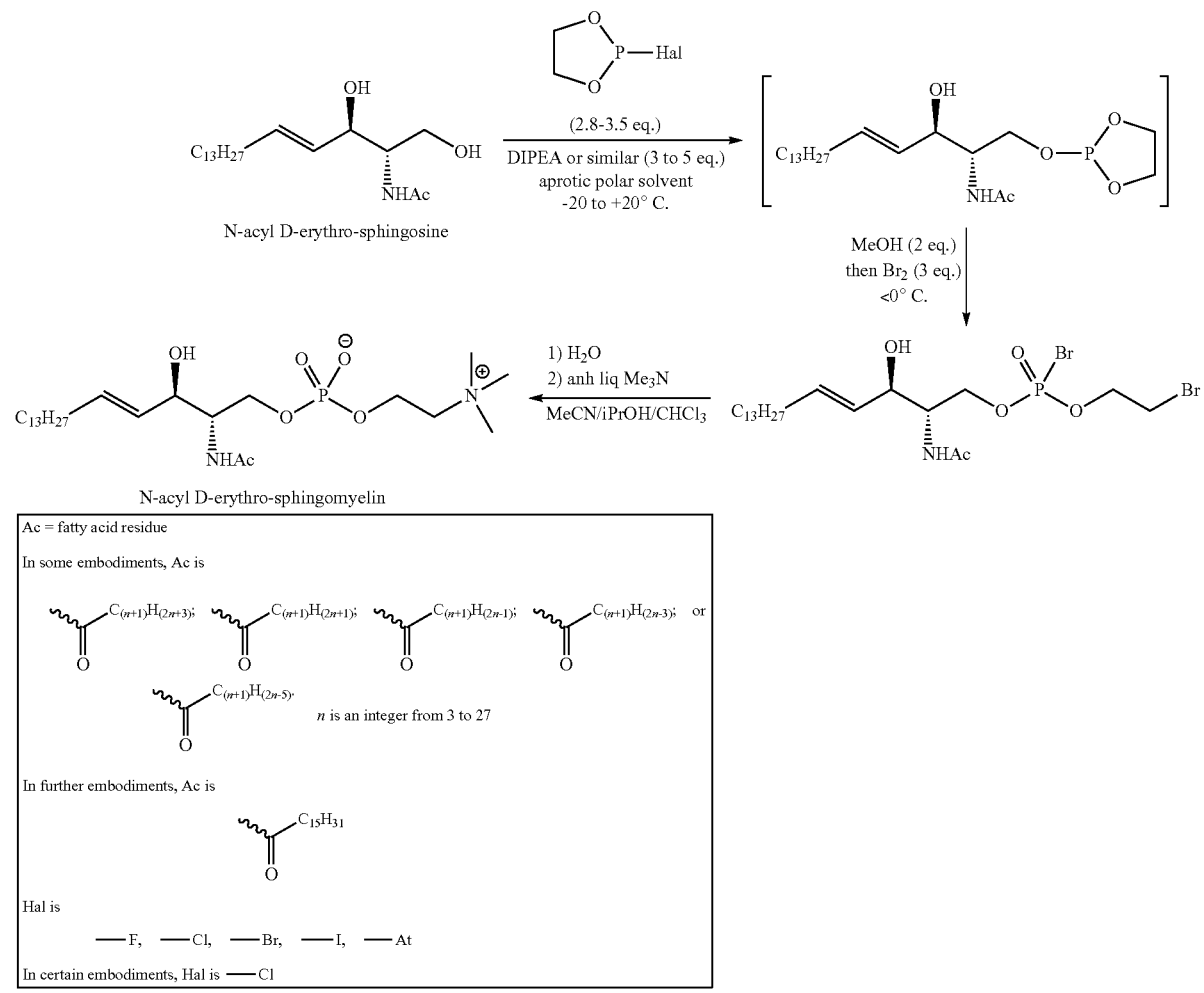

Synthesis of N-acyl D-erythro-dihydrosphingomyelin without Protection of the Secondary Hydroxyl Group In certain embodiments of the invention, N-acyl D-erythro-dihydrosphingosine is directly phosphitylated with ethylene halophosphite as shown in Scheme XIV. The reaction proceeds in the presence of about 2.5-3.5 equivalents of ethylene halophosphite in the presence of about 4-10 equivalents of a base in an aprotic polar solvent having a large dielectric constant (>20) and a large dipole moment. In certain embodiments, the reaction proceeds at about −20 to +20° C. In certain embodiments, the aprotic polar solvent has a dielectric constant greater than 20. In certain embodiments, the aprotic polar solvent is chloroform, nitromethane, acetonitrile, acetone, dimethyl sulfoxide, or mixtures thereof. In particular embodiments, the halophosphite is ethylene chlorophosphite. In further embodiments, the reaction proceeds with 3 equivalents of ethylene chlorophosphite. In other embodiments, the base is N,N-diisopropylethylamine. In yet other embodiments the reaction proceeds with 5 eq N,N-diisopropylethylamine.

Without being bound to any particular mechanism, it is believed that such a solvent hinders, by solvation of the hydroxyl moieties, the intramolecular hydrogen bonding in the acyl dihydroceramide. Suitable solvents include, but not limited to: chloroform, nitromethane, acetonitrile, acetone, or dimethyl sulfoxide.

After quenching the unreacted ethylene halophosphite with an alcohol the cyclic phosphite is simultaneously oxidized and the ring opened in the presence of bromine at temperatures between about −50 to 10° C. (preferably about −20° C.) to produce the N-acyl-dihydroceramide bromide derivative, whose P—Br bond is hydrolyzed by the addition of water. In particular embodiments of the invention the alcohol is methanol or ethanol. The dihydroceramide-C16 1-(2'-bromoethyl)phosphate ester derivative is quaternized with anhydrous liquid trimethylamine to afford the N-acyl-dihydrosphingomyelin. In further embodiments of the invention the N-acyl D-erythro-dihydrosphingosine is N-palmitoyl-D-erythro-dihydrosphingosine.

Example 1

Synthesis of N-Palmitoyl-D-erythro-sphingomyelin via (1R,2R,5R)-(+)-2-hydroxy-3-Pinanone Step 1: Synthesis of 2-(E)-Hexadecenal Step 1.1: 1-Tetradecanal

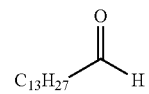

To a solution of 1-tetradecanol (110.0 g; 0.513 mol) and trichloroisocyanuric acid (178.1 g; 0.77 mol) in methylene chloride (1500 ml) at −30° C. was added (2,2,6,6-Tetramethylpiperidin-1-yl)oxy (TEMPO) (800 mg; 0.051 mol). The reaction mixture was stirred for 1.5 h at 0° C. and filtered on celite. The organic phase collected was then washed with a saturated solution of $Na_2CO_3$ (800 ml) followed by HCl 1N (800 mL). It was then dried over Scheme XIV

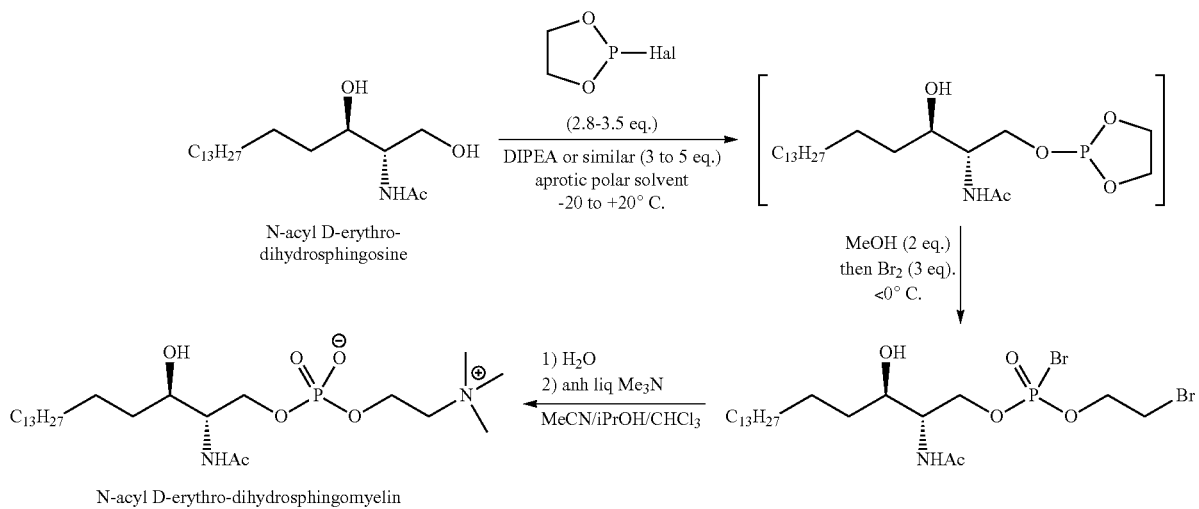

N-acyl D-erythro-dihydrosphingomyelin

Ac = fatty acid residue

In some embodiments, Ac is

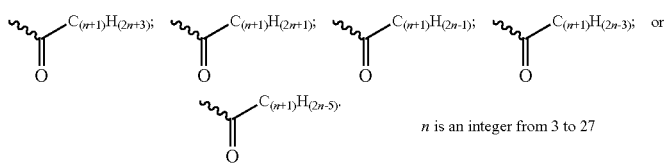

n is an integer from 3 to 27

In further embodiments, Ac is

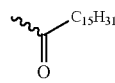

Hal is

—F, —Cl, —Br, —I, —At

In certain embodiments, Hal is —Cl

MgSO$_4$, filtered and concentrated under vacuum to give rise to the title compound as white solid (99.6 g; 91%).

Step 1.2: Ethyl-2-Hexadecenoate

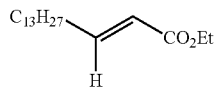

To a suspension of NaH (2.4 g, 0.059 mol) in anhydrous tetrahydrofuran (40 mL) triethylphosphonoacetate (9.4 mL, 0.047 mol) was added, dropwise, at 0° C. After stirring for 30 minutes at 0° C., a solution of tetradecanal (10.0 g, 0.047 mol) in tetrahydrofuran (40 mL) was added and the reaction mixture was warmed to room temperature and stirred for an additional 3 h. A saturated solution of NaCl (50 mL) was then added and the aqueous layer was extracted with Et$_2$O (3×200 mL). The organic layers were gathered, dried over MgSO$_4$ and filtered, and the solvents were evaporated. The resulting product was purified by flash chromatography on silica gel (heptane-ethyl acetate: 95/5) to give the title compound as a colorless liquid (12.3 g; 92%).

Rf=0.24 (Hexane/Et$_2$O: 95/5).

GC: tr=13.13 min (triethylphosphonoacetate); tr=15.80 min (1-tetradecanal); tr=20.60 min (ethyl 2-Hexadecenoate)

$^1$H NMR (400 MHz, CDCl$_3$): 0.87 (t, 3H, CH$_3$); 1.25 (br, 20H); 1.28 (t, 3H, CH$_3$); 1.44 (m, 2H, CH$_2$); 2.18 (qd, 2H, CH$_2$, $^3$J=6.5 Hz, $^4$J=1.5 Hz); 4.18 (q, 2H, CH$_2$); 5.80 (dt, 1H, $^3$J=15.5 Hz, $^4$J=1.5 Hz); 6.96 (dt, 1H, CH$_2$, $^3$J=15.5 Hz, $^3$J=6.5 Hz).

Step 1.3: 2-(E)-Hexadecen-1-ol

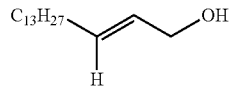

Diisobutylaluminium hydride (54.5 mL, 1 M in cyclohexane, 0.054 mol) was added, drop-wise at a 0° C., to a solution of ethyl-2-hexadecenoate (6.4 g, 0.023 mol) in tetrahydrofuran (20 mL). The reaction mixture was stirred at 0° C. until complete consumption of the starting material as monitored by TLC. Et$_2$O (50 mL) and a saturated solution of sodium tartrate (50 mL) were successively added while stirring until 2 separate layers were distinctly visible. The aqueous layer was extracted with Et$_2$O (2×50 mL). The organic layers were combined and dried over MgSO$_4$, and the solvents removed under vacuum to give the title compound as a white waxy solid (5.3 g; 97%).

Rf=0.31 (Hexane/Et$_2$O: 1/1).

GC: tr=19.1 min $^1$H NMR (200 MHz, CDCl$_3$): 0.87 (t, 3H, CH$_3$); 1.25 (br, 22H); 2.03 (q, 2H, CH$_2$, $^3$J=6.0 Hz); 4.09 (d, 1H, $^3$J=5 Hz); 5.66 (m, 2H).

Step 1.4: 2-(E)-Hexadecen-1-al

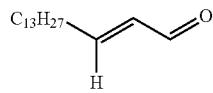

To a solution of 2-(E)-Hexadecen-1-ol (5.2 g; 0.022 mol) in methylene chloride (30 mL) under argon at 0° C. a suspension of pyridinium chlorochromate (PCC) (16.3 g; 0.043 mol) in methylene chloride (30 mL) followed by celite (20 g) was added. After stirring for 3 h at 0° C., the reaction mixture was diluted with 20 mL of diethyl ether, and filtered over a pad of silica. Solvents were evaporated and the crude product was purified by flash chromatography on silica gel (heptane-ethyl acetate: 95/5) to give the title compound as a white solid (2.2 g; 43%).

Rf=0.14 (Hexane/Et$_2$O: 95/5)

GC: tr=18.9 min $^1$H NMR (200 MHz, CDCl$_3$): 0.88 (t, 3H, CH$_3$); 1.26 (br, 20H); 1.50 (m, 2H, CH$_2$); 2.35 (qd, 2H, $^3$J=7 Hz, $^4$J=1.5 Hz); 6.1 (ddt, 1H, $^3$J=15.5 Hz, $^3$J=8 Hz, $^4$J=1.5 Hz); 6.85 (td, 1H, $^3$J=15.5 Hz, $^3$J=7 Hz); 9.5 (d, 1H, $^3$J=8 Hz).

Step 2: Synthesis of (1R,2R,5R)-(+)-2-Hydroxy-3-Pinanone

Step 2.1: (1R,2R,3S,5R)-(−)-Pinanediol

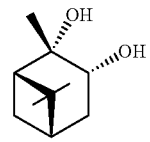

S-(−)-α-pinene (24.3 g; 0.18 mol), potassium osmate dihydrate (0.13 g), N-methylmorpholine-N-oxide (60% in water; 0.21 mol; 41.7 g) dissolved in 17.3 mL of pyridine, 107 mL of acetone and 11.9 mL of deionized water were combined in a 250 mL three-necked flask. The reaction mixture was refluxed for 60 hours and then diluted with methyl tert-butyl ether (MTBE) (300 mL) and hexane (60 mL). Water (200 mL) was then added and the organic layer was decanted, washed successively with 10% citric acid (3×100 mL), a saturated solution of NaHCO$_3$ (100 mL), brine (100 mL), and then dried over MgSO$_4$ and filtered. The solvents were removed under vacuum to give the title compound as a dark orange oil (24.5 g).

GC: tr=12.0 min (diol) tr=10.9 min (1R,2R,5R)-(+)-2-hydroxy-3-pinanone; (5-10%)

Step 2.2: (1R,2R,5R)-(+)-Hydroxy-3-Pinanone

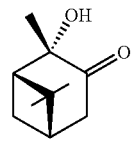

Triethylamine (Et$_3$N) (80.2 mL; 0.58 mol) was added to a solution of (1R,2R,3S,5R)-(−)-Pinanediol (24.5 g; 143.9 mmol) in a dimethyl sulfoxide/methylene chloride solvent mixture (154 mL; 1/1) at 10° C. SO$_3$.Pyridine (68.7 g; 0.43 mol) was then added portion-wise over 30 minutes while the temperature was maintained below 20° C. The reaction mixture was stirred for 2 hours at 10° C. then diluted with ethyl acetate (300 mL). The organic layer was washed with HCl 0.5 N (2*150 mL), brine (150 mL), then dried over MgSO$_4$ and filtered. The solvents were removed under vacuum to give a brown oil. The crude product was purified by flash chromatography on silica gel (methylcyclohexane-ethyl acetate: 9/1) to give the title compound as a yellow oil (19.2 g; 63% over two steps).

GC: tr=10.9 min;
Distillation: B.p=100-104° C. (3-4 mmHg)
$^1$H NMR (400 MHz, CDCl$_3$): 0.90 (s, 3H); 1.30 (s, 3H); 1.40 (s, 3H); 1.70 (d, 1H, J=12.0 Hz); 2.10 (m, 2H); 2.30 (s, 1H); 2.50 (m, 1H); 2.60 (brs, 2H).

Step 3: D-erythro-Sphingosine hydrochloride

Step 3.1: (1R,2R,5R)-Ethyl-((2-hydroxypinan-3-ylene)amino)acetate

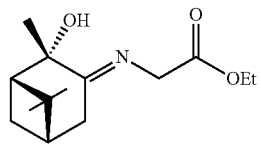 [SMILES: CCOC(=O)C/N=C1\C[C@@H]2C[C@@H](C2(C)C)[C@]1(C)O]

NH$_3$ gas was bubbled through a suspension of ethylglycinate hydrochloride (16.6 g; 0.13 mol) in toluene (100 mL) for 1 h. The ammonium chloride formed was filtered off and (1R,2R,5R)-(+)-2-hydroxy-3-pinanone (Step 2.2) (10.0 g; 0.59 mol) was added to the solution of free base ethylglycinate with few drops of BF$_3$.OEt$_2$. The reaction mixture was then refluxed for 5 hours with a Dean-Stark apparatus. After completion of the reaction, the solvents were evaporated. The resulting product was purified by flash chromatography on silica gel impregnated with Et$_3$N (5% in ether) and the title compound was eluted with Et$_2$O.

Rf=0.35 (Cyclohexane-ethyl acetate: 1/1)
$^1$H NMR (CDCl$_3$): 0.88 (s, 3H, CH$_3$); 1.30 (t, 3H, CH$_3$, J=7.0 Hz); 1.34 (s, 3H, CH$_3$); 1.53 (s, 3H, CH$_3$); 1.57 (d, 1H, J=10.0 Hz); 2.07 (m, 2H); 2.36 (dtt, 1H, J=10.0 Hz; J=6.0 Hz; J=1.5 Hz); 2.50 (d, 2H, J=1.5 Hz; J=1.0 Hz); 2.61 (s, 1H, OH); 4.17 (s, 2H, =N—CH$_2$); 4.23 (q, 2H, CH$_2$CH$_3$, J=7.0 Hz).

NMR $^{13}$C (CDCl$_3$) δ (ppm): 180.0 (C-1 quat. Ester); 170.2 (C-1' quat. amide); 76.5 (C-2' quat.); 60.9 (CH$_2$—CH$_3$); 52.6 (C-2); 50.4 (C-3'); 38.6 (C quat); 38.3 (C-5); 33.7 (C-6); 28.2 (CH$_3$); 28.1 (C-4'); 27.3 (CH$_3$); 22.8 (CH3); 14.2 (CH$_2$—CH$_3$).

Step 3.2 (2S,3R,E)-ethyl 3-hydroxy-2-((E)-((1S,2S,5S)-2-hydroxy-2,6,6-trimethylbicyclo[3.1.1]heptan-3-ylidene)amino)octadec-4-enoate and (2S,3R,E)-isopropyl 3-hydroxy-2-((E)-((1S,2S,5S)-2-hydroxy-2,6,6-trimethylbicyclo[3.1.1]heptan-3-ylidene)amino)octadec-4-enoate

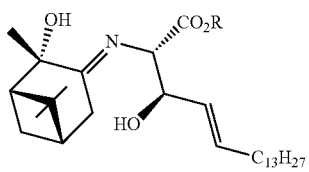

R = Et
R = iPr

A solution of chloro titanium isopropoxyde (5.2 g; 0.02 mol) in methylene chloride (15 mL), a solution of 2-(E)-Hexadecen-1-al (4.35 g; 0.0018) in methylene chloride (8 mL) and triethylamine (6.1 mL; 0.044 mol) was added to a solution of (1R,2R,5R)-Ethyl-((2-hydroxypinan-3-ylene)amino)acetate (5.0 g; 0.020 mol) in methylene chloride (9.6 mL) under argon at 0° C. After stirring the reaction mixture for 4 h at 0° C., it was then quenched with brine (25 mL). The aqueous layer was extracted with ethyl acetate and dried over MgSO$_4$; the solvents were removed under vacuum to give rise to a yellowy-orange oil (9.7 g), mixture of the 73/27 isopropyl and ethyl esters.

Rf=0.7 (Cyclohexane-ethyl acetate: 1/1)
'H NMR (CDCl$_3$) δ (ppm): 0.88 (t, 3H, J=6.5 Hz); 1.50-1.10 (m, 28H, (CH$_2$)$_{12}$+2CH$_3$); 1.50 (s, 3H, CH$_3$); 1.53 (d, 1H); 2.13 (q, 2H); 2.18-1.95 (m, 2H); 2.34 (dtd, 1H); 2.51 (m, 1H); 3.25 (s, 1H); 3.75 (s, 1H); 4.15 (d, 1H, J=6.7 Hz); 4.20 (dt, 1H, J=7.0 Hz; J=4.0 Hz); 4.55 (t, 1H, J=6.7 Hz); 5.05 (hept, 1H, J=6.3 Hz, CH(CH$_3$)$_2$); 5.55 (dd, 1H, J=15.4 Hz; J=7.1 Hz); 5.70 (dt, 1H, J=15.4 Hz; J=6.5 Hz).

Step 3.3: (2R,3R,E)-ethyl 2-amino-3-hydroxyoctadec-4-enoate and (2R,3R,E)-isopropyl 2-amino-3-hydroxyoctadec-4-enoate

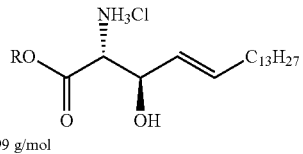

R = ET MW = 377.99 g/mol
R = iPr MW = 392.02 g/mol

HCl 1.2 M (203 mL) was added dropwise to the crude aldol product (14.8 g; 0.030 mol) in tetrahydrofuran (51 mL). The mixture was then stirred for 72 h at rt. Tetrahydrofuran was evaporated and the aqueous layer was then extracted with ethyl acetate. The organic layer contained, after removal of the solvents and (+)-2-hydroxy-3-pinanone (6.8 g). The aqueous layer was dried to give rise to the desired aminoester hydrochloride (5.7 g).

Rf=0.45 (Et$_2$O-MeOH: 96/4)

Step 3.4: D-erythro-Sphingosine hydrochloride

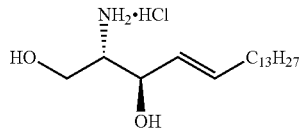

Sodium borohydride (4.40 g; 0.12 mol) was added to a suspension of the aminoester hydrochloride from the step above (2.2 g; 0.0058 mol) in 40 mL of a solvent mixture of EtOH/H$_2$O (3/1). The mixture was stirred for 72 h at 0° C. before a saturated solution of NH$_4$Cl (40 mL) was added. The aqueous layer was extracted with methylene chloride (4*100 mL), washed with brine, dried over MgSO$_4$, and filtered. The solvents were removed under vacuum to give rise to the title compound as a white solid (1.5 g; 86%).

Rf=0.3 (CHCl$_3$-MeOH—H$_2$O: 13/6/1)
'H NMR (CDCl$_3$) δ (ppm) 0.90 (t, 3H, J=6.5 Hz); 1.50-1.20 (m, 22H, (CH$_2$)$_{12}$); 2.00 (q, 2H, J=7.8 Hz); 3.15 (s, 1H, OH); 3.70 (m, 4H); 4.30 (s, 1H, OH); 5.40 (dd, 1H, J=15.5 Hz; J=6.3 Hz); 5.80 (dt, 1H, J=15.5 Hz; J=7.8 Hz); 8.46 (brs, 3H).

Step 4: D-erythro-Ceramide-C16

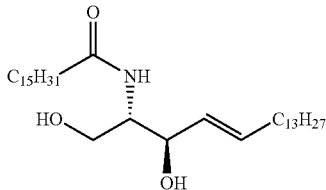

Palmitic acid (1.9 g; 0.074 mol) and a solution of sphingosine (2.2 g; 0.074 mol) in tetrahydrofuran (99 mL) were successively added to a suspension of O-(Benzotriazol-1-yl)-N,N,N',N'-tetramethyluronium hexafluorophosphate (3.1 g; 8.1 mmol) in dimethylformamide (15 mL). The white suspension obtained was cooled to 0° C. and triethylamine (2.5 mL; 0.018 mmol) was added. The reaction mixture was stirred for 12 h at room temperature. A solution of 5% citric acid (400 mL) was then added and the suspension was filtered off. The white solid was mixed with water (60 mL) at rt, filtered off and washed with water. It was then dried under vacuum at 40° C. to give the title compound (3.5 g; 80%).

$^1$H NMR (CDCl$_3$): 0.97 (6H, t); 1.10-1.40 (m, 46H); 1.62 (2H, m); 2.04 (2H, m, CH$_2$—CH); 2.21 (t, 2H, J=8.2 Hz, CH$_2$CONH); 2.71 (m, 2H); 3.69 (m, 1H); 3.80-4.00 (m, 2H); 4.28 (m, 1H, CH(OH)CH); 5.52 (ddt, 1H, J=15.4 Hz; J=6.4 Hz; J=1.0 Hz, CH(OH)CH); 5.77 (dtd, 1H, J=15.4 Hz; J=6.7 Hz; J=1.1 Hz, CH$_2$CH); 6.22 (d, 1H, J=6.8 Hz, NH).

Step 5: 3-O-Benzoyl-N-Palmitoyl-D-erythro-sphingosine

Step 5.1: 1-O-trityl-D-erythro-ceramide C-16

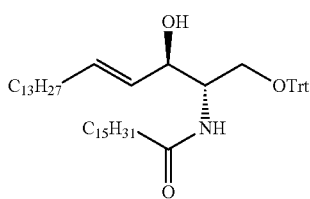

A suspension of D-erythro-ceramide-C16 (0.58 g, 1.08 mmol), triethylamine (1.2 ml), 4-dimethylaminopyridine (5 mg), and trityl chloride (0.45 g, 1.62 mmol) in methylene chloride (14 ml) was heated at reflux for 60 h. Volatile materials were evaporated, the residue was re-dissolved in ethyl acetate and the mixture was washed successively with 1 M hydrochloric acid, aq. NaHCO$_3$ and brine. The organic phase was dried over MgSO$_4$ and evaporated. The residue was chromatographed on silica gel in heptane/ethyl acetate (7:3) to afford 1-O-trityl-D-erythro-ceramide-C16 (0.39 g, 46%) as a waxy solid.

Rf=0.49 (CH$_2$Cl$_2$/ethyl acetate/Et$_3$N: 97/3/0.1)

$^1$H NMR (CDCl$_3$) δ 0.88 (6H, t), 1.40-1.15 (46H, m), 1.64 (2H, m), 1.91 (2H, m), 2.20 (2H, t, J=8.2 Hz), 3.28 (1H, dd, J=9.6 Hz, J=4.0 Hz), 3.40-3.35 (2H, m), 4.04 (1H, m), 4.17 (1H, m), 5.24 (1H, dd, J=15.4 Hz, J=6.2 Hz), 5.62 (1H, dt, J=15.4 Hz, J=6.6 Hz), 6.06 (1H, d, J=7.5 Hz, NH), 7.35-7.20 (9H, m), 7.35-7.45 (6H, m).

Step 5.2: 3-O-Benzoyl-1-O-trityl-D-erythro-ceramide-C16

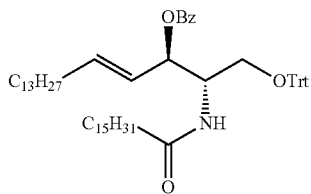

4-Dimethylaminopyridine (10 mg) and benzoyl chloride (0.1 ml, 0.85 mmol) was added to a solution of 1-O-trityl-D-erythro-ceramide-C16 (0.39 g, 0.50 mmol) in pyridine (5 ml) under nitrogen were added and the mixture was stirred for 20 h. Solvent was removed under reduced pressure and the residue was partitioned between aq. NaHCO$_3$ and ethyl acetate. The organic phase was washed with brine, dried (MgSO$_4$), and evaporated, and the residue chromatographed on silica gel in Heptane/Ethyl acetate-hexane (85:15 to 1:1) to give the title compound (207 mg, 60%) as a waxy solid.

$^1$H NMR (CDCl$_3$) δ 0.88 (6H, t), 1.31-1.23 (46H, m), 1.56 (2H, m), 1.99 (2H, m), 2.08 (2H, t), 3.17 (1H, dd, J=7.4 Hz, J=3.9 Hz, CH(H')OH), 3.43 (1H, dd, J=9.7 Hz, 3.9 Hz, CH(H')OH], 4.47 (1H, m, CH—(NHCOR)), 5.43 [1H, dd, J=15.3 Hz, J=7.3 Hz, CH(OCOPh)CH=], 5.75-5.60 [2H, m, NH, CH(OCOPh)], 5.86 (1H, dt, J=15.3 Hz, J=7.9 Hz, CH$_2$CH=), 7.25-7.10 (9H, m), 7.40-7.30 (8H, m), 7.54 (1H, t, J=7.5 Hz), 7.92 (2H, d, J=7.3 Hz).

Step 5.3: 3-O-Benzoyl-D-erythro-ceramide-C16

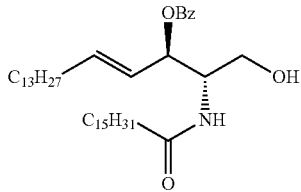

A solution of 3-O-Benzoyl-1-O-trityl-D-erythro-ceramide-C16 (1.10 g, 1.24 mmol) and toluene-p-sulfonic acid monohydrate (0.23 g, 1.36 mmol) in methylene chloride (18 ml) and methanol (18 ml) was stirred under nitrogen for 3 h. Solvent was evaporated and the residue was partitioned between aq. NaHCO$_3$ and ethyl acetate. The organic phase was washed with brine, dried over MgSO$_4$, and evaporated to dryness. The residue was chromatographed on silica gel and eluted with Heptane/Ethyl acetate (1:1) to give the title compound (0.64 g; 80%).

$^1$H NMR (CDCl$_3$/CD$_3$OD) δ 0.87 (6H, t), 1.30-1.10 (46H, m), 1.54 (2H, m), 1.96 (2H, m), 2.14 (2H, m), 2.77 (2H, br s), 3.71 (2H, m, CH$_2$O), 4.24 (1H, m, CHN), 5.60-5.40 [2H, m, CH(OCOPh)CH=], 5.79 (1H, dt, J=15.0 Hz, J=6.8 Hz, CH$_2$CH=), 6.18 (1H, d, J=9.6 Hz, NH), 7.38 (2H, dd, J=7.6 Hz, J=7.2 Hz), 7.52 (1H, dd, J=7.6, J=7.6 Hz), 7.96 (1H, d, J=7.2 Hz).

Step 6: N-Palmitoyl-D-erythro-Sphingomyelin

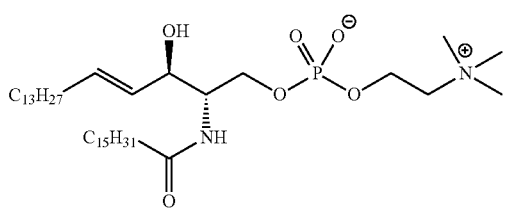

A solution of 3-O-Benzoyl-D-erythro-ceramide-C16 (0.2 g, 0.31 mmol) and tetramethylethylenediamine (TMEDA) (51 µL, 0.53 mmol) in dry toluene (5 ml) was cooled to about 8° C. To this solution 2-chloro-2-oxo-1,3,2 dioxaphospholane (82 mg, 0.57 mmol) in 0.1 mL of acetonitrile was added dropwise. The mixture was then warmed to room temperature and stirred for 4 h. Acetonitrile (5 mL) was added, followed by anhydrous trimethylamine. The flask was heated to 65-70° C. for 14 h. The system was then cooled to room temperature and the flask was opened. The solvents were removed under reduced pressure.

The resulting product, 3-O-Benzoyl-N-Palmitoyl-D-erythro-sphingomyelin, was dissolved in methanol (1.5 mL). Sodium methoxide (30% in methanol, 15 µL) was added to the solution. After stirring overnight, methylene chloride and water were added. The pH was adjusted to and the organic layer was evaporated to dryness. The crude material was purified by column chromatography to give the title compound, N-palmitoyl-D-erythro-sphingomyelin (66 mg, 30% over 3 steps).

$^1$H NMR (CDCl$_3$/CD$_3$OD) δ: 0.90 (t, J=7.1 Hz, 6H), 1.26 (m, 46H), 1.56 (m, (C=O)CH$_2$CH$_2$, 2H), 1.99 (m, CH=CHCH$_2$, 2H), 2.14 (t, (C=O)CH$_2$, 2H), 3.24 (s, N(CH$_3$)$_3$, 9H),), 3.68 (m, POCH$_2$CH$_2$N, 2H), 3.91 (m, POCH$_2$CH, 2H), 4.04 (t, CHO, 4H, J=7.7 Hz), 4.14 (m, CHN, 2H), 4.28 (m, POCH$_2$CH$_2$N, 2H), 5.44 (ddt, J=15.4 Hz, J=7.6 Hz, J=1.5 Hz, 2H), 5.71 ddt, J=15.4 Hz, J=6.6 Hz, J=0.5 Hz, 1H).

Example 2

Lab-Scale Synthesis of N-Palmitoyl-D-Erythro-Sphingomyelin Starting from D-erythro-Sphingosine Step 1: D-erythro-Ceramide-C16

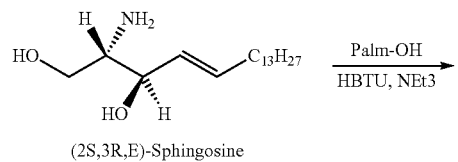

(2S,3R,E)-Sphingosine

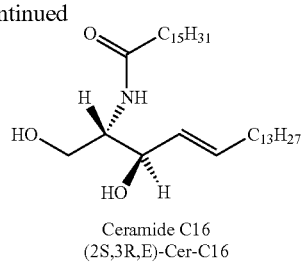

Ceramide C16
(2S,3R,E)-Cer-C16

Palmitic acid (17.12 g, 66.8 mmol) and D-erythro-sphingosine (20 g, 66.8 mmol) in tetrahydrofuran (890 ml) were added to a suspension of O-Benzotriazole-N,N,N',N'-tetramethyl-uronium-hexafluoro-phosphate (27.84 g, 73.4 mmol) in 140 ml dimethylformamide. The obtained white suspension was cooled at 0-5° C., 22.5 ml (160.7 mmol) triethylamine was added over the course of 30-60 min, and the mixture was stirred at room temperature for 12 h. After this time the thin layer chromatography (TLC) analysis indicated >99% conversion to D-erythro-ceramide-C16. Citric acid 5% (400 ml) was added, the mixture was stirred for 30 min at 0-5° C. and the obtained suspension was filtered. The white cake was suspended in water (600 ml) at room temperature. The suspension was filtered and washed with water. Drying for 12 hours at reduced pressure at 40° C. gave 32.4 g (yield 90%) of D-erythro-ceramide-C16. Purity by HPLC was 98.1% and by HPTLC 99.2%.

$^1$H NMR (≙ ppm, CDCl$_3$): 0.97 (6H, t), 1.1-1.4 (46H, m), 1.62 (2H, m), 2.04 (2H, m, CH$_2$CH), 2.21 (2H, t, J 8.2 Hz, CH$_2$CONH), 2.71 (2H, m), 3.69 (1H, m), 3.8-4.0 (2H, m), 4.28 (1H, m, CH(OH)CH), 5.52 (1H, ddt, J 15.4, 6.4, 1.0 Hz, CH(OH)CH)), 5.77 (1H, dtd, J 15.4, 6.7, 1.1 Hz, CH$_2$CH), 6.22 (1H, d, J=6.8 Hz, NH).

Step 2: 3-O-Benzoyl-D-erythro-ceramide-C16

Scheme N

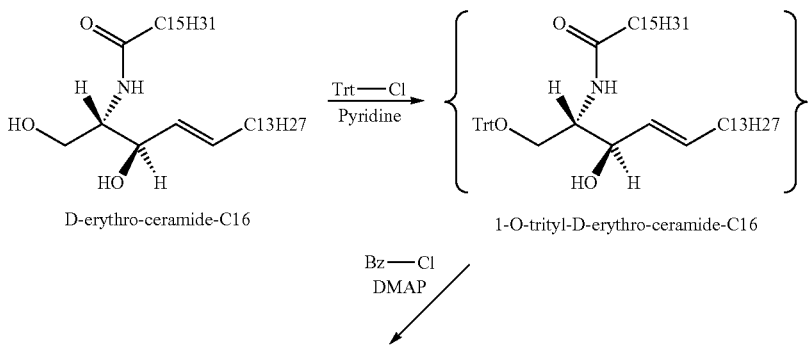

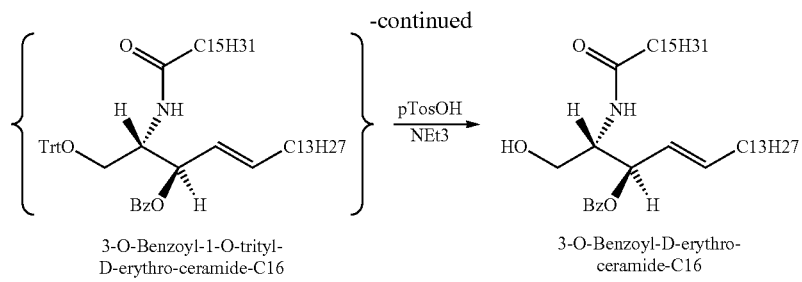

3-O-Benzoyl-1-O-trityl-
D-erythro-ceramide-C16 → 3-O-Benzoyl-D-erythro-ceramide-C16

Step 2.1
N-palmitoyl-1-O-trityl-D-erythro-sphingosine

A suspension of D-erythro-ceramide-C16 (16.30 g, 30.3 mmol), pyridine (250 ml), and trityl chloride (10.15 g, 36.4 mmol) in toluene (150 ml) was heated at 52° C. for 12 h. TLC analysis after the 12 hours indicated a greater than 90% conversion to 1-O-trityl-D-erythro-ceramide-C16, with about 5% unreacted D-erythro-ceramide-C16 and about 2-5% N-palmitoyl D-erythro 1-O-Trityl-3-O-trityl-1-sphingosine. The suspension was cooled to 0-5° C. and filtered to remove some salts.

Step 2.2:
3-O-Benzoyl1-O-trityl-D-erythro-ceramide-C16

4-Dimethylaminopyridine (560 mg, 4.54 mmol) and benzoyl chloride (5.8 ml, 50 mmol) was added to a solution of the product from the above step and the mixture was stirred at 0-5° C. for 15 h. After 15 hours the TLC analysis indicated a greater than 97% conversion to 3-O-Benzoyl-1-O-trityl-D-erythro-ceramide-C16. The reaction mixture was partitioned between water (130 ml) and ethyl acetate (530 ml). The organic phase was washed 4 times with water (160 ml) to reach pH 7. The organic phase was evaporated at reduced pressure and the resulting the oily yellow residue (34 g) was dissolved in methylene chloride (300 ml) and methanol (300 ml) at 5° C. and used directly for the subsequent detritylation step.

Step 2.3: 3-O-Benzoyl-D-erythro-ceramide-C16

Toluene-p-sulfonic acid monohydrate (2.88 g, 15.15 mmol) was added to the above solution of 3-O-Benzoyl-1-O-trityl-D-erythro-ceramide-C16 in methylene chloride/methanol. The mixture was stirred at 18-22° C. for 3 h. After 3 hours the TLC analysis indicated greater than 97% conversion to 3-O-Benzoyl-D-erythro-ceramide-C16. The reaction mixture was neutralized at 0-5° C. with 2.58 ml triethylamine, and the methylene chloride was evaporated (40° C./340 mbar). The obtained residue was stirred at 0-5° C. for 1 h. The suspension was filtered off, washed with methanol and dried at 35° C. for 12 h, yielding 21.9 g (113%) of crude product (3-O-Benzoyl-D-erythro-ceramide-C16).

Recrystallization was performed with methanol (500 ml) and methylene chloride (5 ml) at 42° C., the solution was stirred at 20-22° C. for 1 h and then cooled to 0-5° C. for 1 h. After filtration, the resulting cake was washed with methanol (2×50 ml) and dried for 12 h at 35° C. under reduced pressure yielding 13.6 g of 3-O-Benzoyl-D-erythro-ceramide-C16 contaminated with 13% of the unprotected ceramide. The crystallized material was further purified by column chromatography on 185 g silica gel. It was eluted with 2.2 L hexane/ethyl acetate 5/1, 2.2 L hexane/ethyl acetate 3/1 and finally 4.4 L hexane/ethyl acetate 2/1. The product containing fractions were combined and evaporated to dryness at 40° C. resulting in 12.1 g (yield 62%). Purity by HPLC was 97.7% and by HPTLC 99.6%.

$^1$H NMR ($\triangleq$ ppm, CDCl$_3$): 0.87 (6H, t), 1.1-1.3 (46H, m), 1.54 (2H, m), 1.96 (2H, m), 2.14 (2H, m), 2.77 (2H, br s), 3.71 (2H, m, CH$_2$O), 4.24 (1H, m, CHN), 5.4-5.6 (2H, m, CH(OCOPh)CH=), 5.79 (1H, dt, J 15.0, 6.8 Hz, CH$_2$CH=), 6.18 (1H, d, J=9.6 Hz, NH), 7.38 (2H, dd, J 7.6, 7.2 Hz), 7.52 (1H, dd, J 7.6, 7.6 Hz), 7.96 (1H, d, J 7.2 Hz)

Step 3:
3-O-Benzoyl-N-palmitoyl-D-erythro-sphingomyelin

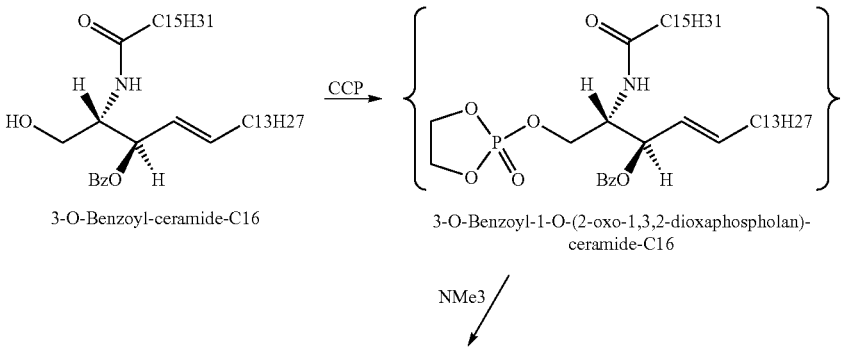

3-O-Benzoyl-ceramide-C16 → 3-O-Benzoyl-1-O-(2-oxo-1,3,2-dioxaphospholan)-ceramide-C16

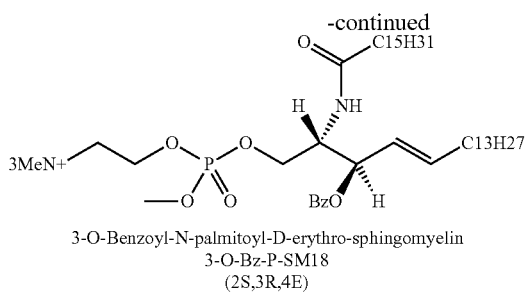

3-O-Benzoyl-N-palmitoyl-D-erythro-sphingomyelin
3-O-Bz-P-SM18
(2S,3R,4E)

Step 3.1: 3-O-Benzoyl-1-O-(2-oxo-1,3,2-dioxaphospholan)-ceramide-C16

3-O-Benzoyl-D-erythro-ceramide-C16 (9.49 g, 14.8 mmol) was nearly completely dissolved in toluene (200 ml) and charged into a pressure reactor. Tetramethylethylenediamine (2.4 ml, 15.8 mmol) was added to the mixture. The mixture was cooled to 7° C. followed by the addition of a solution of 2-chloro-2-oxo-1,3,2-dioxaphospholane (CCP) (3.90 g, 27.3 mmol) in acetonitrile (5 ml). After two hours at 7° C. the reaction was warmed to 21° C. for two hours. TLC analysis indicated greater than 97% conversion of 3-O-Benzoyl-D-erythro-ceramide-C16 to the intermediate 3-O-Benzoyl-1-β-(2-oxo-1,3,2-dioxaphospholan)-ceramide-C16.

Step 3.2: 3-O-Benzoyl-N-palmitoyl-D-erythro-sphingomyelin

Acetonitrile (200 ml) was introduced into the reactor followed by gaseous trimethylamine until a constant pressure of 0.5-0.7 bar was reached. During heating to 67° C. the pressure rose to 1.8-2.0 bar. After 14 hours TLC analysis indicated nearly complete reaction of the intermediate 3-O-Benzoyl-1-O-(2-oxo-1,3,2-dioxaphospholan)-ceramide-C16. After cooling down to −5° C. the suspension was filtered. Crude 3-O-Benzoyl-N-palmitoyl-D-erythro-sphingomyelin was dried at 35° C., yielding 9.1 g (76%). The crude material was further purified by column chromatography on 90 g silica gel. It was eluted with 1.1 L methylene chloride/methanol 6/1; 1.1 L methylene chloride/methanol 4/1; and finally 4.3 L methylene chloride/methanol 3/1. The product containing fractions were combined and evaporated to dryness at 35° C. resulting in 8.0 g (yield 88%). Purity by HPLC was 94.8%.

Step 4: N-Palmitoyl-D-erythro-sphingomyelin

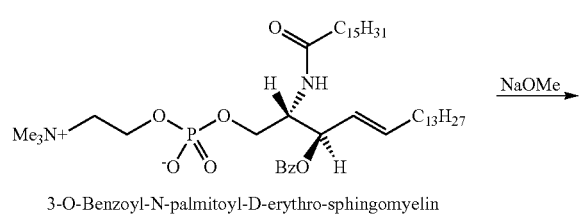

3-O-Benzoyl-N-palmitoyl-D-erythro-sphingomyelin

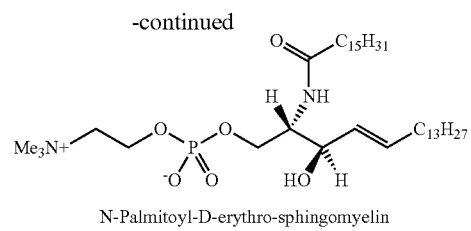

N-Palmitoyl-D-erythro-sphingomyelin

3-O-Benzoyl-N-palmitoyl-D-erythro-sphingomyelin (8.0 g, 9.9 mmol) was dissolved in methanol (40 ml). Sodium methoxide (30% in methanol, 5.4 M, 367 µl, 2.0 mmol) was added to the solution to result in pH 11. After stirring overnight, TLC analysis indicated nearly complete reaction of the benzoylester. Methylene chloride (80 ml) was added followed by 38 ml water and the pH was adjusted to 6-7 with 1.8 ml 1M hydrochloric acid. The lower layer was evaporated to dryness at 35° C. and the residue was taken up in 8.5 ml methanol and 8.5 ml methylene chloride. Acetone (95 mL) was added to the clear solution. The suspension was stirred at 0° C. a few hours and filtered. The resulting residue was dried at 30° C., yielding 4.3 g of the title product, N-Palmitoyl-D-erythro-sphingomyelin, (62%). Purity by HPLC was 98.9%. Based on NMR analysis the content of the cis isomer and the L-threo isomer was lower than 1% respectively.

$^1$H NMR ($\triangleq$ ppm, CDCl$_3$/CD$_4$OD): 0.88 (6H, t, 2×CH$_3$), 1.25 (46H, m, 23×CH$_2$), 1.56 (2H, m, (C=O)CH$_2$CH$_2$), 1.99 (2H, m, CH=CHCH$_2$), 2.14 (2H, t, (C=O)CH$_2$), 3.24 (9H, br s, N(CH$_3$)$_3$), 3.68 (2H, m, POCH$_2$CH$_2$N), 3.91 (2H, m, POCH$_2$CH), 4.04 (1H, t, CHO, J=7.7 Hz), 4.14 (1H, m, CHN), 4.28 (2H, m, POCH$_2$CH$_2$N), 5.42-5.46 (2H, dd, CHCH=CHCH$_2$, J 15.3, 7.4 Hz), 5.65-5.70 (1H, dt, CHCH=CHCH$_2$, J 14.6, 7.2 Hz)

Example 3

Pilot-Scale Synthesis of Palmitoyl Sphingomyelin via (S)-3-(tert-Butoxycarbonyl)-4-(1-oxo-hexadec-2-enyl)-2,2-dimethyloxazolidine

Step 1: Boc-L-Ser-OMe 32.2 kg L-Ser-OMe.HCl (206.97 mol) was suspended in 288 kg ethyl acetate in a 630 L vessel and cooled to 2° C. Triethylamine (24.1 kg, 238.17 mol, 1.15 eq.) was added followed by a solution of Boc$_2$O (51.9 kg, 237.80 mol, 1.15 eq.) in 24 kg ethyl acetate. The reaction mixture was warmed to 22° C. and stirred overnight. TLC analysis showed a content of L-Ser-OMe.HCl of less than 1%. 114 L purified water was added and the phases were separated. Washing was repeated twice with 114 L purified water. The three aqueous phases were combined and extracted with 102 kg ethyl acetate. TLC analysis indicated absence of product in the aqueous phase. The two organic phases were combined and evaporated to dryness at 60° C. 88 kg toluene was added to the residue and distilled off at 60° C. This procedure was repeated. Purity of crude Boc-L-Ser-OMe was 95-97% by TLC analysis.

Step 2: (Tert-butoxycarbonyl)-2,2-Dimethyl-4-Oxazolidincarboxylic Acid Ester

Crude Boc-L-Ser-OMe (about 45.4 kg, 206.97 mol) was dissolved in 256 kg tetrahydrofuran at 22° C. in a 630 L vessel. 71.8 kg 2,2-dimethoxypropane (689.39 mol, 3.33 eq.) were added followed by a solution of 3.3 kg benzenesulfonic acid (20.86 mol, 0.10 eq.) in 20 kg tetrahydrofuran and washing with 20 kg tetrahydrofuran. The reaction mixture was heated to reflux, 210 L tetrahydrofuran were distilled off in three hours. TLC analysis showed a content of Boc-L-Ser-OMe of 1-2%. Neutralization to pH 6.5 was performed with 1.0 kg triethylamine (9.88 mol, 0.05 eq) at 22° C. The reaction mixture was evaporated to dryness at 60° C., followed by addition of 82 kg hexane and 26 L purified water at 25° C. The organic phase was washed with 45 L purified water. TLC analysis indicated absence of product in the aqueous phases. The organic phase was evaporated to dryness at 60° C. Toluene (88 kg) was added to the residue and distilled off at 60° C. twice. The product, (tert-butoxycarbonyl)-2,2-dimethyl-4-oxazolidincarboxylic acid ester, (48.89 kg, 188.55 mol, 91% yield from L-Ser-OMe.HCl) was isolated as a yellow liquid. Purity was found to be 97% by TLC analysis. Loss on drying was 4.2% and the water content 0.1%. Identity was confirmed by MS and $^1$H NMR.

Step 3: (S)-3-(tert-butoxycarbonyl)-4-(2-(dimethoxyphosphoryl)-1-oxo-ethyl)-2,2-dimethyloxazolidin A 100 L vessel was conditioned with 15 kg tetrahydrofuran and dried under vacuum at 50° C. Dimethyl methylphosphonate (4.6 kg, 37.07 mol, 2.00 eq) was introduced into the vessel and dissolved in 29 kg tetrahydrofuran. The mixture was cooled down to −75° C. and 9.4 kg of a solution of 25% n-butyllithium in heptane (2.34 kg n-butyllithium, 36.58 mol, 1.98 eq) was added over two hours while the mixture was kept at −70 to −75° C., followed by washing with 5 L heptane. After stirring for one hour a solution, of 4.8 kg crude (tert-butoxycarbonyl)-2,2-dimethyl-4-oxazolidincarboxylic acid ester (18.51 mol) in 4 kg tetrahydrofuran was added over one hour while the mixture was kept at −70 to −75° C., followed by washing with 5 L tetrahydrofuran. The reaction mixture was warmed to 0° C. over 40 minutes and stirred for 30 minutes.

TLC analysis showed a content of (tert-butoxycarbonyl)-2,2-dimethyl-4-oxazolidincarboxylic acid ester of 10-15%. Quenching was performed with a solution of 600 mL purified water in 4.8 kg tetrahydrofuran below 20° C. The pH was adjusted to 6-7 with 13 L of a solution of 20% citric acid monohydrate in purified water below 20° C. After addition of 10 L ethyl acetate, the phases were separated. The aqueous phase was extracted with 13 kg ethyl acetate. TLC analysis indicated absence of product in the aqueous phase. The two organic phases were combined and evaporated to a volume of 20 L at 60° C. Final drying in a rotary evaporator at 40° C. yielded 7.2 kg (20.49 mol, 111%) of the title compound as a yellow oil. Purity was approximately 70% by TLC analysis. Loss on drying was 14.4% and the water content 1.4%. Identity was confirmed by MS.

Step 4: (S)-3-(tert-butoxycarbonyl)-4-(1-oxo-hexadec-2-enyl-2,2-dimethyloxazolidin (S)-3-(tert-butoxycarbonyl)-4-(2-(dimethoxyphosphoryl)-1-oxo-ethyl)-2,2-dimethyloxazolidin (21.6 kg, 61.48 mol) and 17.0 kg potassium carbonate (123.0 mol, 2.00 eq.) in added to 239 kg acetonitrile at 22° C. in a 250 L vessel while stirring. 1-tetradecanal (6.53 kg, 30.75 mol, 0.50 eq) and 3.1 L purified water were added to give a pH of 9.0. After the reaction was allowed to proceed over night, TLC analysis showed a content of 1-tetradecanal of 5-10% and phosphonate of 2%. The salts were filtered off and washed with 270 L hexane in portions. The combined organic phases were evaporated to dryness at 60° C. The residue was dissolved in 48 kg hexane and washed twice with a solution of 0.9 kg sodium chloride in 18 L purified water. TLC analysis indicated absence of product in the aqueous phases. The organic phase was evaporated to dryness at 60° C. and dissolved in 75 kg hexane. Final drying in a rotary evaporator at 40° C. yielded 16.9 kg (38.61 mol, 63% based on Phosphonate) of the title compound as a brown oil. Purity was approximately 50-86% by TLC depending on detection method and 81% by HPLC analysis. Loss on drying was 2.2% and the water content 0.05%. Identity was confirmed by MS.

Step 5: (2S,3R,4E)-3-(tert-butoxycarbonyl)-4-(1-hydroxy-hexadec-2-enyl)-2,2-dimethyloxazolidin Crude (S)-3-(tert-butoxycarbonyl)-4-(1-oxo-hexadec-2-enyl)-2,2-dimethyloxazolidin (16.9 kg, 38.61 mol) and 15.8 kg cerium chloride heptahydrate (42.49 mol, 1.10 eq.) were stirred in 305 kg methanol in a 1000 L vessel and cooled to −18° C. A solution of 2.19 kg sodium borohydride (57.89 mol, 1.50 eq.) and 58 g 30% caustic soda (0.44 mol) in 8.8 L purified water (resulting in a 0.2% caustic soda) was cooled to 0° C. and then added to the ketone over five hours. After additional 30 minutes of stirring, TLC analysis showed a content of ketone of less than 1%. Excess sodium borohydride was deactivated by warming the reaction mixture to 22° C. over two hours, followed by stirring for one hour. Methanol (320 L) was distilled off at 60° C. The precipitated salts were filtered and washed with 44 kg toluene in two portions. The filtrate separated into two phases and the aqueous phase was extracted twice with 33 kg toluene. TLC analysis indicated absence of product in the aqueous phase and the filter residue. The combined organic phases were diluted with 77 L ethyl acetate and washed with a mixture of 39 L purified water, 3.9 kg EDTA, and 1.9 L 30% caustic soda followed by 1.9 kg sodium chloride in 39 L purified water. TLC analysis indicated absence of product in the aqueous phases. The organic phase was evaporated to dryness at 60° C. and dissolved in 18 kg toluene. Final drying in a rotary evaporator at 60° C. yielded 15.95 kg (36.28 mol, 94%) of the title compound as a yellow oil. Purity was approximately 70-90% by TLC depending on detection method and 90% by HPLC analysis. Loss on drying was 5.2% and the water content 0.05%. Identity was confirmed by MS.

Step 6: D-erythro-Sphingosine

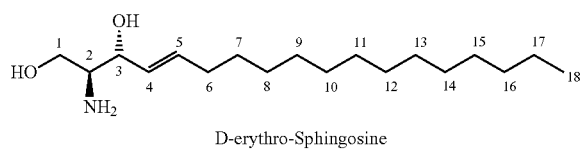

D-erythro-Sphingosine

In a 60 L vessel 24 kg methanol was cooled to 0° C. Over the course of 30 minutes 5.69 kg acetylchloride (72.48 mol, 2.00 eq.) was introduced. This was followed by warming to 22° C. to produce a methanolic hydrochloride solution. Crude (2S,3R,4E)-3-(tert-butoxycarbonyl)-4-(1-hydroxy-hexadec-2-enyl)-2,2-dimethyloxazolidin (15.95 kg, 36.28 mol) was dissolved in 31 kg methanol in a 160 L vessel at 22° C. The methanolic hydrochloride solution was added over 30 minutes. After seven hours, TLC analysis showed a less than 1% of the starting material. The reaction was neutralized with a solution of 7.34 kg triethylamine (72.54 mol, 2.00 eq.) in 10 kg methanol. The reaction mixture was evaporated to dryness at 60° C. and dissolved in 105 kg methylene chloride, 31 kg 2-propanol, and 40 L purified water. After phase separation the organic phase was washed with 40 L purified water and subsequently with 40 L demineralized water and 7 kg 2-propanol. TLC analysis indicated absence of product in the two first aqueous phases but product in the third aqueous phase. The product was extracted with 40 L methylene chloride. The combined organic phases were evaporated to dryness at 60° C. The residue was suspended in 33 kg ethyl acetate and again evaporated to dryness. Crystallization was performed from a mixture of 36 L ethyl acetate and 7.2 L hexane at −20° C. The solid was filtered and washed in portions with a mixture of 7.2 L ethyl acetate and 1.4 L hexane followed by 7.2 L pure ethyl acetate. After drying at 30° C. the resulting 6.45 kg were recrystallized from a mixture of 24 L ethyl acetate and 8 L hexane at −20° C. The solid was filtered and washed in portions with a mixture of 4.8 L ethyl acetate and 1.6 L hexane followed by 6.4 L pure ethyl acetate. After drying at 30° C. the resulting 5.90 kg were again recrystallized from a mixture of 16 L ethyl acetate and 16 L hexane at −20° C. The solid was filtered and washed in portions with a mixture of 3.2 L ethyl acetate and 3.2 L hexane followed by 6.4 L pure ethyl acetate. Final drying at 30° C. yielded 5.60 kg (18.71 mol, 52%) of the title compound as a brown solid. Purity was 89.2% by HPTLC and 95.6% by HPLC analysis with 0.61% L-threo-sphingosine. Loss on drying was 0.4% and the water content 0.6%. Identity was confirmed by MS and 1H NMR.

$^1$H NMR (600 MHz, δ ppm, CDCl$_3$), position: 0.88 (3H, t) 18, 1.2-1.3 (20H, m) 8, 9, 10, 11, 12, 13, 14, 15, 16, 17; 1.37 (2H, m) 7; 2.04 (2H, m, CH$_2$CH) 6; 3.17 (1H, m, CHNH$_2$) 2; 3.77 (2H, m, CH$_2$OH) 1; 4.34 (1H, m, CH(OH)CH) 3; 5.46 (1H, ddt, J 15.4, 6.4, 1.0 Hz, CH(OH)CH)) 4; 5.79 (1H, dtd, J 15.4, 6.7, 1.1 Hz, CH$_2$CH) 5.

Step 7: D-Erythro-Ceramide-C16

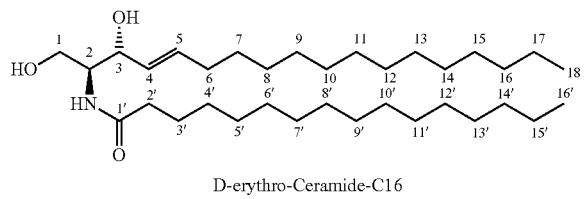

D-erythro-Ceramide-C16

5.50 kg D-Erythro-Sphingosine (18.36 mol), 4.71 kg palmitic acid (18.37 mol, 1.00 eq.) and 7.66 kg O-Benzo-triazole-N,N,N',N'-tetramethyl-uronium-hexafluoro-phosphate (20.20 mol, 1.10 eq.) were suspended in 36 kg dimethylformamide and 118 kg tetrahydrofuran in a 250 L vessel and cooled to 2° C. Triethylamine (5.06 kg, 50.00 mol, 2.72 eq.) in 5 L tetrahydrofuran was added resulting in pH 9.0. After 90 minutes TLC analysis showed a content of D-erythro-sphingosine of less than 1% and a content of palmitic acid of less than 1.5%. The reaction mixture was warmed to 22° C. The product was precipitated by addition of a solution of 4.7 kg citric acid in 89 kg purified water. After one hour at 22° C. the reaction mixture was filtered. The crude product was suspended in 154 L purified water for one hour at 22° C. Filtration was followed by washing with three times 28 L purified water and three times 28 L acetone. Suspension was repeated in 122 kg acetone, washing with three times 28 L acetone. Final drying at 35° C. yielded 6.08 kg (11.31 mol, 62%) of the title compound as a slightly yellow solid. Purity was 96.2% by HPTLC and 99.2% by HPLC analysis. Loss on drying was 0.2% and the water content 0.3%. Identity was confirmed by MS and $^1$H NMR.

$^1$H NMR (600 MHz, $\triangleq$ ppm, CDCl$_3$): 0.88 (6H, t) 18, 16'; 1.2-1.4 (44H, m) 8, 9, 10, 11, 12, 13, 14, 15, 16, 17, 4', 5', 6', 7', 8', 9', 10', 11', 12', 13', 14', 15'; 1.37 (2H, m) 7; 1.64 (2H, m) 3'; 2.04 (2H, m, CH$_2$CH) 6; 2.23 (2H, t, CH$_2$CO) 2'; 3.71 (1H, dd, CHNH$_2$) 2; 3.93 (2H, m, CH$_2$OH) 1; 4.31 (1H, m, CH(OH)CH) 3; 5.53 (1H, ddt, J 15.4, 6.4, 1.0 Hz, CH(OH)CH)) 4; 5.79 (1H, dtd, J 15.4, 6.7, 1.1 Hz, CH$_2$CH) 5; 6.25 (1H, d) NH.

Step 8: D-erythro-3-O-Benzoyl-ceramide-C16

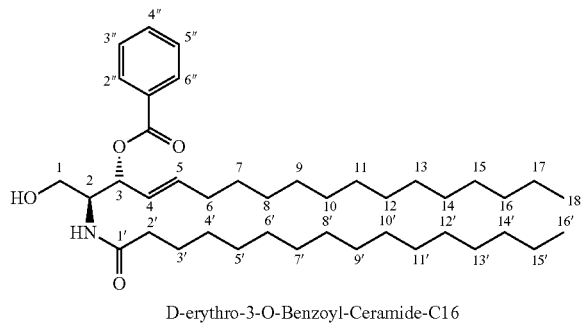

D-erythro-3-O-Benzoyl-Ceramide-C16

For the first protection, 6.08 kg D-erythro-ceramide-C16 (11.31 mol) was suspended in 11.91 kg pyridine and 2.5 kg methylene chloride in a 60 L vessel. A solution of trityl chloride (3.31 kg, 11.87 mol, 1.05 eq.) in 9.5 kg methylene chloride was added followed by 2.5 kg methylene chloride. The reaction mixture was stirred at 25° C. for 56 hours. TLC analysis showed a content of D-erythro-Ceramide-C16 of 3-5%.

For the second step the reaction mixture was cooled to 2° C. N,N-Dimethylaminopyridine (0.139 kg, 1.14 mol, 0.10 eq.) and 2.38 kg benzoyl chloride (16.93 mol, 1.50 eq.) was added to the mixture, followed by 5 kg methylene chloride. After 90 minutes at 2° C. TLC analysis showed a content of intermediate 1-O-Trityl-ceramide-C16 of less than 1%. Work up was performed with 55 kg ethyl acetate and a solution of 1.7 kg citric acid and 3.0 kg sodium chloride in 33 L purified water. The organic phase was washed again with a solution of 1.7 kg citric acid and 3.0 kg sodium chloride in 33 L purified water and twice with a solution of 3.5 kg sodium chloride in 30 L purified water. TLC analysis indicated absence of product in the aqueous phases. The organic phase was evaporated to dryness at 50° C. The residue which contained the product, D-erythro 1-O-Trityl-3-β-benzoyl-ceramide-C16, was dissolved in 27 kg toluene and subsequently evaporated to dryness at 50° C. This procedure was repeated twice.

For the third step the residue from the previous reaction was dissolved in 67 kg methanol and 161 kg methylene chloride and cooled to 2° C. pH was adjusted to 2.5 with a solution of para-toluene sulfonic acid mono hydrate (6.41 mol 0.57 eq.) in 23 kg methanol. After warming to 22° C. and stirring for 14 hours TLC analysis showed a content of intermediate D-erythro 1-O-Trityl-3-O-benzoyl-ceramide-C16 of less than 1%. The addition of 969 g Triethylamine (9.58 mol, 0.85 eq.) raised the pH to 7.0. The reaction mixture was evaporated to dryness at 50° C. Crude 3-O-Benzoyl-ceramide-C16 was suspended in 69 kg hexane at 40° C. and cooled down to 0° C. After 40 minutes the solid was isolated by filtration and washed with 20 kg hexane. Drying at 35° C. yielded 5.40 kg which was dissolved in 38 kg methylene chloride. This solution was purified by chromatography on 76 kg silica gel which was conditioned with a mixture of 175 kg hexane and 49 kg ethyl acetate. Elution with 12 kg methylene chloride, a mixture of 502 kg hexane and 137 kg ethyl acetate and a mixture of 482 kg hexane and 647 kg ethyl acetate was performed. The collected fractions contained no product. The product was eluted with a mixture of 451 kg hexane and 205 kg ethyl acetate and a mixture of 802 kg hexane and 547 kg ethyl acetate. Solvents were distilled off at 50° C. The resulting residue was suspended in 24 L hexane at 40° C. and cooled down to 0° C. After 45 minutes the solid was isolated by filtration and washed with 4.8 L hexane in portions. Drying at 35° C. yielded 3.15 kg (4.91 mol, 43%) of the title compound as a white solid. Purity was 100.0% by HPTLC and 96.3% by HPLC analysis. Loss on drying was 0.05% and the water content 0.2%. Identity was confirmed by MS and $^1$H NMR.

$^1$H NMR (600 MHz, $\delta$ ppm, CDCl$_3$): 0.88 (6H, t) 18, 16'; 1.2-1.4 (44H, m) 8, 9, 10, 11, 12, 13, 14, 15, 16, 17, 4', 5', 6', 7', 8', 9', 10', 11', 12', 13', 14', 15'; 1.35 (2H, m) 7; 1.61 (2H, m) 3'; 2.05 (2H, m, CH$_2$CH) 6; 2.19 (2H, m, CH$_2$CO) 2'; 3.71 (2H, m, CH$_2$OH) 1; 4.27 (1H, m, CHNH) 2; 5.54 (1H, t, CH(OCOPh)CH)) 3; 5.62 (1H, ddt, J 15.4, 6.4, 1.0 Hz, CH(OCOPh)CH)) 4; 5.85 (1H, dtd, J 15.4, 6.7, 1.1 Hz, CH$_2$CH) 5; 6.05 (1H, d) NH; 7.46 (2H, dd, J 7.6, 7.2 Hz) 3", 5"; 7.59 (1H, dd, J 7.6, 7.6 Hz) 4"; 8.04 (2H, d, J 7.2 Hz) 2", 6".

Step 9:
D-erythro-3-O-Benzoyl-N-palmitoyl-sphingomyeline

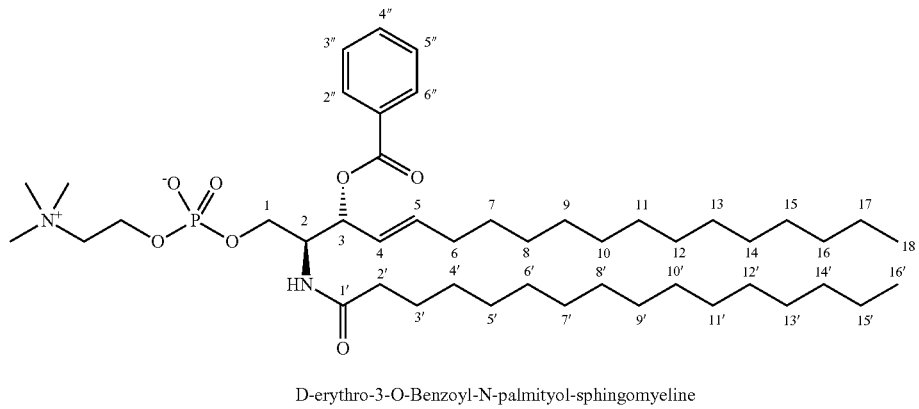

D-erythro-3-O-Benzoyl-N-palmityol-sphingomyeline 1.60 kg D-erythro-3-O-Benzoyl-ceramide-C16 (2.50 mol) and 0.20 kg tetramethylethylenendiamine (TMEDA) (1.73 mol, 0.69 eq.) were dissolved in 38 L toluene in a 100 L vessel at 35° C. After cooling to 6° C. a solution of 2-chloro-2-oxo-1,3,2-dioxaphospholane (CCP) (0.47 kg, 3.30 mol, 1.32 eq.) in 1 L acetonitrile was added during 15 minutes followed by 3 L acetonitrile. The reaction mixture was warmed to 22° C. Stirring was continued for two hours. TLC analysis showed a content of 3-O-Benzoyl-ceramide-C16 of less than 0.5%. After addition of 32 L acetonitrile temperature was decreased to −10° C. Liquid trimethylamine (7.42 kg, 125.53 mol, 50.21 eq.) was introduced and the next reaction step was started by heating to 65° C. for 15 hours. TLC analysis showed a content intermediate ring of less than 0.5%. Product was crystallized by cooling to −30° C. and isolated by filtration with subsequent washing with 13 L acetonitrile. By drying at 35° C. yielded 1.85 kg of an off-white solid. The reaction was repeated with 1.58 kg D-erythro-3-β-Benzoyl-ceramide-C16 (2.45 mol) yielding another 1.82 kg crude D-erythro-3-O-Benzoyl-P-SM18. Both crude materials were combined and dissolved in 29 L methylene chloride and 14.5 L methanol. This solution was purified by chromatography on 72 kg silica gel which was conditioned with a mixture of 337 kg methylene chloride and 33 kg methanol. Elution with a mixture of 966 kg methylene chloride and 95 kg methanol, a mixture of 1866 kg methylene chloride and 223 kg methanol, a mixture of 328 kg methylene chloride and 82 kg methanol, a mixture of 1345 kg methylene chloride and 268 kg methanol, a mixture of 530 kg methylene chloride and 158 kg methanol and a mixture of 371 kg methylene chloride and 221 kg methanol was performed. The volume of the collected fractions was 140 L. Solvents of fractions 17-38 were distilled of at 50° C. Final drying in a rotary evaporator at 40° C. yielded 3.36 kg (2.92 kg on dry basis, 3.61 mol, 73%) of the title compound as a slightly yellow solid. Purity was 99.5% by HPTLC and 98.7% by HPLC analysis. Loss on drying was 11.5% and the water content 1.7%. Identity was confirmed by MS and 1H NMR.

$^1$H NMR (600 MHz, δ ppm, CDCl$_3$): 0.88 (6H, t) 18, 16'; 1.2-1.3 (46H, m) 7, 8, 9, 10, 11, 12, 13, 14, 15, 16, 17, 4', 5', 6', 7', 8', 9', 10', 11', 12', 13', 14', 15'; 1.56 (2H, m) 3'; 1.99

(2H, m, CH$_2$CH) 6; 2.16 (2H, m, CH$_2$CO) 2'; 3.21 (9H, s, N(CH$_3$)$_3$)N(CH$_3$)$_3$; 3.65 (2H, m, POCH$_2$CH$_2$N(CH$_3$)$_3$) CH$_2$N; 3.97 (2H, m, CH$_2$OP) 1; 4.21 (2H, br s, POCH$_2$CH$_2$N(CH$_3$)$_3$)POCH$_2$; 4.45 (1H, m, CHNH) 2; 5.50 (1H, m, CH(OCOPh)CH)) 3; 5.54 (1H, m, CH(OCOPh)CH)) 4; 5.82 (1H, dt, CH$_2$CH) 5; 7.39 (1H, d) NH; 7.43 (2H, t, J 7.2 Hz) 3", 5"; 7.55 (1H, t, J 7.2 Hz) 4"; 7.99 (2H, d, J 7.2 Hz) 2", 6".

Step 10: N-Palmitoyl-D-erythro-sphingomyelin

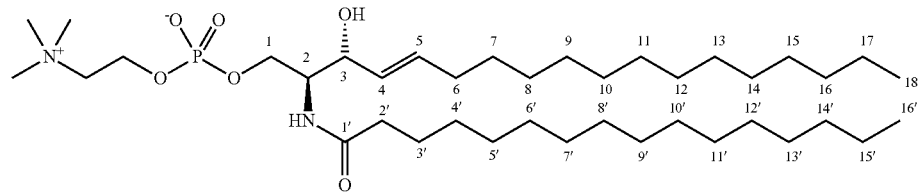

N-Palmityol-D-erythro-sphingomyeline 3.36 kg D-erythro-3-O-Benzoyl-N-palmitoyl-sphingomyeline (2.92 kg on dry basis, 3.61 mol) was dissolved in 10 L methanol in a rotary evaporator at 22° C. and transferred into a 70 L vessel with 5 L methanol. 138 mL of a solution of sodium methoxide in methanol (30%, 0.75 mol, 0.21 eq.) was used to adjust the pH to 11.5. Stirring was continued for 23 hours at 22° C. TLC analysis showed a content of D-erythro-3-O-Benzoyl-N-palmitoyl-sphingomyeline of less than 0.5%. Phase separation occurred after introduction of 31 L methylene chloride and 13 L purified water. The organic phase was neutralized to pH 7.0 with 8 L methanol, 8 L purified water and 55 mL 1M hydrochloric acid. TLC analysis indicated absence of product in the aqueous phases. The organic phase was evaporated to dryness at 35° C. The residue was co-evaporated twice with 6 L 2-propanol and twice with 12 L methylene chloride. Crude product was dissolved in 2.6 L methanol and 2.6 L methylene chloride and filtered through a 0.2 µm filter with washing with 1.2 L methanol and 1.2 L methylene chloride. Crystallization was induced by addition of 42 L acetone and cooling to 0° C. After 15 hours the precipitate was isolated and washed with 24 L acetone in four portions. The wet product was suspended in 19 L acetone at 22° C. for 2.5 hours. After isolation and washing with 12 L acetone in four portions process was finalized by drying at 30° C. for 46 hours. 2.29 kg (3.25 mol, 90%) of the title compound as a white powder was obtained. Purity was 99.2% by HPTLC and 99.0% by HPLC analysis. Water content was 0.7%. Identity was confirmed by MS and 1H NMR.

$^1$H NMR (600 MHz, δ ppm, CDCl$_3$): 0.88 (6H, t) 18, 16'; 1.2-1.3 (46H, m) 7, 8, 9, 10, 11, 12, 13, 14, 15, 16, 17, 4', 5', 6', 7', 8', 9', 10', 11', 12', 13', 14', 15'; 1.57 (2H, m) 3'; 1.99 (2H, m, CH$_2$CH) 6; 2.15 (2H, m, CH$_2$CO) 2'; 3.23 (9H, s, N(CH$_3$)$_3$)N(CH$_3$)$_3$; 3.65 (2H, m, POCH$_2$CH$_2$N(CH$_3$)$_3$) CH$_2$N, 3.91 (2H, m, CH$_2$OP) 1; 4.05 (1H, t, J=7.7 Hz, CH(OH)CH)) 3; 4.15 (1H, m, CHNH) 2; 4.26 (2H, m, POCH$_2$CH$_2$N(CH$_3$)$_3$)POCH$_2$; 5.45 (1H, dd, J 15.3 Hz, 7.4 Hz, CH(OH)CH)) 4; 5.69 (1H, dt, J 14.6 Hz, 7.2 Hz, CH$_2$CH) 5.

Table 1 shows yields and /intermediate/product characteristics at the 120-g scale (Example 3) for Scheme 3. Table 2 displays the results for the 2-kg scale (Example 4) for Scheme 3.

TABLE 1

| From | To | Yield | HPLC | HPTLC | LoD | KF |
|---|---|---|---|---|---|---|
| Sphingosine | Ceramide-C16 | 91.6% | 98.4% | 99.0% | 0.1% | 0.2% |
| Ceramide-C16 | 3-O-Benzoyl-Ceramide-C16 | 57.9% | 97.1% | — | 0.2% | 0.2% |
| 3-O-Benzoyl-Ceramide-C16 | 3-O-Benzoyl-Sphingomyelin | 14.2% | 99.0% | 98.8% | 3.2% | 2.8% |
| 3-O-Benzoyl-Sphingomyelin | N-Palmitoyl-D-erythro-sphingomyelin | 68.5% | 98.6% | 99.4% | — | 4.4% |

LoD = loss on drying,
KF = water content

TABLE 2

| From | To | Yield | HPLC | HPTLC | LoD | KF |
|---|---|---|---|---|---|---|
| Sphingosine | Ceramide-C16 | 61.6% | 99.2% | 96.2% | 0.2% | 0.3% |
| Ceramide-C16 | 3-O-Benzoyl-Ceramide-C16 | 43.4% | 96.3% | 100.0% | 0.05% | 0.2% |
| 3-O-Benzoyl-Ceramide-C16 | 3-O-Benzoyl-Sphingomyelin | 72.7% | 99.0% | 99.5% | 11.5% | 1.7% |
| 3-O-Benzoyl-Sphingomyelin | N-Palmitoyl-D-erythro-sphingomyelin | 90.1% | 99.0% | 99.2% | <250 ppm | 0.7% |

LoD = loss on drying,
KF = water content

Example 5

Confirmation of Optical Purity, Identity with Natural Product Egg Sphingomyelin and Absolute Configuration The NMR spectra were taken on a Varian Inova spectrometer, operating at 500 MHz for $^1$H and 125 MHz for $^{13}$C, equipped with a 5 mm triple resonance probe and z-axis gradients. The solvent was chloroform-d and the temperature 25° C. The chemical shifts for H and $^{13}$C were reference to the residual solvent signal, 7.27 ppm for $^1$H and 77 ppm for $^{13}$C, on the tetramethylsilane scale.

The proton spectrum was taken in 4 transients, with a 90° pulse, on a spectral window from 18 to −1 ppm. The acquisition time was 5 s and the relaxation delay 5 s. 94842 points in the FID were transformed into 131072 points in the spectrum, with no apodization.

The $^1$H-$^{13}$C gHMBCAD spectrum was acquired with the standard Varian pulse sequence, using an adiabatic pulse on $^{13}$C, and it was optimized for a coupling constant of 8 Hz. In the proton dimension 4096 points were acquired over a spectral window of 3755 Hz, from 1.24 to 8.74 ppm and transformed into the same number of points in the spectrum, weighting with a shifted Gaussian function (gf=0.277, gfs=0.126). In the carbon dimension 2*512 increments were taken in one transient each, over a spectral window from 10 to 190 ppm and transformed into 4096 points, using a shifted Gaussian function (gf=0.019, gfs=0.005). The relaxation delay was 1 s.

Chemical shifts assignment in N-Palmitoyl-D-erythro-Sphyngosylphosphorylcholine.

The chemical shifts assignment was based on the $^1$H-$^1$H couplings seen in the DQCOSY spectra and the $^1$H-$^{13}$C couplings, one-bond and long-range seen in the $^1$H-$^{13}$C gHSQC and gHMBC spectra. The assignments are presented in Scheme XV.

Scheme XIII. Assignment of the $^1$H and $^{13}$C chemical shifts in N-Palmitoyl-D-erythro-sphingomyelin, in chloroform-d at 25° C.

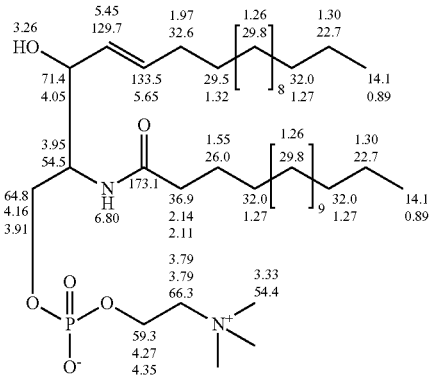

The assignment begun with the proton at 6.80, bound to no carbon, which has to be the amide proton. The gDQCOSY spectrum revealed the sequence 6.80-3.95-4.05-5.45-5.65-1.97, of the sphingosine backbone. Of the three methylene groups seen in the gHSQC spectrum, one has a carbon at 66.3 which couples with the trimethylamino protons at 3.33. Its protons, at 3.79, couple with the protons at 4.27 and 4.53. One of the protons of the remaining methylene group, 4.16, displays indeed a coupling with 3.95. The amide carbon displays a cross-peak with the protons at 2.14 and 2.11.

Comparison of the Egg and Synthetic Sphingomyelin.

In order to maximize the accuracy of the integrals, proton spectra for the three samples were taken in 64 transients, with a 45° pulse, on a spectral window from 14 to −1 ppm. The acquisition time was 5 s and the relaxation delay 15 s. 79872 points in the FID were transformed into 131072 points in the spectrum, with no apodization.

Figure 2:
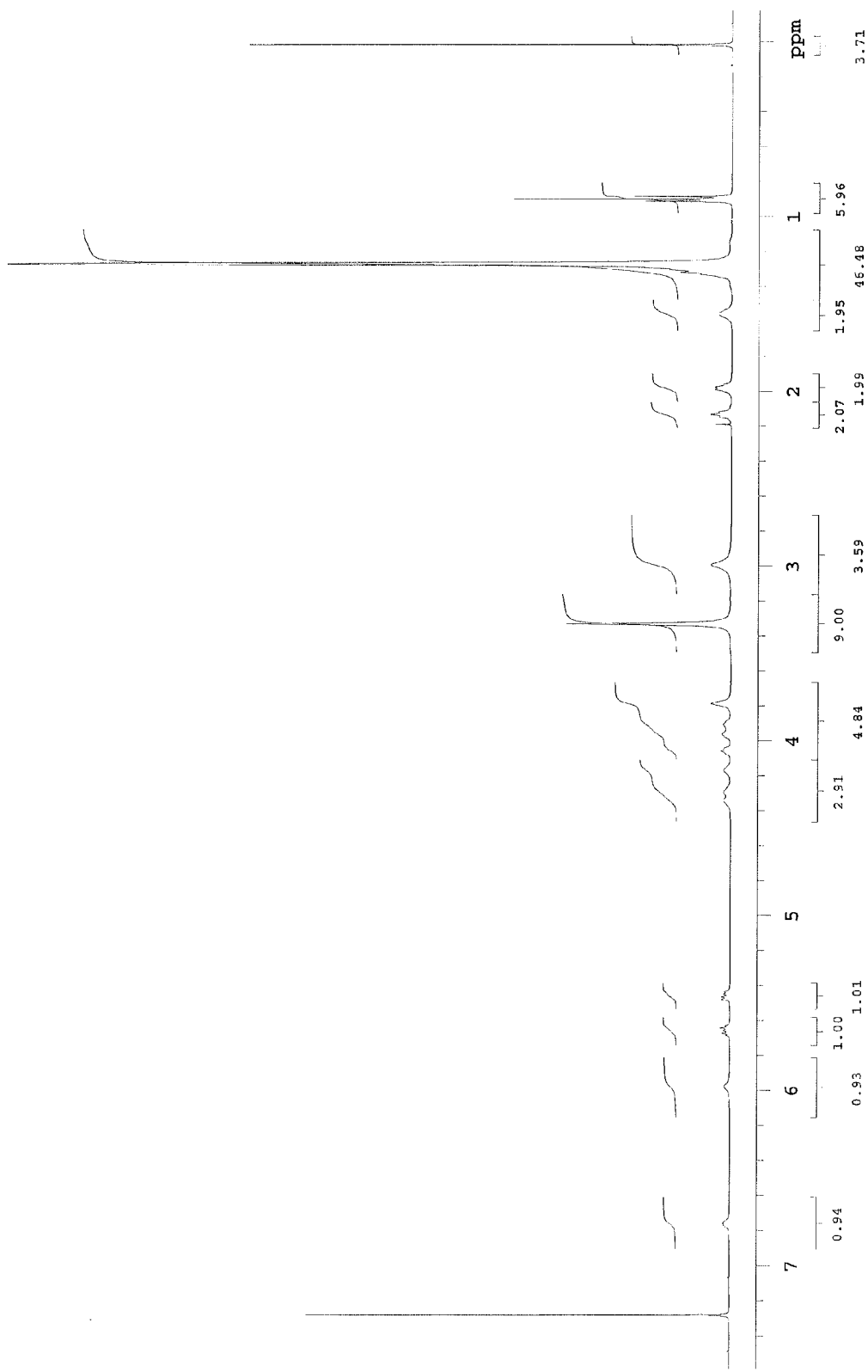
FIG. 2—The $^1$H NMR spectra for N-palmitoyl-D-Erythro-sphingomyelin synthesized by methods of the invention.
Figure 3:
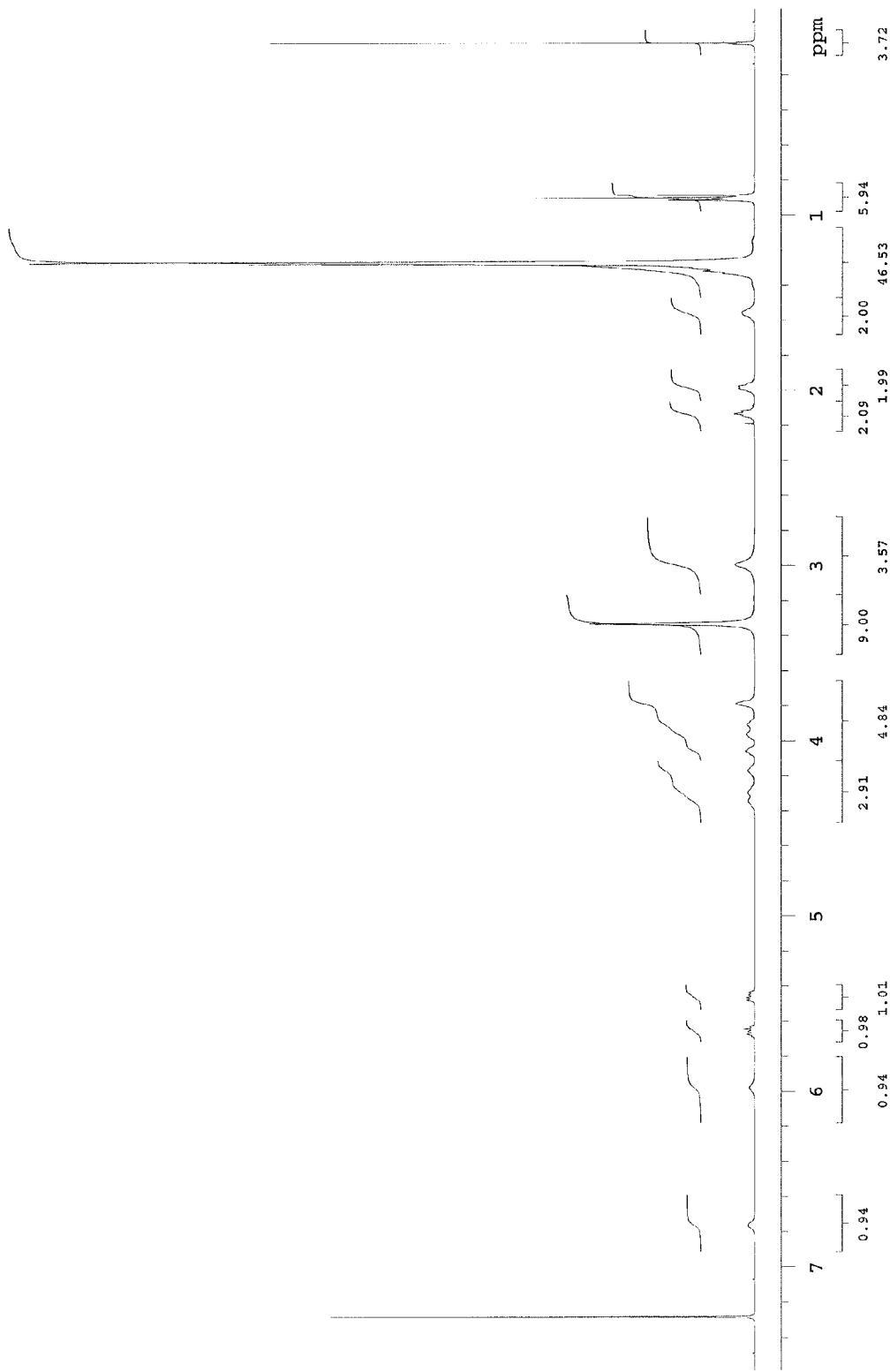
FIG. 3—The $^1$H NMR spectra for N-palmitoyl-D-Erythro-sphingomyelin synthesized by methods of the invention.

The $^1$H spectra for N-Palmitoyl-D-erythro-sphingomyelins from egg and synthesized by methods of the present invention are presented in FIGS. 1-3, correspondingly. The integral was referenced to the signal of the trimethylammonium group at 3.33 ppm (9H). The signal at 2.58 in FIG. 1 and 3.00 in FIGS. 2 and 3 is water. The two synthetic samples are identical, within the precision of the integral, ca. 1%. The natural sample has a shorter average alkyl chain, and some impurities are noticeable for the NH and the alkene signals.

Figure 4:
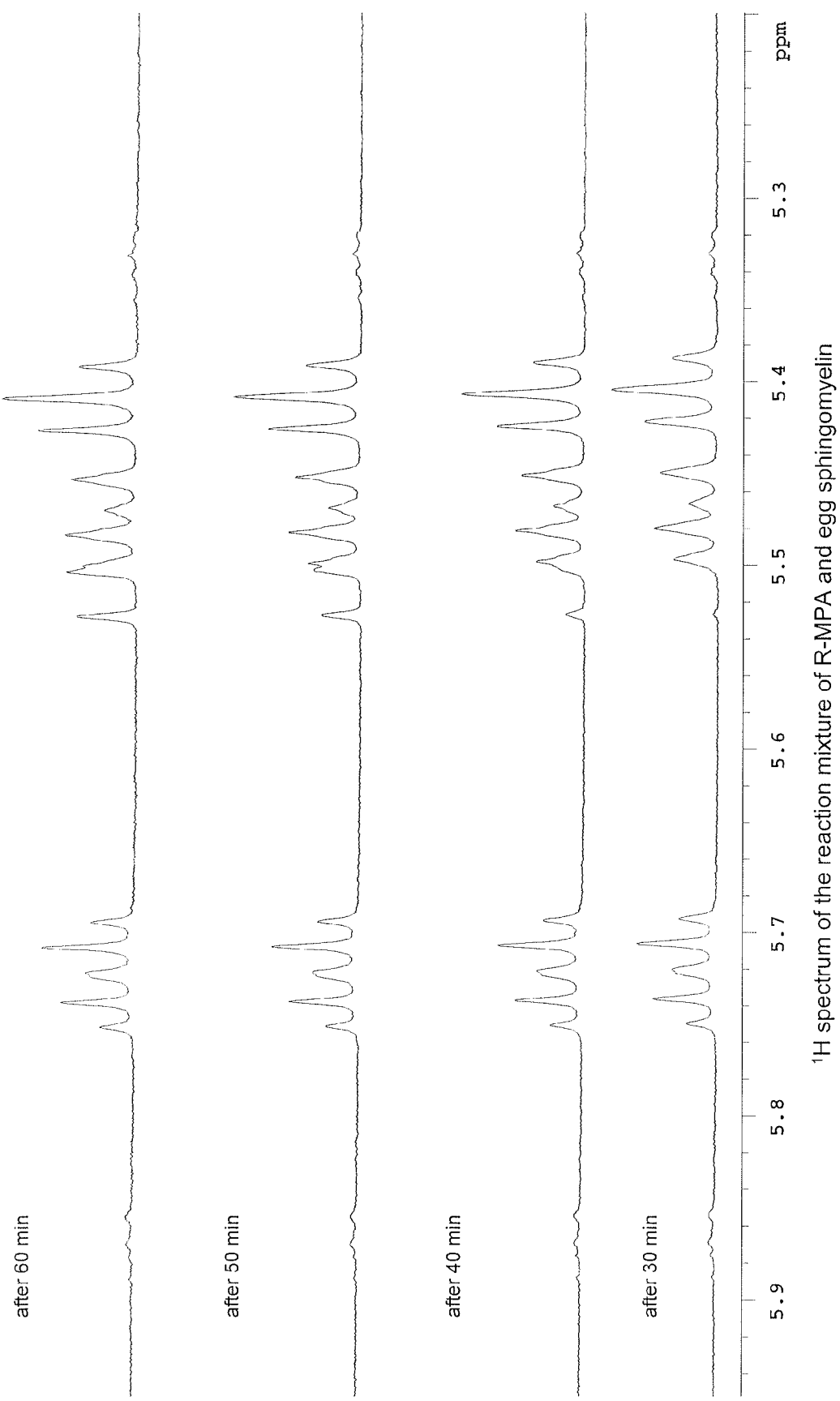
FIG. 4—The $^1$H NMR spectrum of the reaction mixture of R-MPA and naturally occurring egg sphingomyelin.
Figure 5:
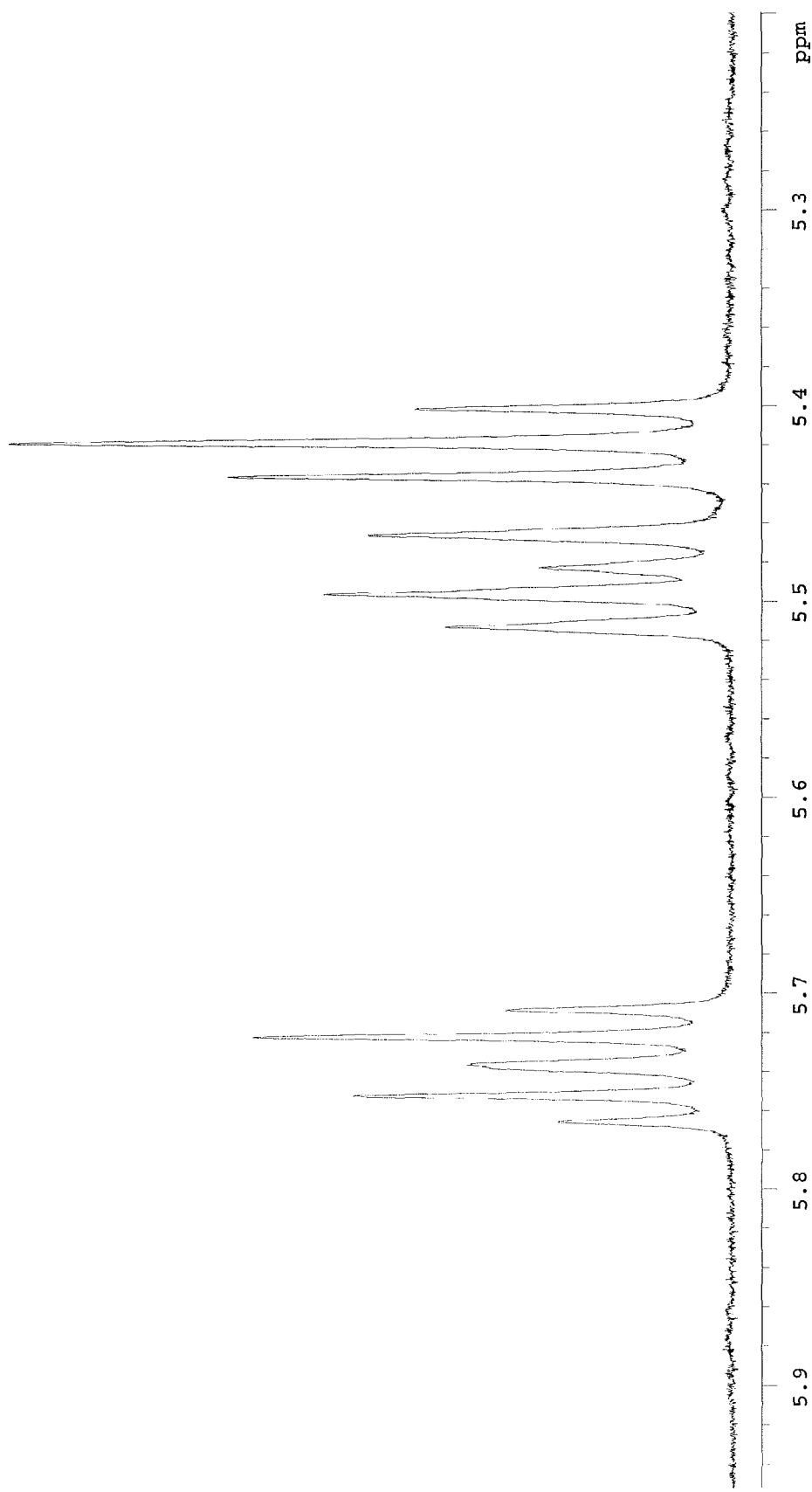
FIG. 5—The $^1$H NMR spectrum of the reaction mixture of R-MPA and synthetic N-Palmitoyl-D-erythro-Sphyngosylphosphorylcholine FIG. 6—The $^1$H NMR spectrum of the reaction mixture of R-MPA and synthetic N-Palmitoyl-D-erythro-Sphyngosylphosphorylcholine FIG. 7—The $^1$H NMR spectrum of the reaction mixture of egg sphingomyelin with an excess of the mixture of 2R+1S-MPA, DCC and DMAP (bottom) and the TOCSY1D spectra with selective excitation of H2 in the R-MPA (top) and S-MPA (bottom) esters.
Figure 6:
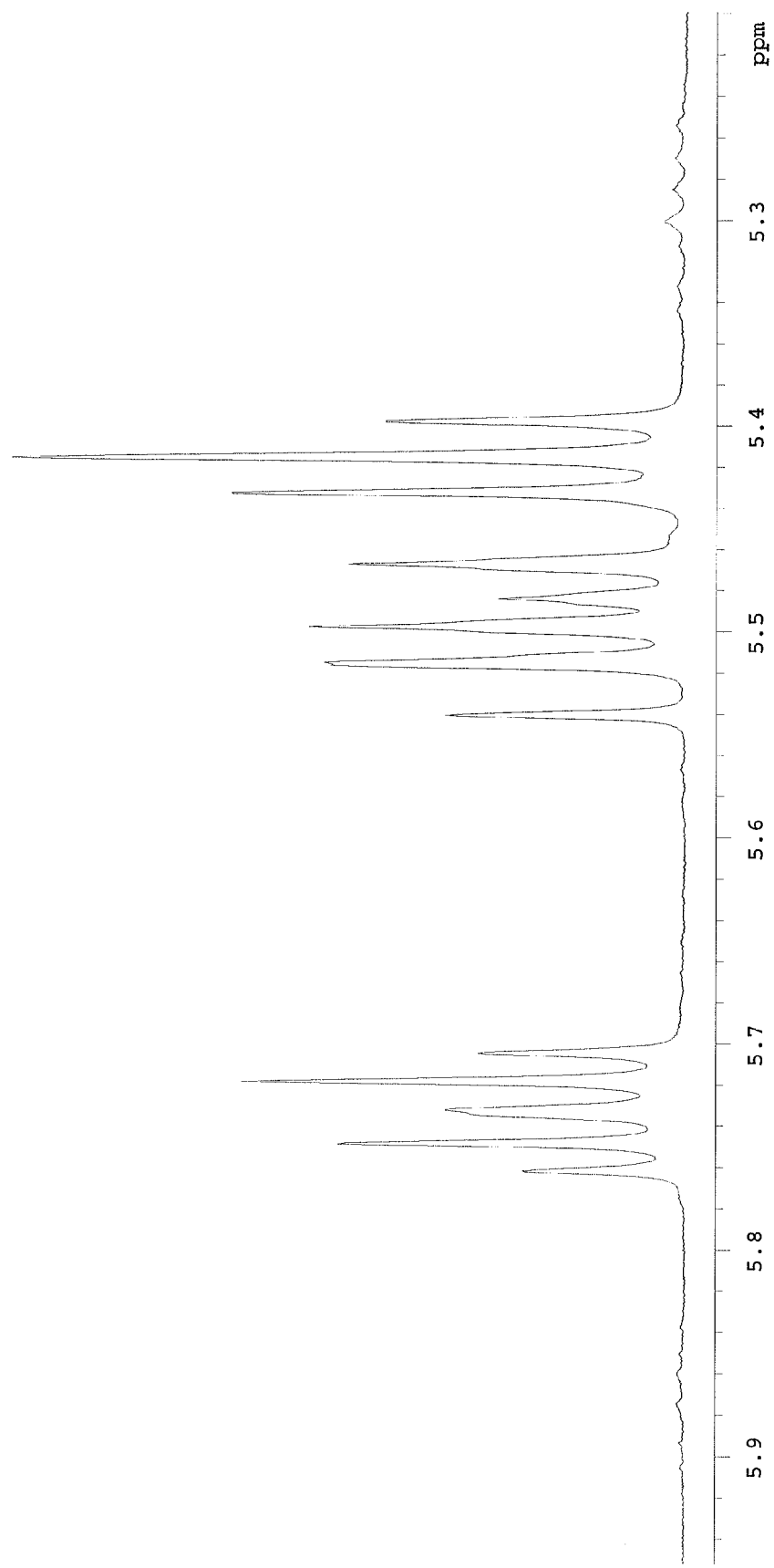

The sphingosine backbone has two chiral carbons, hence the possibility of 4 stereoisomers. The synthetic samples do not show the doubling of the signals expected for a mixture of diastereomers. No such assessment can be made for the egg sphingomyelin, since it is a mixture anyway. To check the enantiomeric purity, the samples were treated in tube with an excess of R-methoxyphenilacetic acid (R-MPA), dicyclohexylcarbodiimide (DCC) and 4-dimethylaminopyridine (DMAP), and the region 5.20-5.95 ppm was examined. The triplet at 5.42 (FIG. 5) is H3 (see caption to Table 3), the doublet of doublets at 5.49 is H4 and the doublet of triplets at 5.73 is H5. FIG. 4 shows the rise of a doublet at 5.53 as the reaction mixture matures, and this doublet is also visible in FIG. 6. Other these signals, there are no signals above 5% of the signals of the ester, therefore the enantiomeric purity (ee) of the sample appears to be at least 90%. The absolute configuration of all three samples is the same, since the signals of H3-H5 in their R-MPA esters have the same chemical shifts.

Determination of the Absolute Configuration.

Figure 7:
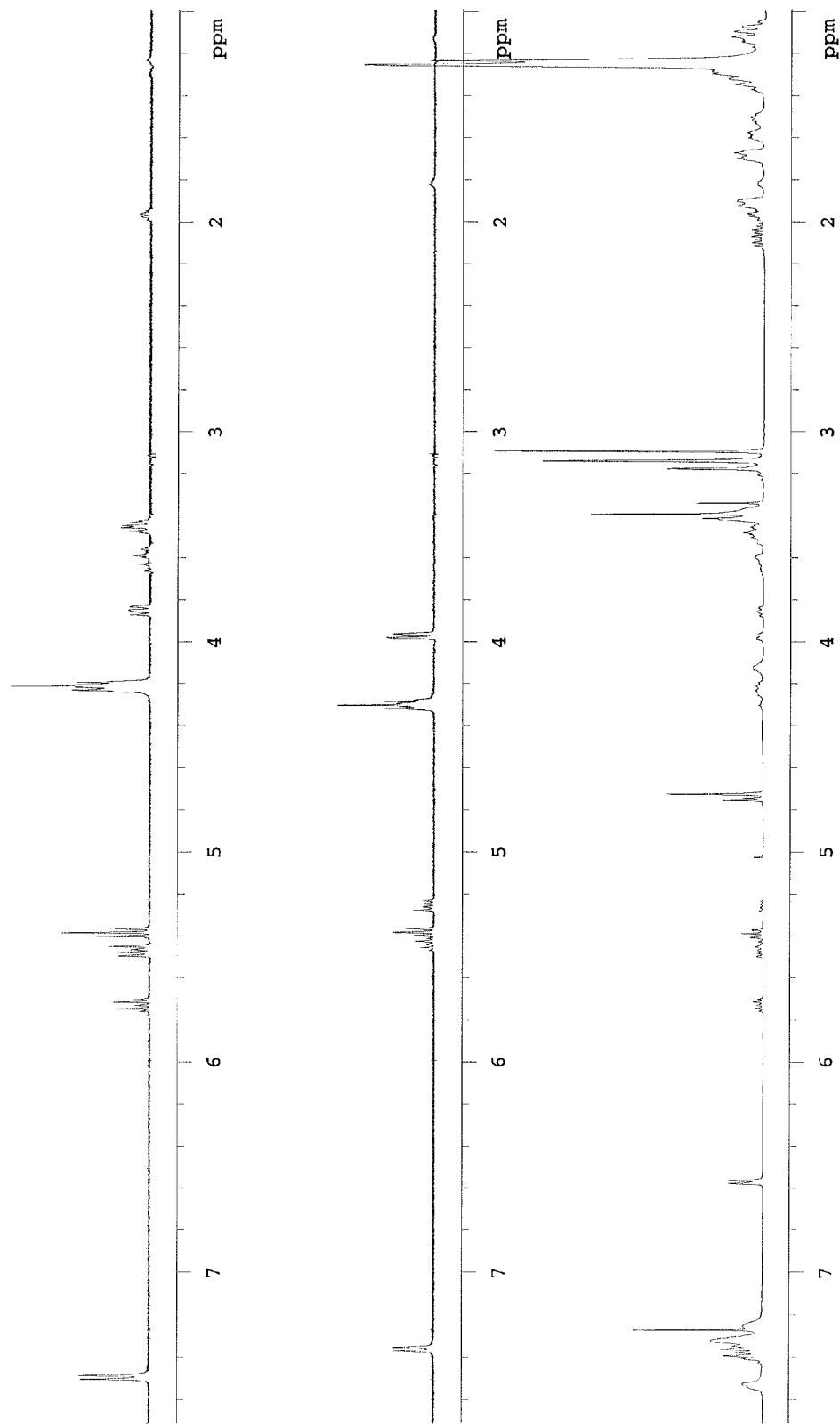

In order to verify the absolute configuration, palmitoyl sphingomyelin was treated in the NMR tube with an excess of a mixture 2R+1S-methoxyphenilacetic acid (2R+1S-MPA), dicyclohexylcarbodiimide (DCC) and 4-dimethylaminopyridine (DMAP). The DdRS measured in the TOCSY1D spectra (FIG. 7) are given in Table 3.

TABLE 3

| DdRS in egg sphingomyelin. | | | | | | | | |
|---|---|---|---|---|---|---|---|---|
| position | 1a | 1b | 2 | 3 | 4 | 5 | 6 | NH |
| alcohol | 4.16 | 3.91 | 3.95 | 4.05 | 5.45 | 5.65 | 1.97 | 6.8 |
| R-MPA | 3.85 | 3.45 | 4.21 | 5.39 | 5.47 | 5.73 | 1.97 | 7.54 |
| S-MPA | 3.97 | 3.97 | 4.3 | 5.39 | 5.26 | 5.44 | 1.82 | 7.4 |
| DdRS | −0.12 | −0.52 | −0.09 | 0 | 0.21 | 0.29 | 0.15 | 0.14 |

Positive DdRS for H4-H6 and negative DdRS for H1a, H1b and H2 indicate that the absolute configuration at C3 is R.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

Each reference disclosed in this application is incorporated by reference herein in its entirety.

The invention claimed is:

1. A method for synthesizing N-palmitoyl-3-O-benzoyl-D-erythro-sphingomyelin, comprising allowing N-palmitoyl-3-O-benzoyl-D-erythro-ceramide to react with 2-chloro-2-oxo-1,3,2-dioxaphospholane in the presence of tetramethylethylenediamine to yield N-palmitoyl-3-O-benzoyl-1-O-(2-oxo-1,3,2-dioxaphospholan)-D-erythro-ceramide, and allowing N-palmitoyl-3-0-benzoyl-1-O-(2-oxo-1,3,2-dioxaphospholan)-D-erythro-ceramide to react with trimethylamine under conditions effective to yield N-palmitoyl-3-O-benzoyl-D-erythro-sphingomyelin;

wherein N-palmitoyl-3-O-benzoyl-1-O-(2-oxo-1,3,2-dioxaphospholan)-D-erythro-ceramide is not purified or isolated.

2. A method for synthesizing N-palmitoyl-D-erythro-sphingomyelin, comprising performing the method of claim 1 and allowing N-palmitoyl-3-O-benzoyl-D-erythro-sphingomyelin to react with sodium methoxide under conditions that are effective to yield N-palmitoyl-D-erythro-sphingomyelin.

3. The method of claim 1, wherein the trimethylamine is added as a liquid.

4. The method of claim 1, wherein the trimethylamine is added in a gaseous form.

5. The method of claim 1, wherein the method is performed on a kilogram scale.

* * * * *

UNITED STATES PATENT AND TRADEMARK OFFICE
CERTIFICATE OF CORRECTION

PATENT NO. : 9,708,354 B2
APPLICATION NO. : 13/844379
DATED : July 18, 2017
INVENTOR(S) : Daniela Carmen Oniciu et al.

It is certified that error appears in the above-identified patent and that said Letters Patent is hereby corrected as shown below:

In the Claims

At Column 78, Lines 5-6, Claim 1 please replace
"N-palmitoyl-3-0-benzoyl-1-O-(2-oxo-1,3,2-dioxaphospholan)-D-erythro-ceramide" with
"N-palmitoyl-3-O-benzoyl-1-O-(2-oxo-1,3,2-dioxaphospholan)-D-erythro-ceramide".

Signed and Sealed this
Fifth Day of September, 2017

Joseph Matal
*Performing the Functions and Duties of the*
*Under Secretary of Commerce for Intellectual Property and*
*Director of the United States Patent and Trademark Office*